US012790722B2

(12) United States Patent
Yu

(10) Patent No.: US 12,790,722 B2
(45) Date of Patent: Nov. 10, 2026

(54) MERGING C(SP3)-H ACTIVATION WITH DNA-ENCODING

(71) Applicant: THE SCRIPPS RESEARCH INSTITUTE, La Jolla, CA (US)

(72) Inventor: Jin-Quan Yu, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 1122 days.

(21) Appl. No.: 17/778,069

(22) PCT Filed: Nov. 24, 2020

(86) PCT No.: PCT/US2020/062026
§ 371 (c)(1),
(2) Date: May 19, 2022

(87) PCT Pub. No.: WO2021/108411
PCT Pub. Date: Jun. 3, 2021

(65) Prior Publication Data

US 2023/0046065 A1 Feb. 16, 2023

Related U.S. Application Data

(60) Provisional application No. 62/940,063, filed on Nov. 25, 2019.

(51) Int. Cl.
*C40B 50/00* (2006.01)
*C12N 15/10* (2006.01)

(52) U.S. Cl.
CPC .......... *C40B 50/00* (2013.01); *C12N 15/1068* (2013.01)

(58) Field of Classification Search
CPC ............................ C40B 50/00; C12N 15/1068
See application file for complete search history.

(56) References Cited

U.S. PATENT DOCUMENTS

| | | | | |
|---|---|---|---|---|
| 5,573,905 | A | 11/1996 | Lerner et al. | |
| 2013/0281324 | A1* | 10/2013 | Gouliaev | C12N 15/1068 506/26 |
| 2019/0169607 | A1* | 6/2019 | Watts | C12Q 1/6811 |

FOREIGN PATENT DOCUMENTS

| | | | | |
|---|---|---|---|---|
| CN | 110331447 A | | 10/2019 | |
| WO | 1993020242 A1 | | 10/1993 | |
| WO | WO-2018166532 A1 | * | 9/2018 | C40B 80/00 |
| WO | WO-2019168654 A2 | * | 9/2019 | A61K 38/12 |

OTHER PUBLICATIONS

He et al. (Chem. Rev., 2017, 117:8754-8786) (Year: 2017).*
Zhu et al. (J. Amer. Chem. Soc., 2017, 139:16080-16083) (Year: 2017).*

(Continued)

*Primary Examiner* — Jeremy C Flinders
(74) *Attorney, Agent, or Firm* — VIKSNINS HARRIS PADYS MALEN LLP

(57) ABSTRACT

Palladium-catalyzed C($sp^3$)-H arylation of aliphatic carboxylic acids, amides and ketones with DNA-encoded aryl iodides in water is disclosed. Also disclosed is DNA-encoded library (DEL) technology using the sequential functionalization of multiple C—H bonds, which provides a unique avenue for creating diversity and complexity from simple starting materials.

10 Claims, 8 Drawing Sheets

(56) References Cited

OTHER PUBLICATIONS

Gerry et al. (J. Amer. Chem. Soc., 2019, 141:10225-10235) (Year: 2019).*
Zhu et al. (J. Amer. Chem. Soc., 2018, 140:3564-3568) (Year: 2018).*
Chen, et al., "Ligand-Enabled β-C—H Arylation of α-Amino Acids Without Installing Exogenous Directing Groups", Angew Chem Int Ed Engl 56(6), 1506-1509 (2017).
Chowdhury, et al., "Regioselective β-Csp3-Arylation of β-Alanine: An Approach for the Exclusive Synthesis of Diverse β-Aryl-β-amino Acids", The Journal of Organic Chemistry 84 (5), 2512-2522 (2019).
Patent Cooperation Treaty, International Search Report and Written Opinion for PCT/US2929.962926m 11 pages, dated Mar. 18, 2021.
Phelan, et al., "Open-Air Alkylation Reactions in Photoredox-Catalyzed DNA-Encoded Library Synthesis", J Am Chem Soc 141(8), 3723-3732 (2019).
Shen, et al., "Pd(II)-Catalyzed Enantioselective C(sp3)-H Arylation of Free Carboxylic Acids", J Am Chem Soc 140, 6545-6549 (2018).
Wang, et al., "Ruthenium-Promoted C—H Activation Reactions between DNA-Conjugated Acrylamide and Aromatic Acids", Organic Letters 20 (16), 4764-4768 (2018).

* cited by examiner

Fig. 1A : Prior Art
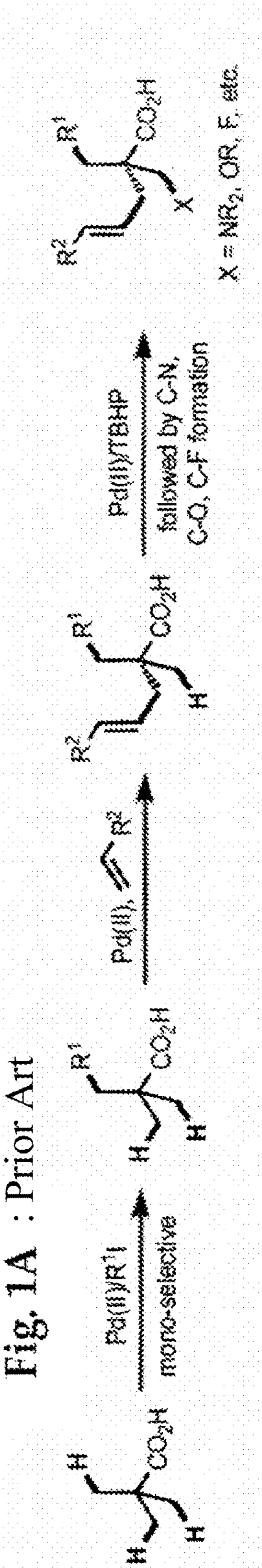
Fig. 1B : Prior Art
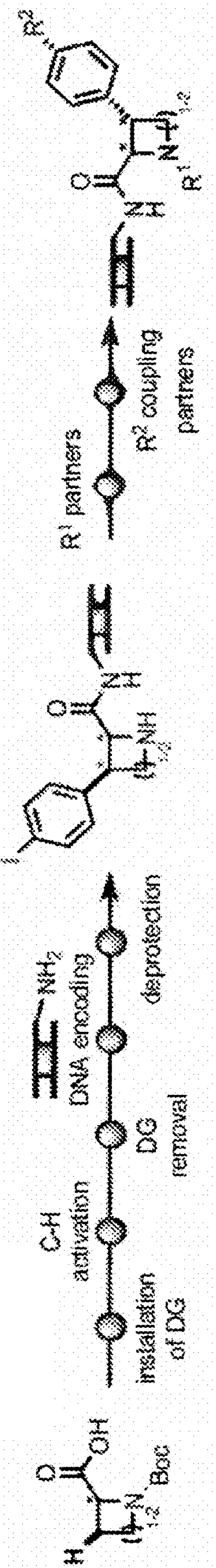
Fig. 1C
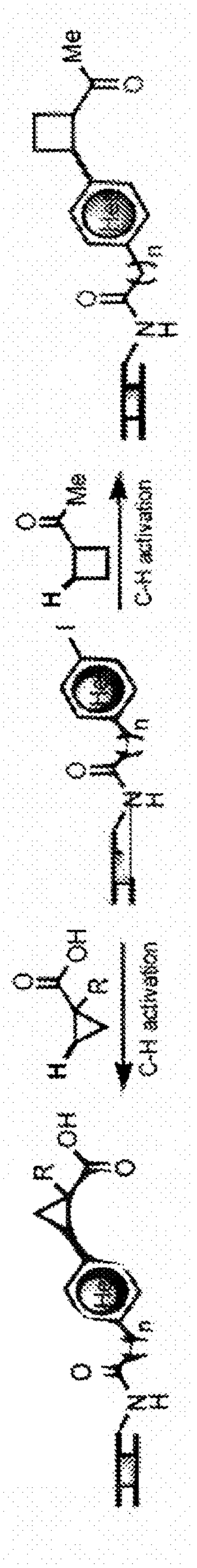

1 (5 nmol)

(300 equiv)

1', 8%

(10 nmol)

(100 equiv)

24

1, R = Me, 78%
2, R = Et, 62%
3, R = ${}^{i}$Pr, 72%
4, R = ${}^{n}$Bu, 56%
5, R = ${}^{i}$Bu, 48%
6, R = Ph, 32%

7, R = 46%
8, R = 72%
9, R = 48%

10, R = 46%
11, R = 61%
12, R = 64%
13, R = 49%

14, 61%

15, R = H, 28%
16, R = $CH_2CF_3$, 26%

17, R = H, 35%
18, R = ${}^{n}$Bu, 47%
19, R = 40%

20, R = H, 39%
21, R = Et, 40%

22, 55%
23, 73%
24, 67%
25, R = H, 47%
26, R = Cl, 52%
27, R = H, 60%
28, R = Cl, 58%
29, 74%

30, 82%
31, 73%
32, R = H, 38%
33, R = OEt, 59%
34, 45%
35, 29%
36, 33%
37, X = O, 76%
38, X = S, 67%

39, n = 1, R = H, 46%
40, n = 0, R = Me, 35%
41, 40%
42, 27%
43, 28%
44, 29%
45

45, R = $^i$Pr, 69%(60%)
46, R = $^n$Bu, 66%(84%)
47, R = cyclohexyl, 85%(65%)

48, 34%(54%)

49, 66%(41%)

50, R = H, 56%(60%); 51, R = $^i$Pr, 74%(78%)
52, R = Me, 85%(82%); 53, R = $^n$Pr, 73%(82%)
54, R = $^i$Bu, 85%(22%); 55, R = cyclopropylmethyl, 52%(47%)

56, 74%(80%)

57, R = Bn, 51%(0%)
58, R = 3-Cl$C_6H_4$, 35%(15%)

from **Ac-*L*-Val-OH**

59, 0%(0%)

from β-amino acid

60, 44%(64%)

61, R = H, 60%
62, R = Cl, 77%
63, $R^1$ = F, $R^2$ = H, 93%
64, $R^1$ = H, $R^2$ = F, 73%
65, 64%
66, 80%
67, 65%
68, R = H, 67%
69, R = OEt, 72%
70, 48%
71, X = O, 58%
72, X = S, 75%

68

73, 96%

β-C($sp^3$)-H arylation

74, $R^1$ = Me, $R^2$ = Me, 36%
75, $R^1$ = H, $R^2$ = Me, 65%
76, $R^1$ = H, $R^2$ = Et, 45%
77, $R^1$ = H, $R^2$ = H, 55%

78, R = H, X = $CH_2$, 40%
79, R = $CO_2Et$, X = $CH_2$, 20%
80, R = H, X = O, 40%
81, R = Me, X = NAc, 34%

82, 42%

83, 62%

84, R = Me, 42%
85, R = 39%

86, R = Et, 45%
87, R = Ph, 38%
88, R = 44%

89, 34%

90, 68%

91, 40%

92, 34%

γ-C($sp^3$)-H arylation 93, 22%

MERGING C(SP3)-H ACTIVATION WITH DNA-ENCODING

CROSS-REFERENCE TO RELATED APPLICATION

This application claims priority to U.S. application Ser. No. 62/940,063, filed on Nov. 25, 2019, whose disclosures are incorporated herein by reference.

GOVERNMENT SUPPORT

This invention was made with government support under Grant No. GM084019 awarded by the National Institutes of Health. The government has certain rights in the invention.

BACKGROUND ART

The concept of using DNA sequences to encode each single reagent in every reaction step during the split-pool synthesis was originally proposed by Brenner and Lerner[1]. DNA-encoded library (DEL) affinity selection against target proteins can now be performed at the benchtop, with millions or billions of DEL molecules incubated with the immobilized target protein in the same mixture[2]. The application of DEL technology has led to rapid identification of lead compounds for drug discovery[3].

Currently, increasing the hit rate as well as improving the drug-like properties of the lead compounds is a primary concern for constructing superior DELs. In this context, establishing diverse types of organic transformations compatible with DEL technology (water as solvent, presence of DNA, 1 mM concentration of DNA substrate) is of pivotal importance[4]. Development of on-DNA reactions faces a number of distinct challenges. DNA backbone degradation could occur under conventional reaction conditions; metal catalysts could be poisoned by oligonucleotides; at least 20% water is required as co-solvent for dissolving DNA-tagged substrates.

Over the past decade, advances in DNA-compatible reactions focused on nucleophilic aromatic substitution ($S_NAr$), cross-coupling, cycloaddition, and click chemistry to construct $C(sp^2)$-$C(sp^2)$[5], C—N[6], C—O[7], S—X bonds[8] and heterocycles[9]. Considering the well-known trends for incorporating $C(sp^3)$ carbon centers to build $C(sp^2)$-$C(sp^3)$ bonds[10] and avoiding high molecular mass and lipophilicity, coupling $C(sp^3)$-H bonds of simple aliphatic acids and ketones with DNA-encoded heteroaryls will be highly desirable. The availability of multiple C—H bonds of a wide range of carboxylic acids and ketones offers a unique opportunity to expand the accessible chemical space for DELs.

The recent development of a wide range of transformations of β—C—H bonds by the inventor and his co-workers demonstrates the potential for creating unprecedented diversity from simplicity[11] as are illustrated schematically in the panel of FIG. 1A. The attractiveness of using C—H arylation of carboxylic acid derived substrates to build DNA-encoded libraries is evident from a recent study where C—H activation reactions were performed in organic solvent and the DNA tags were subsequently attached individually. However, this approach does not allow encoding each single reagent in every reaction step during the split-pool synthesis, thus limiting the number of available building blocks and thereby the size of the library[12] (FIG. 1B).

In contrast, using C—H activation as a coupling step on DNA allows much larger libraries to be constructed. Notably, despite the use of a very powerful directing group, $C(sp^3)$-H activation reactions have not been successful in the presence of DNA thus far[13]. Development of on-DNA $C(sp^3)$-H activation of different classes of substrates is contemplated herein that can be employed sequentially to build DELs with enriched $C(sp^3)$ character, chiral centers, small rings and heterocycles as shown schematically in FIG. 1C, and specifically exemplified hereinafter.

SUMMARY OF THE INVENTION

The present invention contemplates a method for preparing an aqueous composition containing a library having a plurality of different bifunctional molecules, as well as a library itself. A contemplated method contemplates the steps of: reacting a bifunctional linker molecule B having termini A' and C' according to the formula A'-B—C' that is present in one or more aliquots of aqueous compositions. Terminus C' contains a bonded (tethered) iodo-substituted aromatic ring moiety that is free of secondary ring nitrogen atoms, and terminus A' contains an identifier nucleotide sequence precursor, Z'. The linker terminal C' iodo-substituted aromatic ring moiety is reacted by palladium-catalyzed arylation at a β-$C(sp^3)$-H or γ-$C(sp^3)$-H position of one or more reactant $C_4$-$C_{16}$ aliphatic carboxylic acid, carboxamide or masked ketone units, X'. A different X' is reacted in each aliquot, as is a different nucleotide identifier sequence precursor, Z', with terminus A' of the linker, to form an aqueous composition containing bifunctional molecules having the Formula (I), $Z_{n\alpha}$-A-B—C—$X_{n\alpha}$.

In Formula (I), n is a position identifier for X and Z, and is an integer from 1 to 10, preferably 1 to about 6, and more preferably 2 to about 5, such that when n is 1, X and Z are located most proximal to the linker B, and "α" identifies one or more specific reacted $C_4$-$C_{16}$ aliphatic carboxylic acid, carboxamide or masked ketone units X, and the corresponding, paired one or more identifying paired DNA sequences, Z, in the thus formed bifunctional molecule. Each Z' or Z is paired with and identifies a particular X' or X, respectively. Optionally, reacted aqueous aliquot compositions containing approximately equal amounts of bifunctional molecules so formed are admixed to form a single composition containing a mixture of bifunctional molecules in approximately equal numbers (amounts).

The carboxylic acid, carboxamide or masked ketone functionality present in one or more aliquots of the one or more aqueous compositions that contain bifunctional molecules of Formula (I), $X_{n\alpha}$, is reacted with one or more iodo-substituted aromatic ring moieties, W', that is free of secondary ring nitrogen atoms as is every further iodo-substituted aromatic ring moiety used herein, and is the same or different from that present at terminus C'. One or more precursor nucleotide sequence identifiers, Y', reacts with $Z_{n\alpha}$ to form one or more aqueous compositions containing bifunctional molecules having the Formula (II), $Y_{n\beta}$—$Z_{n\alpha}$-A-B—C—$X_{n\alpha}$—$W_{n\beta}$. "β" identifies one or more specific reacted chemical groups W and the corresponding one or more paired DNA sequence identifiers of Y in the bifunctional molecule of Formula (II).

Reacted aqueous aliquot compositions so formed containing approximately equal amounts of bifunctional molecules are optionally admixed to form a single composition containing an approximately equal mixture of bifunctional molecules. Each Y' or Y is paired with and identifies a particular W' or W, respectively.

The one or more iodo-substituted aromatic ring moieties, $W_{n\beta}$, present in the aqueous composition or aliquots thereof containing a bifunctional molecule of Formula (II) is reacted by palladium-catalyzed arylation at the β-C($sp^3$)-H or γ-C ($sp^3$)-H position of one or more $C_4$-$C_{16}$ aliphatic carboxylic acid, carboxamide or masked ketone unit that is the same or different from that reacted previously, V'. One or more precursor nucleotide sequence identifiers T' is reacted with $Y_{n\gamma}$ to form one or more compositions containing bifunctional molecules of Formula (III), $T_{n\gamma}$-$Y_{n\beta}$~$Z_{n\alpha}$-A-B—C—$X_{n\alpha}$—$W_{n\beta}$—$V_{n\gamma}$.

Each T' or T is paired with and identifies a particular V' or V, respectively. Additionally, γ identifies one or more specific $C_4$-$C_{16}$ aliphatic carboxylic acid, carboxamide or masked ketone units V and the corresponding one or more identifying paired DNA sequences of Y in the bifunctional molecule.

It is to be understood in regard to the above outlined reaction sequence, that at least one set of reaction steps includes a plurality of aliquots of an aqueous composition that contains bifunctional molecules that individually reacted with a reactant different from that reacted with bifunctional molecules in another aliquot at that step, followed by combining the aliquots produced to form an aqueous composition containing admixture of a plurality of different bifunctional molecules that constitute a library of said bifunctional molecules in an aqueous composition.

It is also to be understood in reference to reactants or bifunctional molecules that Z, A, C, X, Y, W, T and V are reacted forms of the corresponding Z', A', C', X', Y'W', T' and V'.

Two or more of the aliquots containing bifunctional molecules of Formula III are combined to form an aqueous composition containing an admixture of bifunctional molecules, thereby forming an aqueous composition containing the library. A library so formed can be isolated by separation from the aqueous composition as by lyophilization, precipitation with an organic solvent, chromatography and other means well known to skilled workers.

It is still further to be noted that the synthesis of a contemplated library of bifunctional molecules need not stop after three cycles of reaction steps as illustrated above, but can continue for several further cycles of reaction that follow the pattern set out above. Two cycles to about 7 are preferred, with 3 to about 5 reaction cycles being more preferred.

A library having a plurality of different bifunctional molecules having the Formula (III) bifunctional molecules of Formula (III), Z, A, C, X, Y, W, T and V are is also contemplated. In a library of bifunctional molecules of Formula III, Z, A, C, X, Y, W, T and V have the same meanings as previously provided, as do the subscripted symbols nγ, nβ and nα. Thus, $T_{n\gamma}$-$Y_{n\beta}$—$Z_{n\alpha}$-A is a mixture of polynucleotide sequences in which the specific identifiers identify the reacted iodo-substituted aromatic ring moieties and $C_4$-$C_{16}$ aliphatic carboxylic acid, carboxamide or masked ketone units that constitute the reacted building blocks of C—$X_{n\alpha}$—$W_{n\beta}$~$V_{n\gamma}$ in a mixture of bifunctional molecules of a library.

Preferably, linker B includes an oligonucleotide sequence long enough to be a primer for duplication polymerase chain reaction (PCR), about 18-22 base pairs (bp), and that also contains the recognition sequence of a predetermined restriction endonuclease that permits cleavage of the polynucleotide sequence of the $T_{ni}$-$Y_{ni}$—$Z_n$-A identifiers. It is further preferred that each identifier oligonucleotide sequence be double stranded DNA and that the specific identifier $T_{ni}$-$Y_{ni}$—$Z_n$-A polynucleotide sequence also be double stranded DNA.

It is also preferred that each of the specific identifier double stranded DNA oligonucleotides contains two restriction endonuclease recognition sites, one on either side of the specific identifier nucleotide sequence of the reactant used in synthesis. If the same endonuclease recognition site is placed on either side of all of the oligonucleotides present at a given position of the bifunctional molecules, cleavage with that endonuclease provides a number of identifier DNA oligos that can be separated and identified using mass spectral analysis.

A skilled worker can also admix a target binding protein with a bifunctional molecule library or sublibrary, capture those library molecules that bind and then conduct a pcr reaction on any target-bound bifunctional molecule, followed by sequencing of the replicated DNA.

It is further preferred in some embodiments that each aromatic ring moiety contain a six-membered ring, whereas it is preferred in other embodiments that each aromatic ring moiety contains a five-membered ring. In still other embodiments, both 5- and 6-membered aromatic ring moieties are present in a library of bifunctional molecules. In some preferred embodiments, each aromatic ring moiety is carbocyclic, whereas in other preferred embodiments each aromatic ring moiety is heterocyclic. In further preferred embodiments, at least one aromatic ring moiety is carbocyclic and at least one aromatic ring moiety is heterocyclic.

In still further preferences, at least one of the $C_4$-$C_{16}$ aliphatic carboxylic acid, carboxamide or masked ketone contains a 3- or 4-membered ring bonded to the carbonyl carbon atom, and the reacting 3- or 4-membered ring contained a β-C($sp^3$)-H at the position of arylation bond formation.

A method of carrying out an aqueous arylation reaction of a $C_4$-$C_{16}$ aliphatic carboxylic acid, carboxamide or masked ketone at a position β- or γ- to the position of the carboxylic acid, carboxamide or masked ketone carbonyl carbon atom is also disclosed hereinafter.

BRIEF DESCRIPTION OF THE DRAWINGS

In the drawings forming a portion of this disclosure,

FIGS. 1A, 1B and 1C illustrate the exploitation of diversity of C—H activation in a DNA-encoded library (DEL). FIG. 1A illustrates a schematic synthesis of combinatorial chemical libraries through sequential C—H activation[11], FIG. 1B is a schematic representation of Off-DNA C—H activation for access to DEL[12], and FIG. 1C schematically illustrates sequential on-DNA C—H activation for access to DEL as described herein. Asterisks indicate the presence of a chiral center at the atom. TBHP, tert-butyl hydroperoxide; Boc, tert-butyloxycarbonyl group; DG, directing group; and

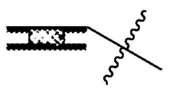

represents a linker including a bonded DNA sequence and a bond.

Figure 2A:
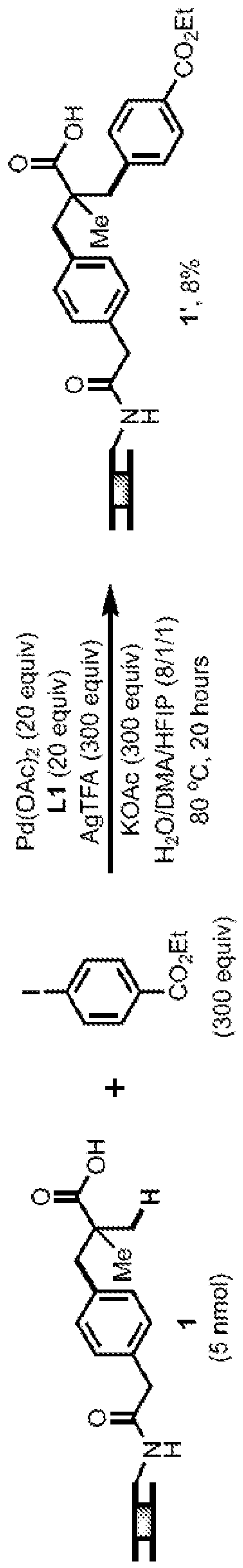
Figure 2B:
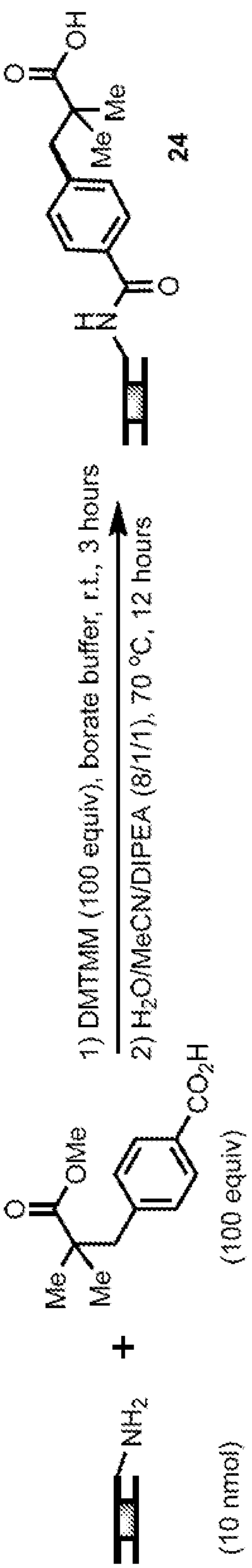

FIGS. 2A and 2B illustrate the utility of multiple C—H activation in DEL synthesis. illustrating a further addition to Compound 1 that itself was formed by C—H activation to form Compound 1'. FIG. 2B shows the amide-forming reaction between a DNA-bonded linker group amine an aromatic carboxylic acid that illustrates the reliability of the present on-DNA C—H reaction.

Figure 3A:
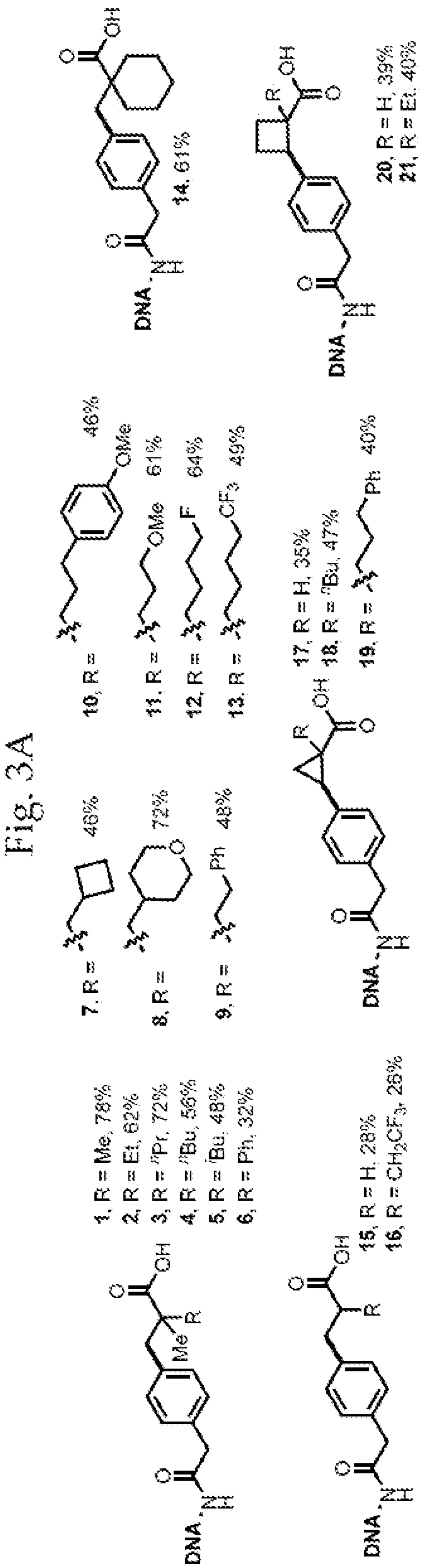
Figure 3B:
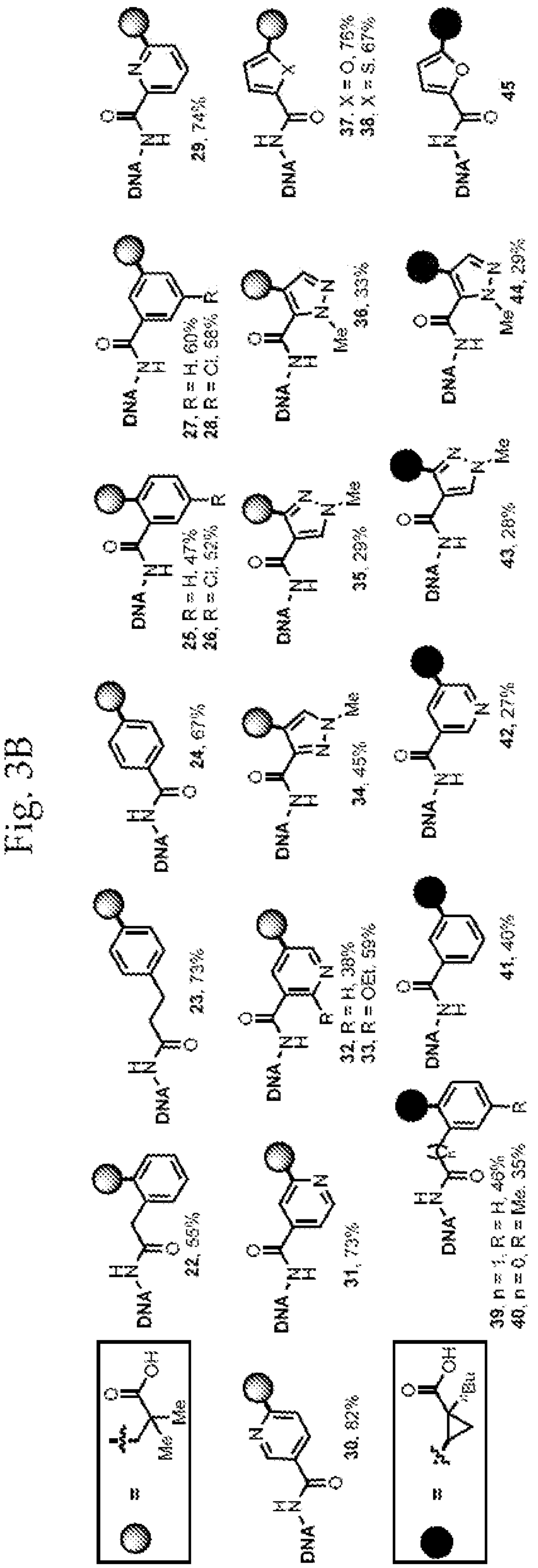

FIGS. 3A and 3B illustrate aqueous arylation products and yields obtained between an amine-terminated tethering linker (DNA-NH—) bonded to an iodo-substituted aromatic ring-moiety and the β-C($sp^3$)-H of a $C_4$-$C_{16}$ carboxylic acid, carboxamide or masked ketone. The general reaction, reactants, catalysts, oxidants and their concentrations, as well as temperature and duration of reactions, providing standard conditions under which the reactions of FIGS. 3A and 3B were carried out are shown in Table 1. Unless otherwise noted, condition of entry 1 of Table 1 was used as the standard condition in the reactions whose yields are shown in both of FIGS. 3A and 3B. FIG. 3A illustrates products and yields for the reaction of a single iodo-substituted aromatic ring-moiety bonded to an amine-terminated linker (DNA-NH—) and several different carboxamide-activating $C_4$-$C_{16}$ carboxylic acids that each have a β-C($sp^3$)-H relative to the carboxamide carbonyl carbon atom and having a substituent R at the α-position relative to both the carboxamido nitrogen atom and the carboxyl carbon atom. A chiral ligand, L1, shown in Table 1 was present for reactions whose yields are shown in FIG. 3A and absent in reactions whose yields are shown in FIG. 3B. FIG. 3B illustrates the reaction products and yields of pivalic acid or 1-butylcyclopropane-1-carboxylic acid, A23

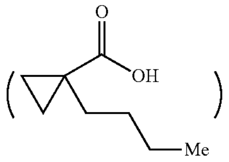

with several different iodo-substituted aromatic ring moieties having different aromatic ring structures and different positioning of the iodo substituent. Exceptions: Compound 2: corresponding A, 500 mM; for Compounds 3-13, 18, 19 and 39-45: AgTFA, 300 mM; corresponding A, 300 mM; 36 hours; for Compound 15: $Ag_3PO_4$, 200 mM; corresponding A, 300 mM; 36 hours; for Compound 21: corresponding A, 300 mM; 36 hours; for Compound 16: AgOTf, 300 mM; corresponding A, 300 mM; 36 hours; for Compound 17: $H_2O$/DMA (6/1).

Figure 4A:
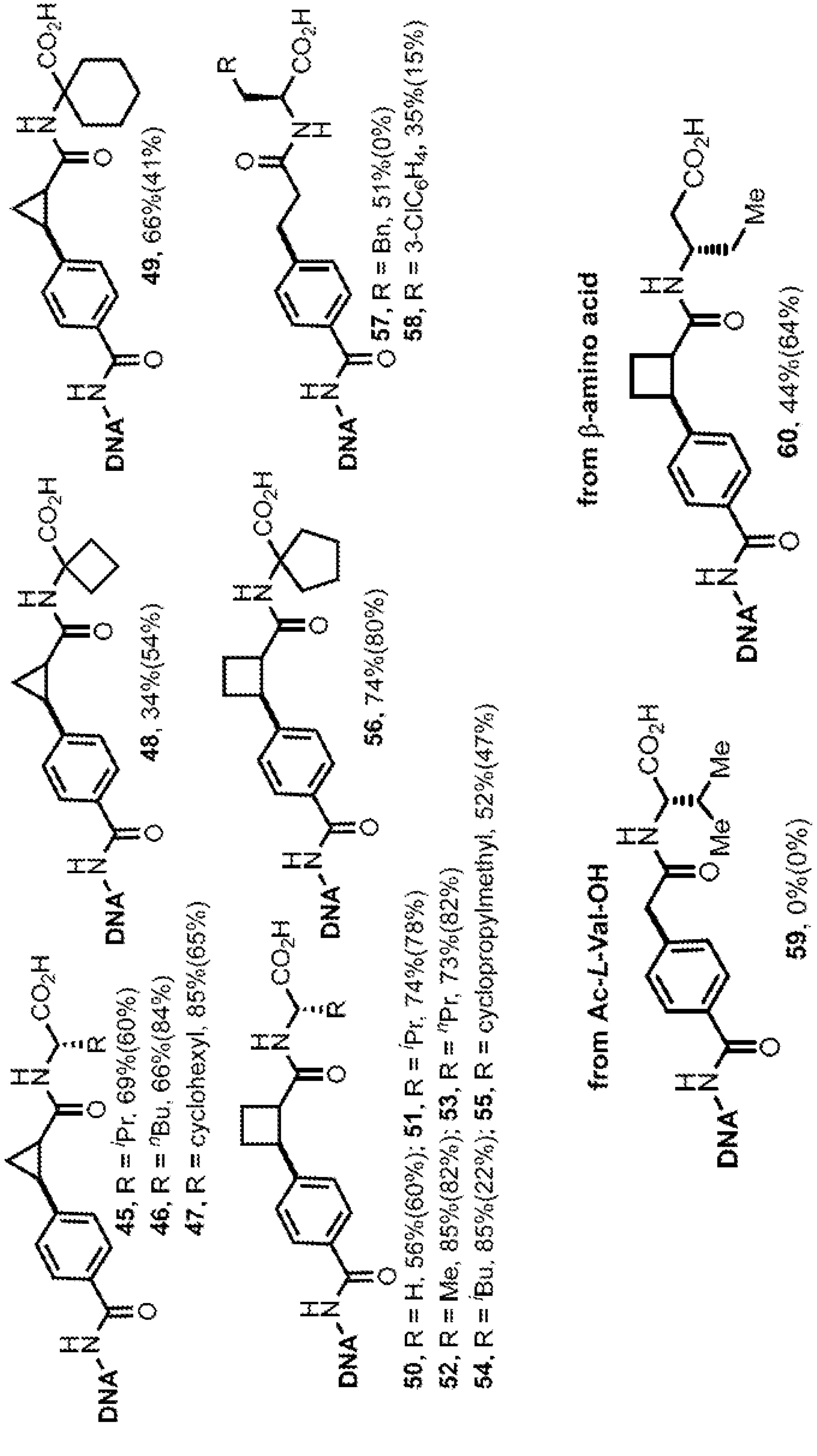
Figure 4B:
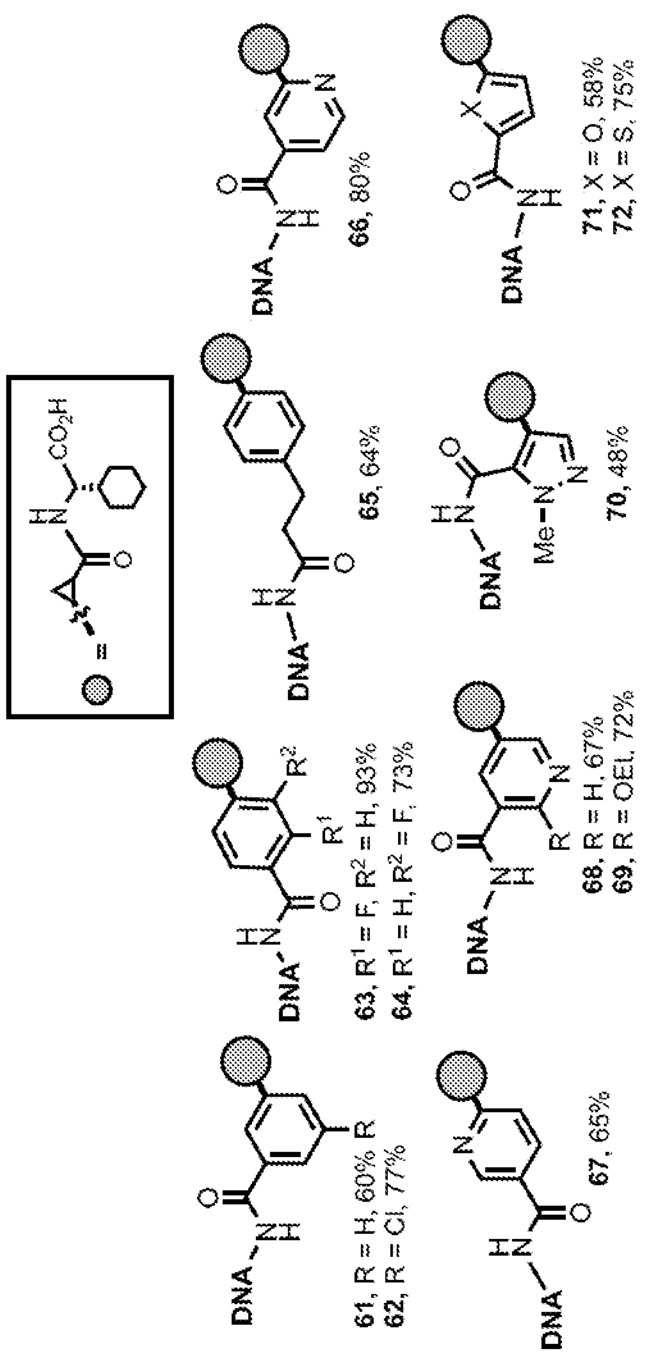
Figure 4C:
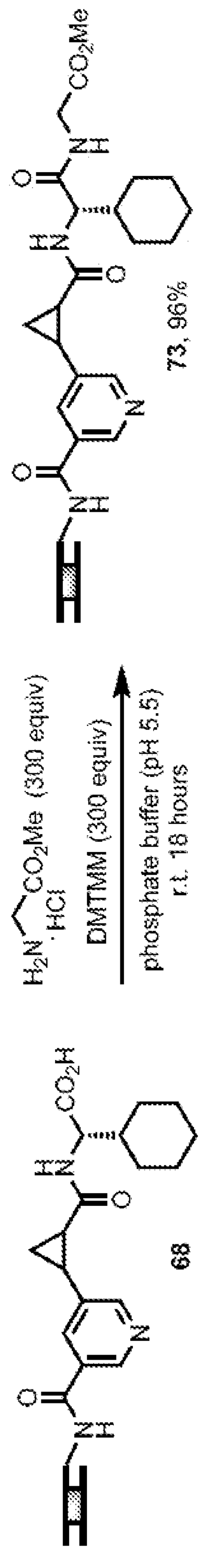

FIGS. 4A, 4B and 4C illustrate aqueous arylation products and yields obtained between an amine-terminated linker (DNA-NH—) tethering an iodo-substituted aromatic ring-moiety and the β-C($sp^3$)-H of a $C_4$-$C_{16}$ carboxylic acid. FIG. 4A illustrates the reaction, reactants, catalysts, oxidants and their concentrations, as well as temperature and duration of reactions, providing standard conditions under which the reactions of FIGS. 4B and 4C were carried out. FIG. 4B illustrates products and yields for the reaction of a single iodo-substituted aromatic ring-moiety bonded to an amine-terminated linker (DNA-NH—) and several different $C_4$-$C_{16}$ carboxylic acids that each have a β-C($sp^3$)-H and having a substituent R at the α-position relative to both the carboxyl carbon atom and the carboxamido nitrogen atom. FIG. 4C illustrates the amidification of a product arylated DNA-tethered aromatic moiety, Compound 68 shown in FIG. 4B, and glycine methyl ester in pH 5.5 buffer at room temperature for about 16-18 hours (overnight) to form Compound 73. DMTMM=4-(4,6-dimethoxy-1,3,5-triazin-2-yl)-4-methylmorpholinium chloride.

Figure 5A:
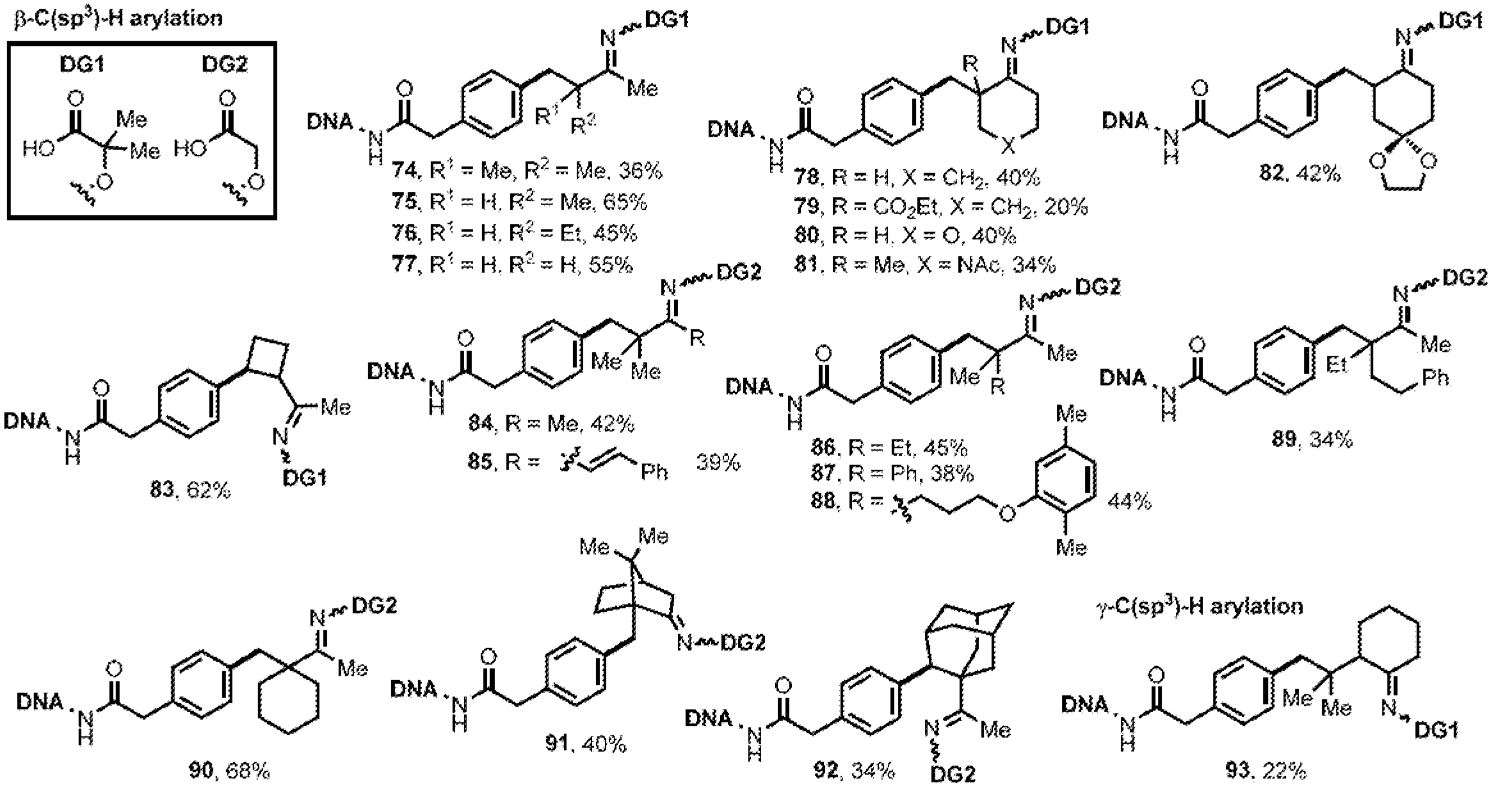
Figure 5B:
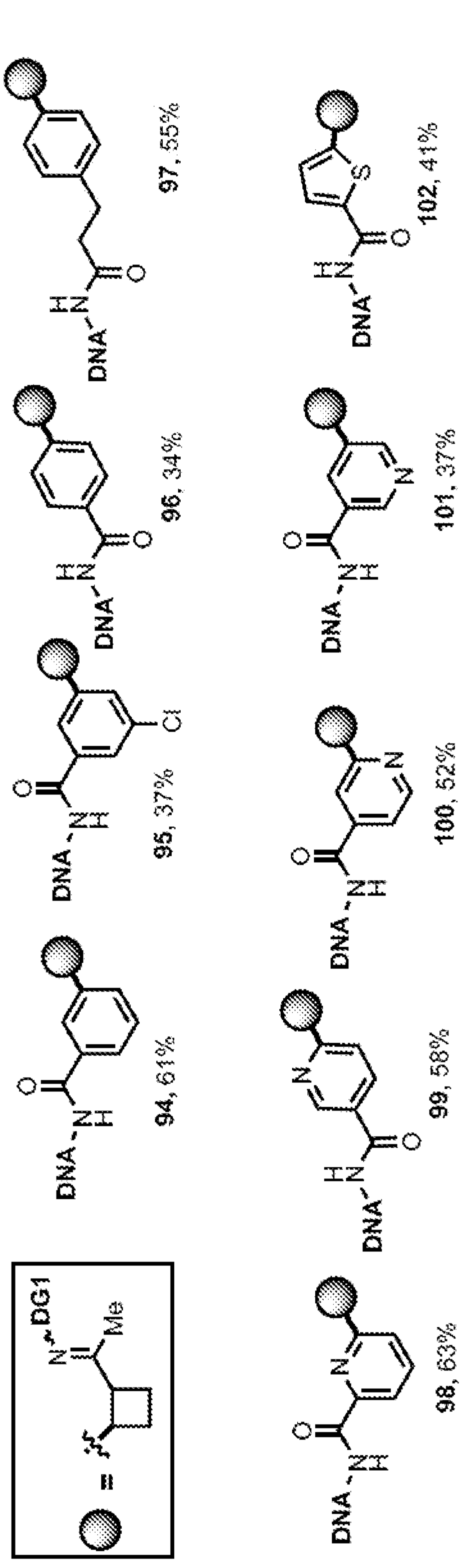
Figure 5C:
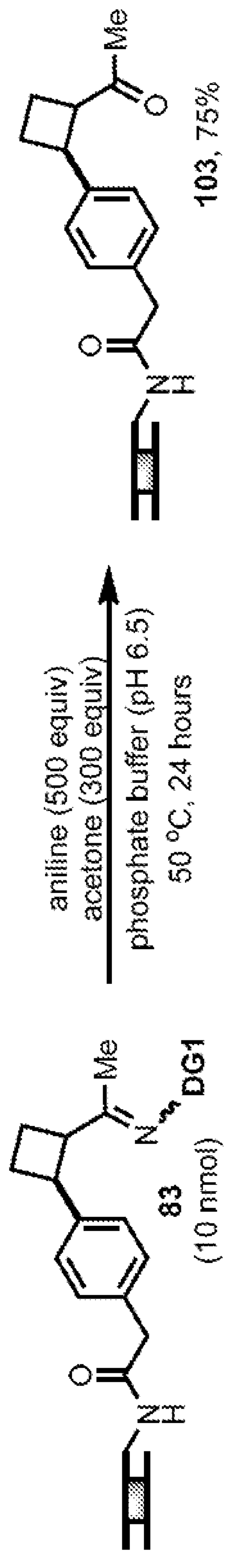
Figure 5D:
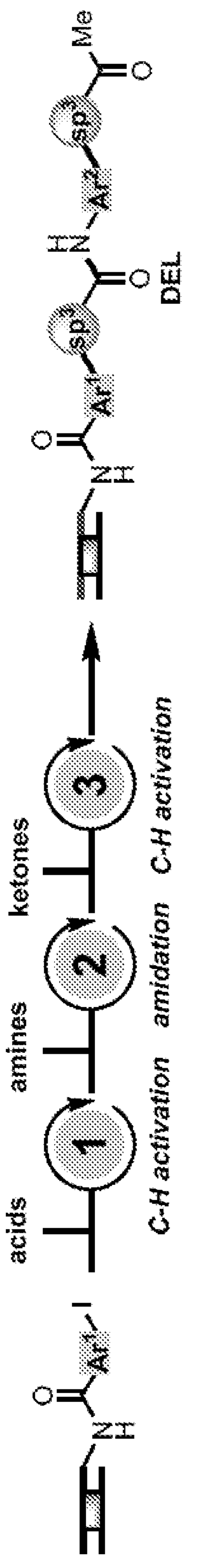
Figure 5E:
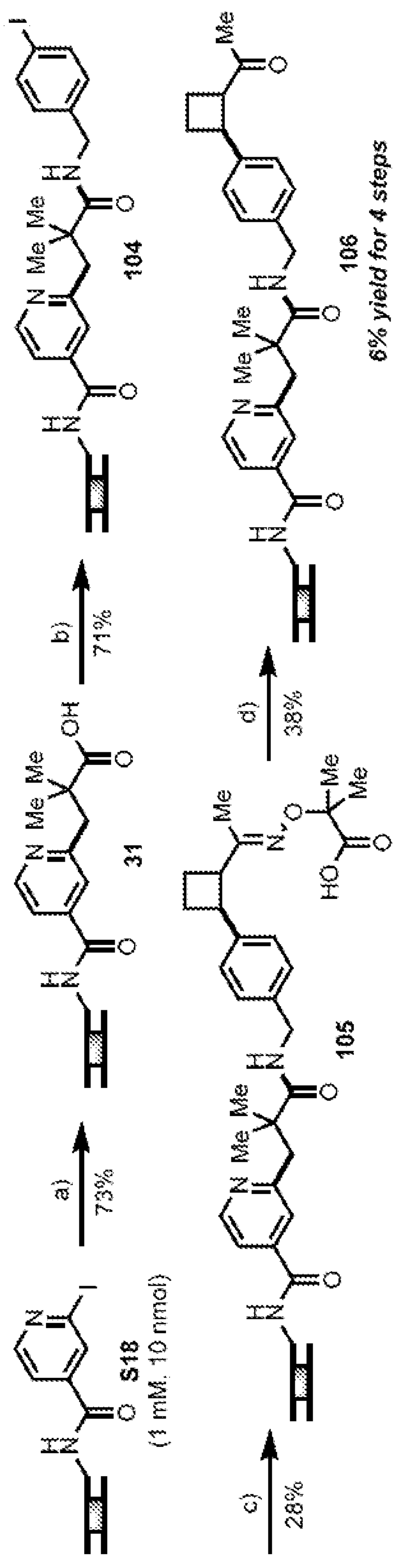

FIGS. 5A through 5D illustrate results of arylation reactions of a DNA-tethered iodo-substituted aromatic moiety with masked ketones containing β-C($sp^3$)-H and γ-C($sp^3$)-H groups. The reactions were carried out using the standard conditions shown in Table 3 hereinafter except as noted below for particular numbered compounds. More specifically, FIG. 5A illustrates aqueous arylation product yields obtained at the β-position relative to the masked ketone carbonyl carbon atom that was previously and reversibly masked as an oxime whose hydroxyl group was bonded to either of two exemplary directing groups, DG1 and DG2. FIG. 5B illustrates aqueous arylation product yields obtained at the β-position relative to a similarly masked ketone carbonyl carbon atom reacted with various different tethered iodo-substituted aromatic ring moieties having the iodo group at varying ring positions. FIG. 5C illustrates a de-blocking reaction to remove the DG1 ketone carbonyl blocking group to form Compound 103 from Compound 83. FIG. 5D illustrates a schematic flow chart of a contemplated synthetic procedure involving multiple C—H activation reactions for building DEL diversity through multiple C—H activations and reactions. FIG. 5E illustrates a representative synthesis for Compound 106 in which conditions for the steps [a), b), c) . . . etc.] were as follows: a) A1

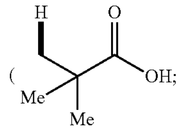

1000 equiv), $Pd(OAc)_2$ (10 equiv), L1

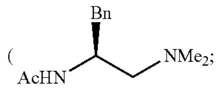

20 equiv), $Ag_2CO_3$ (300 equiv) NaOAc (150 equiv), $H_2O$/DMA/HFIP (8/1/1), 80° C., 16 hours; b) 4-iodobenzylamine (300 equiv), DMTMM (300 equiv), phosphate buffer (pH 5.5), r.t. 16 hours; c) C10

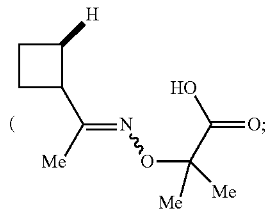

300 equiv), $Pd(OAc)_2$ (40 equiv), L8

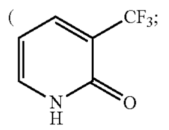 [SMILES: O=c1[nH]cccc1C(F)(F)F]

40 equiv), AgTFA (500 equiv), NaOAc (150 equiv), $H_2O$/DMA (9/1), 80° C., 20 hours; d) aniline (500 equiv), acetone (300 equiv), phosphate buffer (pH 6.5), 50° C., 24 hours.

DETAILED DESCRIPTION OF PREFERRED EMBODIMENTS

The present invention contemplates a method for preparing an aqueous composition containing a library having a plurality of different bifunctional molecules, as well as a library itself and a method of its manufacture. A principal reaction utilized in preparing a contemplated library is a platinum-catalyzed arylation reaction that is carried out in an aqueous medium. A contemplated arylation reaction forms a carbon-to-carbon (C—C) bond between a reactive substrate and an aromatic or heteroaromatic iodide.

In a contemplated reaction, the iodo group of an iodo-substituted aromatic ring moiety that is free of secondary ring nitrogen atoms is replaced with a bond to the former β-C($sp^3$)-H or γ-C($sp^3$)-H position of a $C_4$-$C_{16}$ aliphatic carboxylic acid, carboxamide or masked ketone unit, thereby forming a new C—C bond. Platinum-catalyzed arylation reactions between similar reactants have been reported in the literature, but were carried out in organic solvents that were free of added water. It is believed that this is the first report of carrying out such a reaction in an aqueous medium and also the first report of use of such a reaction in the preparation of bifunctional molecules and libraries containing same.

A method contemplates the steps of: reacting a bifunctional linker molecule B having termini A' and C' according to the formula A'-B—C' that is present in one or more aliquots of aqueous compositions. Terminus C' contains a bonded (tethered) iodo-substituted aromatic ring moiety that is free of secondary ring nitrogen atoms, and terminus A' contains an identifier nucleotide sequence precursor, Z'. The linker terminal C' iodo-substituted aromatic ring moiety is reacted by palladium-catalyzed arylation at a β-C($sp^3$)-H or γ-C($sp^3$)-H position of one or more reactant $C_4$-$C_{16}$ aliphatic carboxylic acid, carboxamide or masked ketone units, X'. A different X' is reacted in each aliquot, as is a different nucleotide identifier sequence precursor, Z', with terminus A' of the linker, to form an aqueous composition containing bifunctional molecules having the Formula (I), $Z_{n\alpha}$-A-B—C—$X_{n\alpha}$.

In Formula (I), n is a position identifier for X and Z, and is an integer from 1 to 10, preferably 1 to about 6, and more preferably 2 to about 5, such that when n is 1, X and Z are located most proximal to the linker B, and "α" identifies one or more specific reacted $C_4$-$C_{16}$ aliphatic carboxylic acid, carboxamide or masked ketone units X, and the corresponding, paired one or more identifying paired DNA sequences, Z, in the thus formed bifunctional molecule. Each Z' or Z is paired with and identifies a particular X' or X, respectively. Optionally, reacted aqueous aliquot compositions containing approximately equal amounts of bifunctional molecules so formed are admixed to form a single composition containing an approximately equal mixture of the bifunctional molecules.

A contemplated masked ketone is a compound whose carbonyl group is protected from reaction during the arylation, but can be readily deprotected to again provide a carbonyl group. Illustrative masked carbonyl groups include oximes, hydrazones and ketals. When used as an oxime, the hydroxyl group is itself protected from reaction as by formation of an ether linkage as is illustrated hereinafter.

Useful Pd(II) catalysts are well known in the art. Exemplary catalysts include $PdCl_2$, $Pd(TFA)_2$, $Pd(Piv)_2$, $[PdCl(C_3H_5)]_2$, $PdCl_2(PPh_3)_2$, $Pd(PPh_3)_4$, $Pd_2(dba)_3$, $[PdCl_2(MeCN)_2]$, $[Pd(OTf)_2 \cdot 4MeCN]$, and $[Pd(BF_4)_2 \cdot 4MeCN]$. Of these catalysts, $Pd(TFA)_2$, $Pd(Piv)_2$ and $Pd(OAc)_2$ are presently preferred. A contemplated catalyst is utilized in a catalytic amount. That amount is typically about 5 to about 40 mole percent based on the moles of reactive substrate, and more preferably about 10 to about 20 mole percent.

Illustrative basic salts include NaOAc, $Na_2CO_3$, $NaHCO_3$, $Na_2HPO_4$, $Na_2HPO_4$, $NaH_2PO_4$, $Na_3PO_4$, $KHCO_3$, KOAc, $K_2CO_3$, $K_3PO_4$, $K_2HPO_4 \cdot 3H_2O$, $Li_2CO_3$ and $Cs_2CO_3$. Of those salts, NaOAc and $Li_2CO_3$ usually provided the highest yields and are preferred.

A scavenger such as sodium diethyldithio-carbamate trihydrate is typically added to the reaction mixture after the arylation reaction is completed to assist in recovery of the palladium catalyst. Use of about 70 to about 90 equivalents of the scavenger per equivalent of the tethered iodo-substituted aromatic ring moiety achieves recovery of the palladium and a maximal amount to the initial DNA present.

A contemplated reaction medium optionally, but preferably includes a ligand that can promote both C—H cleavage and the subsequent functionalization steps. Effective C—H functionalization often requires a synergistic relationship between ligand and substrate coordinated to the metal center.

Although not usually needed for some reaction to proceed, the presence of a ligand molecule usually boosts the yield of a desired product. A ligand is typically present in the reaction composition at about 10 to about 30 mole percent based on the moles of substrate. Preferably, the ligand is present at about 20 mole percent. Alternatively, a ligand is present in an amount that is about 1.5 to about 4 times the molar amount of said palladium (II) catalyst.

A contemplated palladium-catalyzed arylation reaction mixture is maintained at a temperature of about 70° to about 100° C. for a time period sufficient to carry out the electrophilic insertion and form an arylated reaction product. More preferably, that temperature is about 75° to about 90° C. Reaction times are typically about 15 to about 30 hours, with times of about 18 to about 25 hours being usual.

The carboxylic acid, carboxamide or masked ketone functionality present in one or more aliquots of the one or more aqueous compositions that contain bifunctional molecules of Formula (I), $X_{n\alpha}$, is reacted with one or more iodo-substituted aromatic ring moiety that is free of secondary ring nitrogen atoms, W', that is the same or different from that present at terminus C'. One or more precursor nucleotide sequence identifiers, Y' with $Z_{n\alpha}$ to form one or more aqueous compositions containing bifunctional molecules having the Formula (II), $Y_{n\beta}$—$Z_{n\alpha}$-A-B—C—$X_{n\alpha}$—$W_{n\beta}$. Reacted aqueous aliquot compositions so formed containing approximately equal amounts of bifunctional molecules are optionally admixed to form a single composition containing an approximately equal mixture of bifunctional molecules. Each Y' or Y is paired with and identifies a particular W' or W, respectively. "β" identifies one or more specific reacted chemical groups W and the corresponding one or more paired DNA sequence identifiers of Y in the bifunctional molecule of Formula (II).

The one or more iodo-substituted aromatic ring moieties, $W_{n\beta}$, present in the aqueous composition or aliquots thereof containing a bifunctional molecule of Formula (II) is reacted by palladium-catalyzed arylation at the β-C($sp^3$)-H or γ-C($sp^3$)-H position of one or more $C_4$-$C_{16}$ aliphatic carboxylic acid, carboxamide or masked ketone unit that is the same or different from that reacted previously, V'. One or more precursor nucleotide sequence identifiers T' is reacted with $Y_{n\gamma}$ to form one or more compositions containing bifunctional molecules of Formula (III), $T_{n\gamma}$-$Y_{n\beta}$—$Z_{n\alpha}$-A-B—C—$X_{n\alpha}$—$W_{n\beta}$—$V_{n\gamma}$.

Each T' or T is paired with and identifies a particular V' or V, respectively. Additionally, γ identifies one or more specific $C_4$-$C_{16}$ aliphatic carboxylic acid, carboxamide or masked ketone units V and the corresponding one or more identifying paired DNA sequences of Y in the bifunctional molecule.

It is to be understood in regard to the above outlined reaction sequence, that at least one set of reaction steps includes a plurality of aliquots of an aqueous composition that contains a bifunctional molecule that individually reacted with a reactant different from that reacted in another aliquot at that step, followed by combining the aliquots produced to form an aqueous composition containing admixture of a plurality of different bifunctional molecules that constitute a library of said bifunctional molecules in an aqueous composition.

A linker is also referred to herein as a "head group". An illustrative head group used herein is shown below along with two abbreviations often

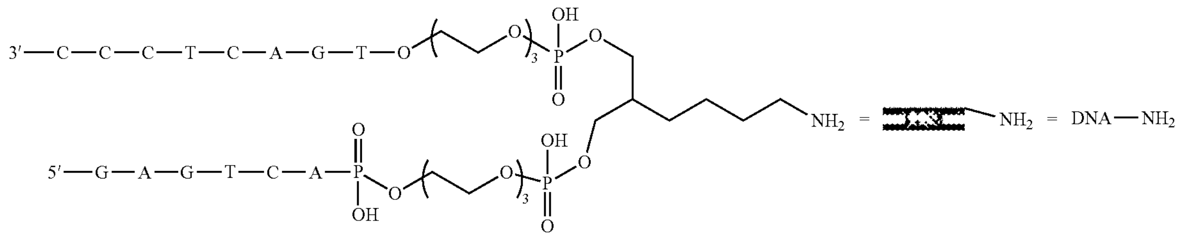

used herein for it:

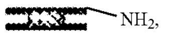

and DNA-$NH_2$. The depicted amine group, —$NH_2$, is a useful functionality to react with and tether the iodo-substituted aromatic moiety to the remainder of the head group, whereas the DNA sequences are readily extended by well-known methods of oligonucleotide synthesis.

The nucleotide sequence of the preferably double stranded oligonucleotide identifier Z' is used to identify the specific X' that was arylated at position subscript "n" in the "string" of organic residues added on to the linker. The subscripted Greek letter that accompanies each subscripted "n" stands for one up to about 40 different chemical structures and corresponding oligonucleotide sequences that identify each of those structures. In preferred practice, 1 to about 20 different chemical structures are utilized at each position "n" along with the same number of identifying DNA sequences at the same position "n" relative to B on the other side of the linear bifunctional molecule. More preferably, one to about 10 different chemical structures are utilized along with the same number of identifying DNA sequences present at each position in the bifunctional molecule.

In one preferred embodiment, a nucleotide sequence of a restriction endonuclease flanks both upstream and downstream of the X'-identifying sequence so that the positional identifier, as identified by endonuclease, can be readily removed for identification of its one or more reactant-identifying nucleotide sequences. It is preferred that the same endonuclease sequence is present on both sides of the identifying sequence so only one enzyme is needed to excise an identifier sequence at a given position in bifunctional molecule.

It is noted that each aqueous arylation is preferably carried out at a β-C($sp^3$)-H position relative to the carbonyl carbon of a carboxylic acid, carboxamide or masked ketone unit.

In a bifunctional molecule of Formula III, each T' or T is paired with and identifies a particular V' or V, respectively, and $Y_{ni}$, $Z_n$, A, B, C, $X_n$, and $W_{ni}$ are as previously defined.

Two or more of the aliquots containing bifunctional molecules of Formula III are combined to form an aqueous composition containing an admixture of bifunctional molecules, thereby forming an aqueous composition containing the library. A library so formed can be isolated by separation from the aqueous composition as by lyophilization, precipitation with an organic solvent, and other means well known to skilled workers.

It is also to be noted that the synthesis of a contemplated library of bifunctional molecules need not stop after three cycles of reaction steps as illustrated above, but can continue for several further cycles of reaction that follow the pattern set out above. Two cycles to about 7 are preferred, with 3 to about 5 reaction cycles being more preferred.

When a plurality of different residues is desired at a given position in the sequence, the bifunctional molecule-containing aqueous composition is divided into at least as many aliquots as the number of different reactants desired to be added along with an identifying DNA sequence for each along with flanking positional identifiers if desired.

If it is desired that the next, adjacent, position be occupied by a mixture, each reacted aliquot is again split into at least the number of reactants to be used at this step. The members of the next set of reactants are individually reacted with the growing bifunctional molecule in each of the newly divided aliquots, as is the next DNA sequence that identifies each, along with flanking restriction site sequences that identify the particular position, if desired.

The above variant and others of parallel synthesis whose products are pooled and then divided is illustrated using different syntheses in Brenner and Lerner, Proc Natl Acad Sci, USA 89:5381-5383 (June 1992), U.S. Pat. Nos. 5,573,905, 5,723,598 and 6,060,596, as well as in Houghten, Proc Natl Acad Sci, USA 82:5131-5135 (1985), Houghten et al., Biotechniques, 4(6):522-528 (1986), U.S. Pat. Nos. 4,631,211 and 5,763,193, each of whose disclosures are incorporated by reference.

If it is not desired for that next possible position to be a mixture, all of the previously reacted aliquots are combined providing a single composition that contains the mixed bifunctional molecules. Those mixed bifunctional molecules can then be reacted with a single reactant, used without further reaction or recovered for later use.

Thus, $T_{n\gamma}$-$Y_{n\beta}$—$Z_{n\alpha}$-A is a polynucleotide sequence in which the specific identifiers identify the reacted aromatic ring moieties and $C_4$-$C_{16}$ aliphatic carboxylic acid, carboxamide or masked ketone units that constitute the reacted building blocks of C—$X_{n\alpha}$—$W_{n\beta}$—$V_{n\gamma}$ in a bifunctional molecule of the library. Preferably, linker B includes an oligonucleotide sequence that contains the recognition sequence of a predetermined restriction endonuclease that permits cleavage of the polynucleotide sequence of the $T_{n\gamma}$-$Y_{n\beta}$—$Z_{n\alpha}$-A identifiers.

It is further preferred that each identifier oligonucleotide sequence be double stranded DNA and that the specific identifier $T_{n\gamma}$-$Y_{n\beta}$—$Z_{n\alpha}$-A polynucleotide sequence also be double stranded DNA. It is also preferred that each of the specific identifier double stranded DNA oligonucleotides contains two restriction endonuclease recognition sites, one on either side of the specific identifier nucleotide sequence of the reactant used in synthesis. Yet another preference is that a $C_4$-$C_{16}$ aliphatic carboxylic acid, carboxamide or masked ketone arylationally bonded to an aromatic ring moiety is bonded via a previously present β-C($sp^3$)-H position relative to the carbonyl group of the carboxylic acid, carboxamide or masked ketone.

It is further preferred in some embodiments that each aromatic ring moiety contain a six-membered ring, whereas it is preferred in other embodiments that each aromatic ring moiety contains a five-membered ring. In still other embodiments, both 5- and 6-membered aromatic ring moieties are present in a library of bifunctional molecules. In some preferred embodiments, each aromatic ring moiety is carbocyclic, whereas in other preferred embodiments each aromatic ring moiety is heterocyclic. In further preferred embodiments, at least one aromatic ring moiety is carbocyclic and at least one aromatic ring moiety is heterocyclic.

In still further preferences, at least one of the C4-$C_{16}$ aliphatic carboxylic acid, carboxamide or masked ketone contains a 3- or 4-membered ring bonded to the carbonyl carbon atom, and the reacting 3- or 4-membered ring contained a β-C($sp^3$)-H at the position of arylation bond formation.

A method of carrying out an aqueous arylation reaction of a $C_4$-$C_{16}$ aliphatic carboxylic acid, carboxamide or masked ketone at a position β- or γ- to the position of the carboxylic acid, carboxamide or masked ketone carbonyl carbon atom is also disclosed below.

An iodo-substituted aromatic ring moiety that is free of secondary ring nitrogen atoms, a reactant that is a $C_4$-$C_{16}$ aliphatic carboxylic acid, carboxamide or masked ketone containing a β-C($sp^3$)-H or γ-C($sp^3$)-H, a catalytic amount of a palladium (II) catalyst, a silver salt, a basic alkali metal salt, and an optionally present ligand that interacts with a $Pd^{2+}$ ion in aqueous media are dissolved or dispersed in an aqueous medium to form an aqueous reaction medium. That aqueous reaction medium is maintained for a period of about 15 to about 30 hours at a temperature of about room temperature (about 20° C.) to about 100° C., and preferably at about 70° C. to about 100° C., to provide a product aromatic ring moiety free of secondary ring nitrogen atoms bonded between the ring position formally occupied by the iodo substituent to the former position occupied by the β-C($sp^3$)-H or γ-C($sp^3$)-H of the $C_4$-$C_{16}$ aliphatic carboxylic acid, carboxamide or masked ketone.

In one preferred embodiment, the $C_4$-$C_{16}$ aliphatic carboxylic acid, carboxamide or masked ketone containing a β-C($sp^3$)-H or γ-C($sp^3$)-H is present in the aqueous reaction medium in a molar excess relative to the iodo-substituted aromatic moiety 10:1 to about 1200:1. In another preferred embodiment, the silver salt and basic alkali metal salt are present aqueous reaction medium at a molar ratio of about 2:1 to about 4:1, and the molar ratio of the silver salt to the iodo-substituted aromatic moiety is about 100:1 to about 400:1.

In another preferred embodiment, the ligand is present in an amount that is 1 to about about 1.5 to about 4 times the molar amount of the palladium (II) catalyst. A preferred ligand is selected from the group consisting of one or more of

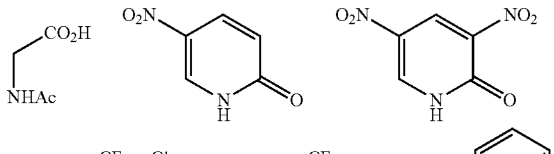

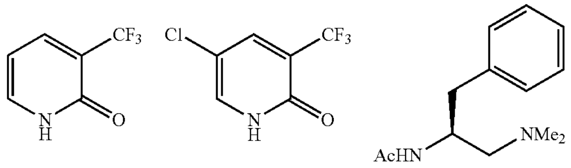

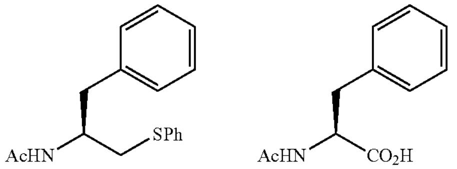

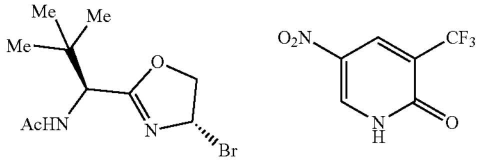

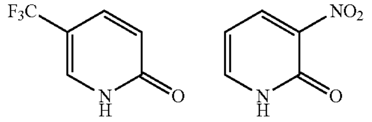

and

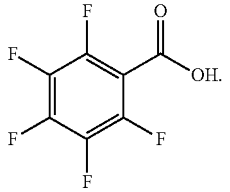

In yet another preferred embodiment, the iodo-substituted aromatic ring moiety that is free of secondary ring nitrogen atoms contains a single 5- or 6-membered aromatic ring, is itself linked to a DNA-containing linker designated "DNA-" and is selected from the group consisting of one or more of

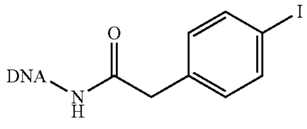

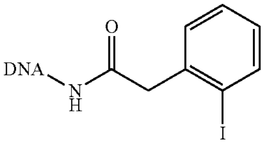

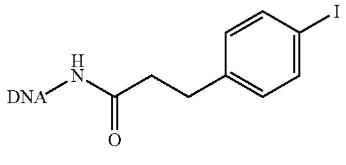

-continued
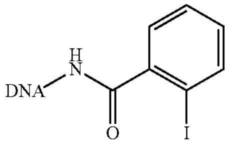
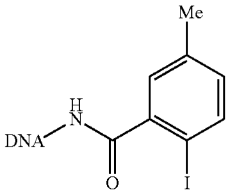
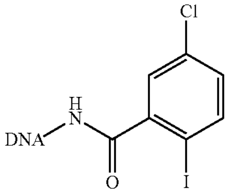
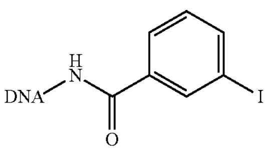
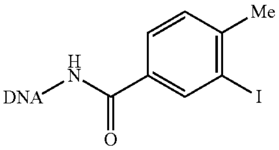
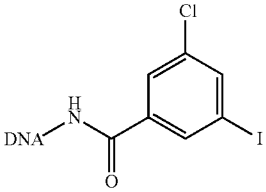
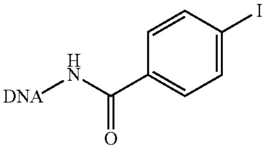
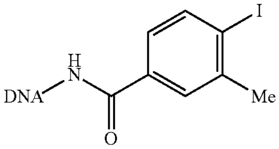
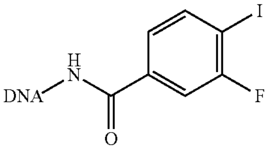
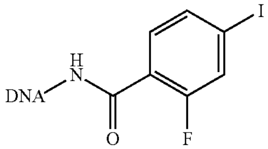
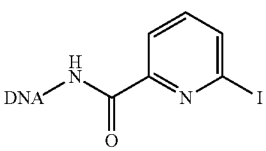
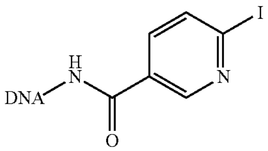
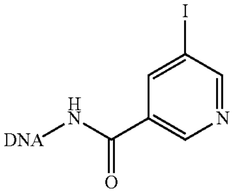
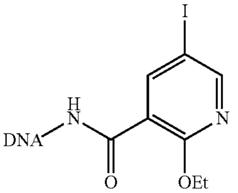
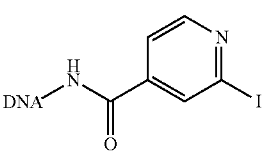
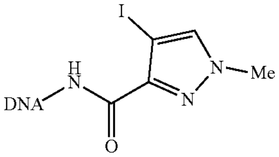
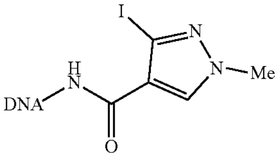
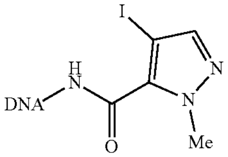
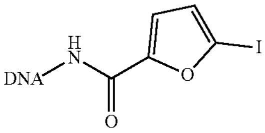 and
-continued
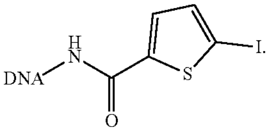
In some preferred embodiments, the masked ketone containing a β-C($sp^3$)-H or γ-C($sp^3$)-H is selected from the group consisting of one or more of
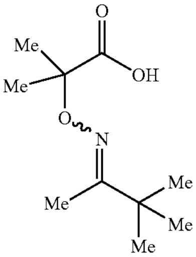
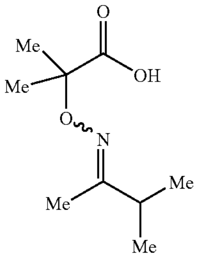
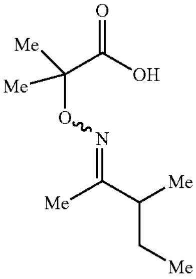
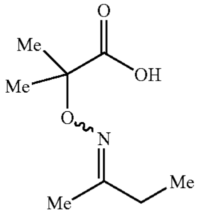
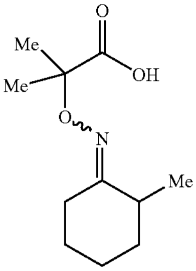
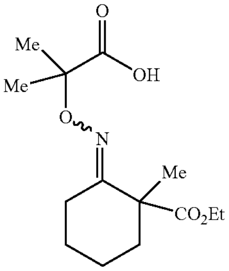
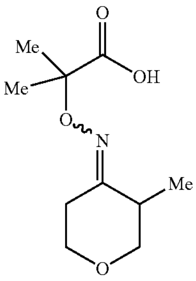
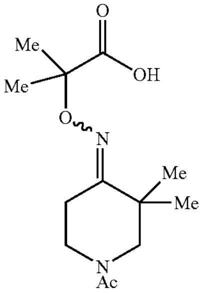

-continued

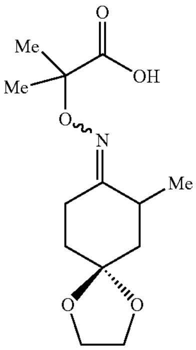

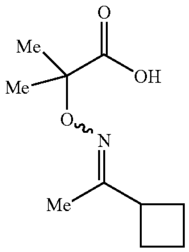

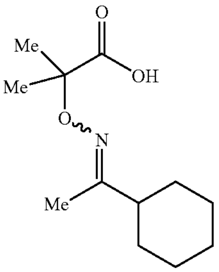

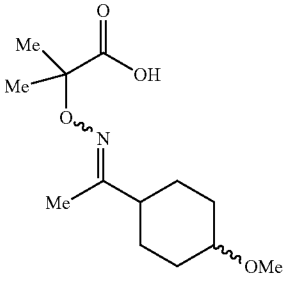

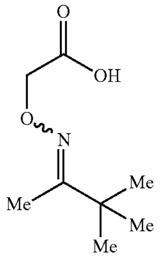

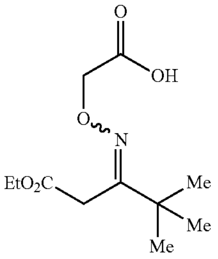

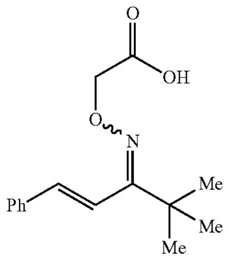

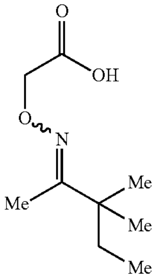

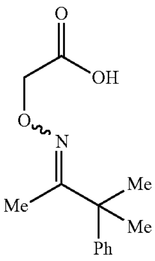

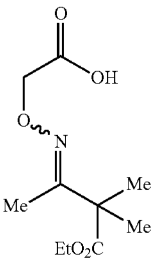

-continued

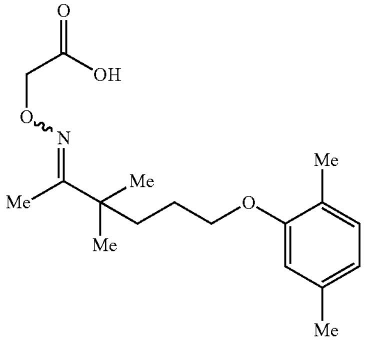

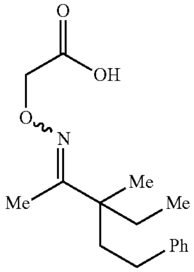

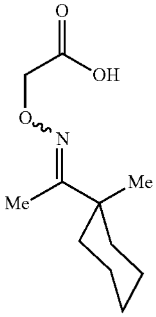

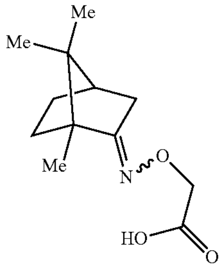

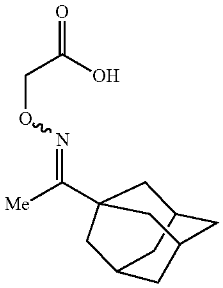

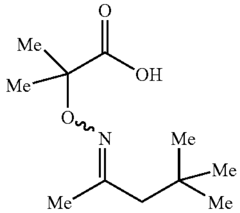

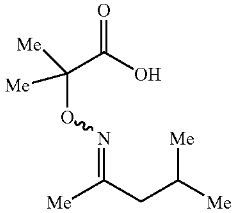

and

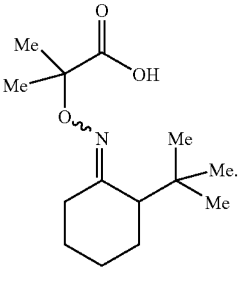

Results

Because carboxylic acids and (hetero)aryl iodides are ubiquitous building blocks for DNA-encoded libraries, the coupling of a DNA-tethered aryl iodide with a free carboxylic acid was first studied through Pd-catalyzed β-C—H arylation. This presented formidable challenges beyond the need to adapt the chemistry to aqueous conditions, notably the limited stability of the DNA towards low pH values and heat, the potential for interfering reactivity of the DNA bases, and the high dilution of the DNA-tethered component. Nonetheless, it was decided to develop this chemistry around free carboxylic acids.
Illustrative useful carboxylic acids having a β-C($sp^3$)-H or γ-C($sp^3$)-H are shown in the table below.
A1
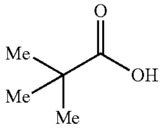
A2
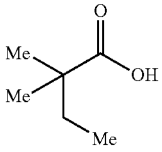
A3
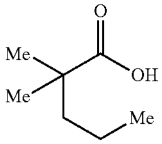
A4
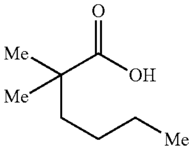
A5
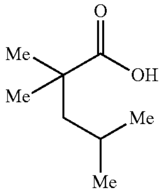
A6
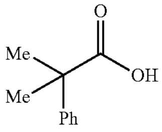
A7
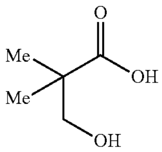
A8
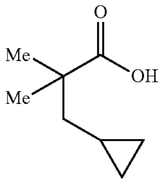
-continued
A9
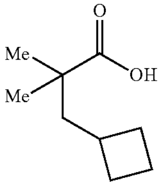
A10
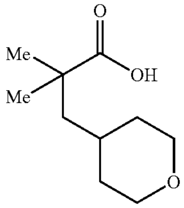
A11
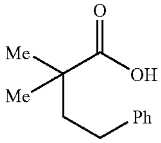
A12
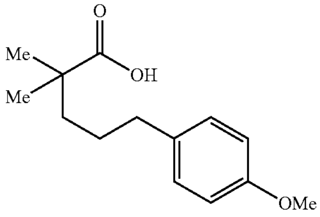
A13
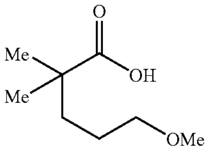
A14
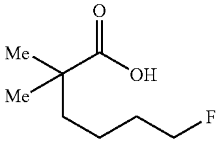
A15
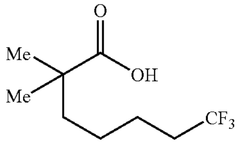
A16
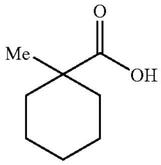
A17
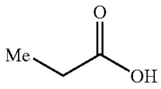

-continued

A18

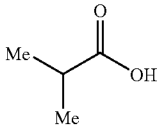

A19

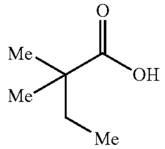

A20

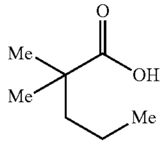

A21

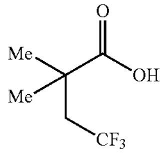

A22

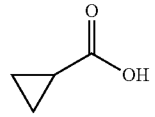

A23

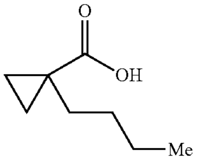

-continued

A24

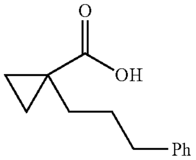

A25

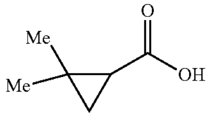

A26

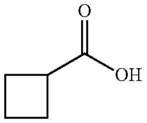

A27

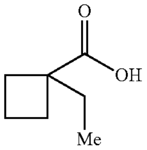

Guided by previous C—H arylation efforts[14], palladium source, ligand, silver source, base, and co-solvent were screened as illustrated in Tables 1 and 2, below.

The optimized conditions gave product Compound 1 in 78% yield with no di- or tri-arylation of pivalic acid (entry 1, Table 1). Palladium, silver, and heat were mandatory (entries 2 to 4, Table 1). No ligand was required (entry 5, Table 1), but amino acid-derived ligands improved the yield, with ligand Li found to be optimal.

TABLE 1

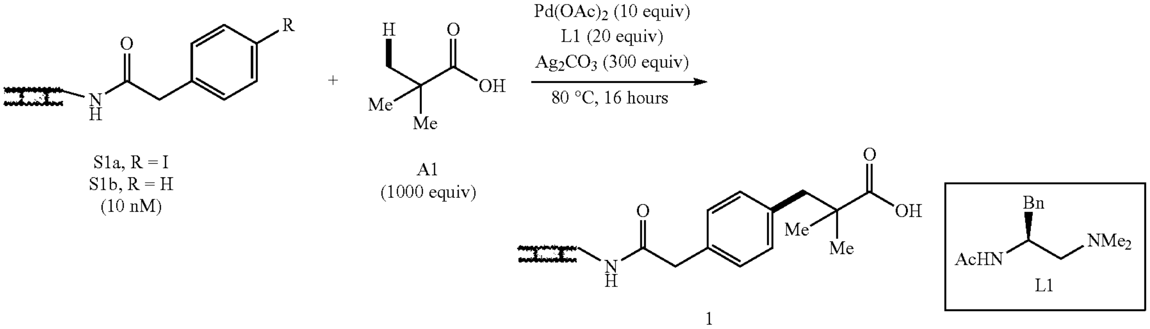

S1a, R = I
S1b, R = H
(10 nM)

A1
(1000 equiv)

1

L1

| Entry | Deviation from standard condition | 1 (%) |
|---|---|---|
| 1 | none | 78 |
| 2 | without $Pd(OAc)_2$ | 0 |
| 3 | without $Ag_2CO_3$ | 0 |
| 4 | r.t. instead of 80° C. | 0 |
| 5 | without L1 | 56 |
| 6 | S1b instead of S1a | 0 |

The main side reaction, protodeiodination (e.g., Compound S1b), was always present to a small extent due to the use of excess silver salt and palladium. Compound S1b containing no iodide was subjected to the reaction conditions and recovered intact, confirming that coupling occurs at the aryl iodide and not at some undetermined location on the DNA tag (entry 6, Table 1). Dithiocarbamate releases DNA from DNA-palladium complex as a result of its stronger coordination with palladium leading to insoluble complex.

After each reaction, the mixture was incubated with sodium diethyldithiocarbamate trihydrate in order to scavenge palladium. The level of DNA recovery was significantly influenced by the loading of the dithiocarbamate scavenger.

Examining the results shown in FIG. 3A, a broad range of carboxylic acids adjacent to quaternary carbon atoms are suitable for this chemistry, including those containing hydroxyl, ethers or fluorine (Compounds 2 to 14). However, acids adjacent to a secondary or tertiary carbon react with <30% yield (Compounds 15 to 16). Importantly, cyclopropane- and cyclobutanecarboxylic acids (desirable as alkene isosteres) are competent coupling partners (Compounds 17 to 21).

The mechanism of the Pd-catalyzed β-C—H arylation is well known to give the cis stereoisomer exclusively. LCMS analysis was unable to determine whether chiral ligand L1 gave any absolute stereoinduction.

The results shown in FIG. 3B illustrate that the aryl iodide substitution pattern is flexible (Compounds 22 to 28, 39 to 44). Although previously-published reaction conditions in organic solvent could not couple heteroaryl iodides[24,25], it was believed that conditions that tolerate DNA—the bases that contain nitrogen heterocycles—should allow coupling of heteroaryl iodides (e.g., pyridines and pyrazoles). This was indeed the case; heteroaryl iodides successfully reacted with carboxylic acids under the same reaction conditions (Compounds 29 to 38, 42 to 44). Because aryl and heteroaryl iodides react under the same conditions, they can both be present in a contemplated split-pool synthesis of a DEL.

As shown as part of Table 1 above, the standard reaction conditions for the reactions of FIGS. 3A and 3B are based upon starting with 10 nanomoles (nmol) of the DNA-linked aromatic iodide that is reacted with 1000 equivalents (equiv) of the carboxylic acid containing a β-C($sp^3$)-H or γ-C($sp^3$)-H. That reaction takes place in the presence of 10 equivalents of Pd( )$Ac)_2$, 120 equivalents of the ligand, 300 equivalents of $Ag_2CO_3$, 150 equivalents of NaOAC that are dissolved or dispersed in a medium containing water, dimethylacetamide and hexafluoro-2-propanol present at a ratio of 8:1:1. The reaction was carried out at a temperature of 80° C. for a time period of 16 hours.

Unless otherwise noted, those conditions were used as the standard condition. For Compound 2: the carboxylic acid was present at 500 equiv. For Compounds 3-14, 18, 19, and 39-44: AgTFA, 300 equiv; carboxylic acid 300 equiv, 36 hours. For Compound 15: $Ag_3PO_4$, 200 equiv; carboxylic acid, 300 equiv; 36 hours. For Compound 21: carboxylic acid, 300 equiv; 36 hours. For Compound 16: AgOTf, 300 equiv; carboxylic acid, 300 equiv; 36 hours. For Compound 17: $H_2O$/DMA (6/1).

In addition, the β-C($sp^3$)-H arylated product attached to DNA can undergo the second carboxylate-directed C(sp3)-H arylation to obtain the DNA-tagged product 1'. This is shown in FIG. 2A. Furthermore, product 24 was selected to proceed off-DNA synthesis and demonstrate the reliability of the present on-DNA C—H reaction. This is shown in FIG. 2B.

The carboxylic acids in the products from the above chemistry can be further derivatized. One interesting possibility is coupling to amino acids in order to enhance the chiral recognition potential of the resultant DNA-encoded libraries. An opportunity in these cases to develop a ligand-less Pd-catalyzed β-C—H arylation was noted and achieved. Rather than couple the free carboxylic acid and then amide couple, one could pre-synthesize amides derived from carboxylic acids and amino acids and take advantage of the presence of a bidentate directing group to run a more facile Pd-catalyzed arylation[15]. These results are shown in Table 2, below, and in FIG. 4A, FIG. 4B and FIG. 4C.

TABLE 2

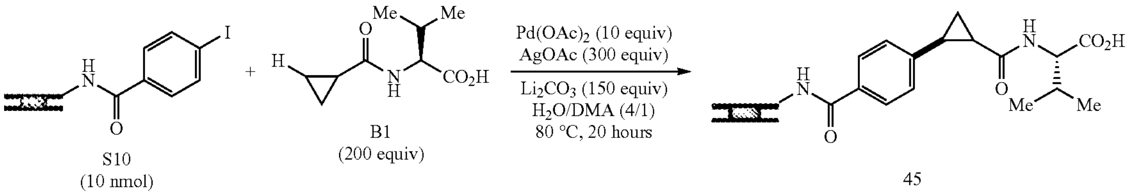

S10 (10 nmol) + B1 (200 equiv) → 45

| Entry | Deviation from standard condition | 45 (%) |
|---|---|---|
| 1 | none | 69 |
| 2 | without $Pd(OAc)_2$ | 0 |
| 3 | without AgOAc | 24 |
| 4 | without $Li_2CO_3$ | 35 |
| 5 | AgTFA instead of AgOAc | 46 |
| 6 | $Ag_2CO_3$ instead of AgOAc | 42 |
| 7 | NaOAc instead of $Li_2CO_3$ | 46 |
| 8 | $Na_2CO_3$ instead of $Li_2CO_3$ | 55 |
| 9 | $K_2CO_3$ instead of $Li_2CO_3$ | 41 |
| 10 | r.t. instead of 80° C. | 60 |

Reevaluation of the silver source, base, and co-solvents in the absence of ligand led to optimized conditions that afforded Compound 45 in 69% yield (entry 1, Table 2). Palladium is essential for this transformation (entry 2, Table 2). Silver salts and bases are not strictly required but have a significant impact on yield (entries 3 to 9, Table 2). Surprisingly, this reaction was also found to work well at room temperature (entry 10, Table 2).

Amides derived from cyclopropane- or cyclobutanecarboxylic acid and a broad range of α-amino acids reacted smoothly both heated and at room temperatures (Compounds 45 to 56) as is also seen in the yields shown in FIG. 4A. Pd-catalyzed arylation proceeds only at the β-C—H bond from the amide; attempted coupling of Ac-L-Val-OH gave none of arylation product Compound 59 indicating that α-arylation did not occur. Two LC peaks having same mass were due to the generation of diastereomers after the C—H arylation. To demonstrate this, a representative off-DNA reaction was run to synthesize product Compound 51. As expected, a mixture of diastereomers were observed, although the ratio is slightly lower due to different reaction temperature.

Although amides derived from α-amino acids and containing cyclopropyl or cyclobutyl rings (desirable as alkene isosteres) were focused upon, the chemistry can be extended to other alkyl carboxylic acids (Compounds 57 and 58) and to β-amino acids (Compound 60). Diverse arene substitution patterns on the DNA-tethered aryl iodide were tolerated (Compounds 61 to 65) as seen in the yields shown in FIG. 4B.

As was the case for β-C—H arylation of carboxylic acids, the DNA-tolerant conditions for amide arylation can also be employed for coupling DNA-tethered heteroaryl iodides such as pyridines and pyrazoles (Compounds 66 to 72). If desired, the carboxylic acid of the product can be further modified (Compound 73) shown in FIG. 4C.

Having developed DNA-compatible $C(sp^3)$-H arylations for carboxylic acids and amides, attention was turned to use of ketones in similar DNA-compatible $C(sp^3)$-H arylations. Ketones are useful monomers for building DELs because they can be further elaborated via reductive amination. Guided by previous work using aminooxyacetic acids as removable directing groups to recruit palladium to activate the β-C—H bond of ketones[16], a DNA-tolerant version of this reaction was created and optimized.

The optimized reaction illustrated in Table 3 and FIG. 5A through FIG. 5D gave arylation product Compound 83 in 62% yield (entry 1, Table 3, below). This reaction requires palladium and heat (entries 2 and 3, Table 3) and is strongly influenced by the silver salt (entries 4-6, Table 3); ligand and base play a lesser role (entries 7 and 8, Table 3). Ligand L8 was also found to decrease the degradation of DNA and provide cleaner LC traces. Although a large excess of palladium is often associated with degradation of the DNA tag, this chemistry gives a higher yield at 20 mM Pd/L (entry 1, 40 equivalents) than at 30 equivalents (entry 9, Table 3).

TABLE 3

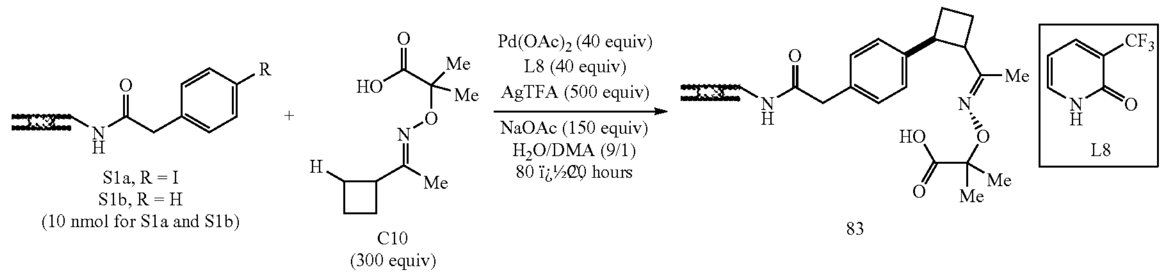

S1a, R = I
S1b, R = H
(10 nmol for S1a and S1b)

C10
(300 equiv)

83

L8

| Entry | Deviation from standard condition | 83 (%) |
|---|---|---|
| 1 | none | 62 |
| 2 | without $Pd(OAc)_2$ | 0 |
| 3 | r.t. instead of 80° C. | 0 |
| 4 | without AgTFA | 4 |
| 5 | $Ag_2CO_3$ (300 equiv) instead of AgTFA | 25 |
| 6 | AgOAc (500 equiv) instead of AgTFA | 32 |
| 7 | without L8 | 51 |
| 8 | without NaOAc | 55 |
| 9 | $Pd(OAc)_2$/L8 (30 equiv/30 equiv) | 49 |
| 10 | S1b instead of S1a | 0 |

The above conditions effect β-C—H arylation in diverse settings, including on acyclic ketone derivatives (Compounds 74 to 77, 84 to 89), at positions next to simple or complex rings (Compounds 78 to 82, 90, 91), and on simple or complex rings (Compounds 83, 92) as is seen by the yields shown in FIG. 5A. A broad range of functional groups are tolerated on the ketone to be arylated, including esters, ethers, acetals, and amides.

Ketone derivatives bearing β-quaternary centers can also be γ-arylated (Compound 93) as illustrated in FIG. 5A. The yields shown in FIG. 5B illustrate that DNA-tethered aryl iodide accepts different substitution patterns (Compounds 94 to 97) and heteroaryl iodides can react under the same conditions (Compounds 98 to 102).

The ability to convert the oxime ethers back into ketones is critical for implementing this chemistry in a DEL build. It was found that these oxime ethers readily hydrolyze in the presence of aniline and acetone (Compound 83 to 103), likely through equilibrium transamination with aniline and trapping of the free aminooxyacetic acid with acetonel[17]. This reaction is illustrated in FIG. 5C.

Each of these $C(sp^3)$-H activation reactions, as new disconnections for DEL synthesis, can incorporate unique structural motifs. The combination of multiple $C(sp^3)$-H activations in DEL synthesis can further enhance the diversity. Hence, a multi-step synthesis on DNA consisting of β-C—H arylation of a carboxylic acid, amide formation, β-C—H arylation of a masked ketone, and ketone deprotection was embarked upon to demonstrate how these C—H activation chemistries can be combined to develop large DELs of diverse, drug-like compounds. A representative analog synthesis is shown in FIG. 5D.

Thus, pyridyl iodide Compound S18 and pivalic acid were coupled to form intermediate Compound 31, and amide coupling with p-iodobenzyl amine then set up a second C—H arylation event. Coupling with a masked cyclobutyl ketone gave oxime ether Compound 105, whose hydrolysis revealed ketone Compound 106 with 6% overall yield over 4 steps as shown in FIG. 5E.

The above is only one of many sequences that a skilled worker can design by using sequential multiple C—H arylation steps in combination with common DNA-encoded library-building steps such as amide formation or reductive amination. Importantly, the ability to conduct the C—H arylations using DNA-tethered aryl iodides means that the full power split-pool combinatorial synthesis can be realized.

To evaluate DNA compatibility of the C—H activation chemistry with DEL synthesis, a select set of chemically modified on-DNA analogs (C—H arylation products 1, 45 and 83), along with their starting aryl iodide analog Sla were enzymatically ligated to a 65-mer dsDNA, so that the resulting oligomers were approximately equal in length to an encoding tag of a 3-cycle DEL build. All four ligation reactions proceeded smoothly, indicating that chemistry had no significant impact on encodability. In order to determine the amount of amplifiable DNA remaining after exposure to C—H activation conditions, the ligation products from 1, 45 and 83 were amplified by PCR and compared with those of Sla (untreated control). All three reactions showed satisfactory PCR viability (60-80% amplifiable DNA remaining). Moreover, Sanger sequencing reads also confirmed the integrity of their nucleobase sequence structures.

As purification is an inherently difficult process in split-pool synthesis, the reactivity required for DNA-compatible reactions must be devoid of unidentified byproducts that can complicate analysis. In this case, the main byproducts generated through our reaction platform consist only of starting material or its protodehalogenated derivative. Finally, we were able to obtain all products through our on-DNA C—H arylation platform in moderate and synthetically useful yields; higher than the threshold of 25% deemed practical in DEL synthesis.[10f] Gratifyingly also, we were able to obtain 60-80% DNA recovery from qPCR experiments, greater than the acceptable 30% threshold deemed practical in these processes.[4c] Altogether, these promising results further demonstrate the practicality of our DEL-compatible $C(sp^3)$-H activation platform, enabling practitioners to rapidly generate structural complexity and diversity in a modular manner.

In summary, DEL-compatible $C(sp^3)$-H activation reactions of carboxylic acid, amides, and ketones have been developed. Ligands were essential for the reactivity under DEL conditions. These protocols are compatible with $C(sp^3)$-H bond of small rings and heterocyclic coupling partners that are desirable for improving drug-like properties. Sequential $C(sp^3)$-H activation for DEL synthesis provides a unique tool for constructing chemical diversity containing high $C(sp^3)$ character.

1. General Information

Equipment and Chemicals

VWR® modular heating block (64 wells) was used to heat PCR tubes to run the DNA reactions. 10K variable speed mini centrifuge (BT604) was purchased from BTLab Systems. VWR® 9 mm screw-thread polypropylene vials and screw caps were used to submit the samples to HPLC-MS. Hexafluoroisopropanol (HFIP) was purchased from Oakwood. N,N-Dimethyl-acetamide (DMA) was obtained from Honeywell. N,N-dimethylformamide (DMF) and acetonitrile ($CH_3CN$) were obtained by passing the previously degassed solvents through an activated alumina column. Deionized water was used in all the reactions. $Pd(OAc)_2$ was purchased from Strem Chemicals, Inc. $Ag_2CO_3$, AgOAc, AgTFA and $Ag_3PO_4$ were obtained from Sigma-Aldrich. All other reagents were purchased at the highest commercial quality and used without further purification. Ligands were prepared via previously published protocols except some of them are now commercially available. The iodo-substituted heteroaromatic acids were received from Pfizer. Carboxylic acids, amides and ketones bearing directing groups were synthesized via previously published protocols except some are also commercially available. DMTMM=4-(4,6-dimethoxy-1,3,5-triazin-2-yl)-4-methylmorpholinium chloride.

DNA Headpiece Materials

DNA headpiece (5'-/5Phos/GAGTCA/iSp9/-iUniAmM/-iSp9/-TGACTCCC-3', below) was obtained from Biosearch Technologies, Petaluma, CA. The abbreviated DNA headpiece is shown below.

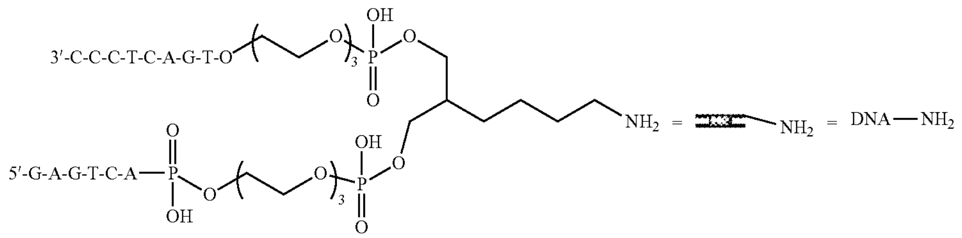
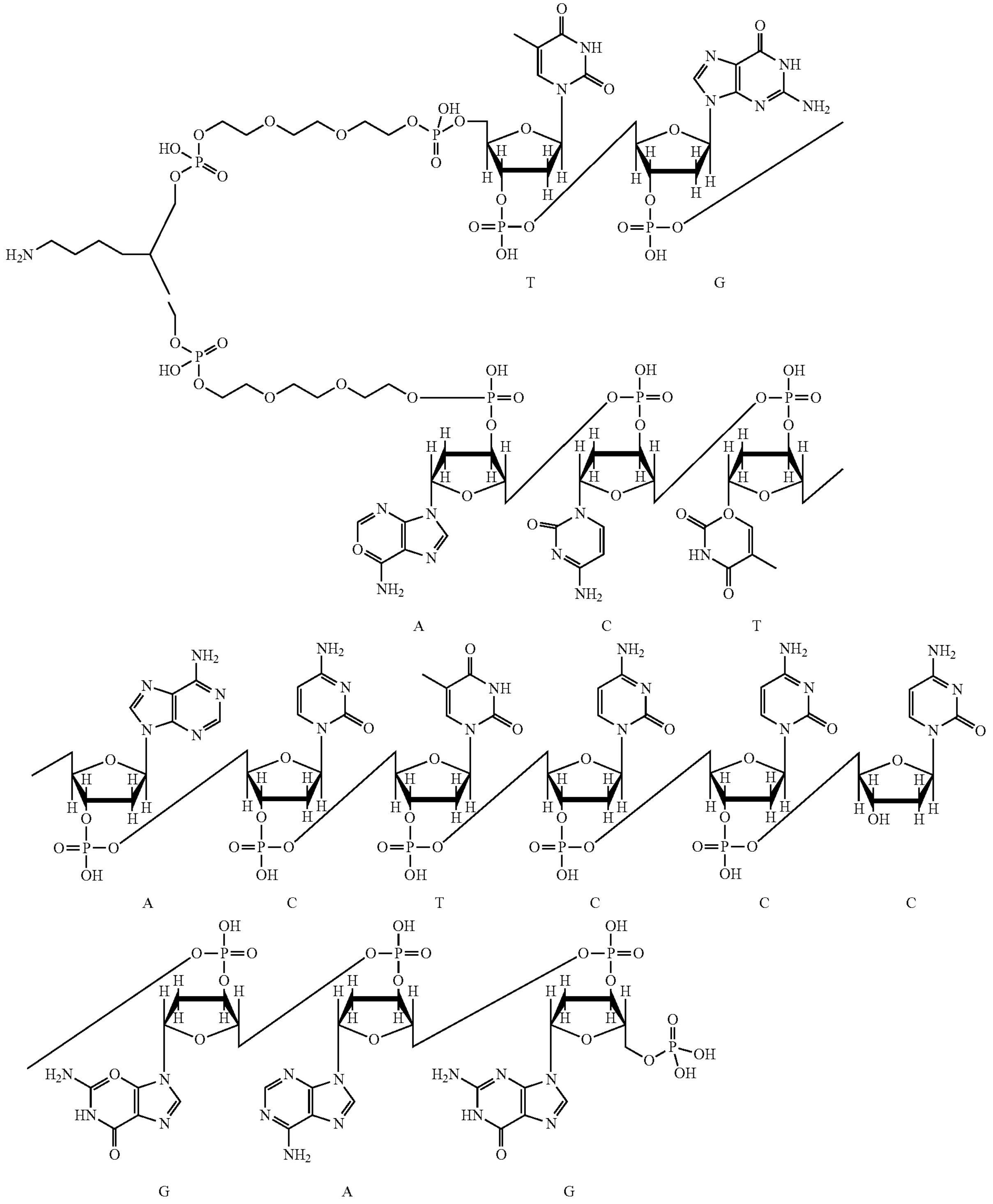

Analysis of DNA Samples

DNA Concentration:

DNA samples subjected to HPLC-MS analysis were prepared as 0.1 mM in $H_2O$, assuming 100% of DNA total recovery after reaction.

Analysis:

One microliter of the DNA solution was analyzed on a Waters I-Class LC with a Waters BEH C18 column (2.1×55 mm, 1.7 μm, 130 A) using a gradient of 114 mM HFIP and 14 mM $Et_3N$ in water (A) and methanol (B) (0.3 mL/minute, 10-26% B over 10 minutes) at 60° C. The yield was determined by calculating the percentage of UV absorbance at 260 nm corresponding to the product peak, ignoring potential UV absorption coefficient differences between DNA products and assuming 100% mass recovery. Peak identities were determined by ESI using the $[M]^{3-}$ ion.

Deconvolution:

Data visualization and integration was performed with MassLynx™ V4.1 software.

Yield Calculation:

Ignoring UV coefficient difference for all DNA products and assuming 100% of DNA total recovery, the yield of DNA products was determined from UV absorbance trace (260 nm) peak area using the equation below:

$$\text{Yield (product, \%)} = \frac{\%\ UV\ (\text{product})}{\%\ UV\ (DNA\ \text{starting material before reaction})} \times 100\%$$

MS Deconvolution:

Whereas multi-charged (negative) mass was observed, triply charged mass was determined to be base peak in all cases. Observed m/z could be calculated as m/z=[M]/z−1.00794.

2. Ligand Structures L1-L13

L1

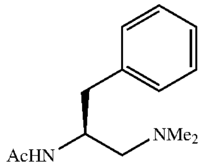

L2

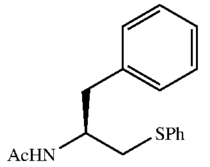

L3

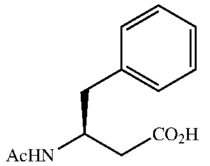

-continued

L4

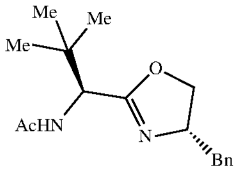

L5

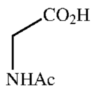

L6

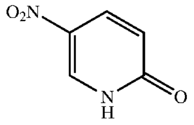

L7

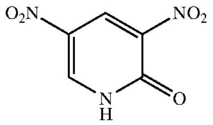

L8

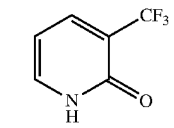

L9

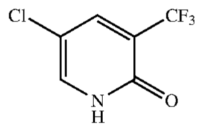

L10

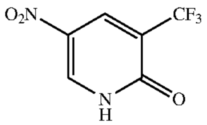

L11

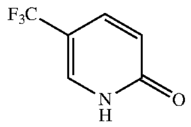

L12

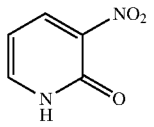

L13

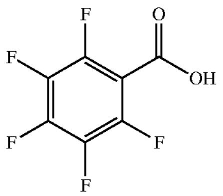

The Ligands L3, L5, L6-L13 were purchased from Sigma-Aldrich, Nova Biochem, TCI and Combi-Blocks Inc. The Ligands L1[14b], L2[18], L4[19] were synthesized according to previous reports.

3. Preparation of DNA-Conjugated Aryl Iodides

3.1 General Procedure 1 for DNA-Conjugated Aryl Iodides

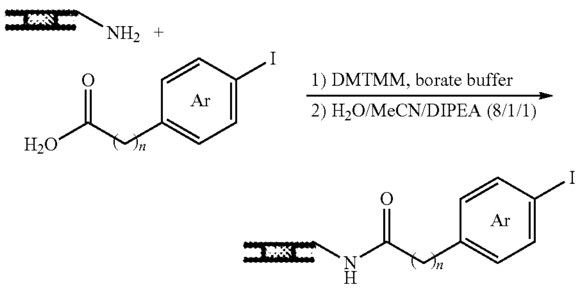

S

Materials

Headpiece: 20 mM in $H_2O$

Sodium carboxylate: 1.0 M in water [1 mmol acid was added into 1.0 mL aqueous NaOH (40 mg) solution]. 4-(4,6-Dimethoxy-1,3,5-triazin-2-yl)-4-methylmorpholinium chloride (DMTMM): 1.0 M in water (294.7 mg DMTMM dissolved in 1 mL $H_2O$)

Borate buffer: 100 mM in $H_2O$

General Procedure 1

1) To the headpiece solution (400 nmol, 20 μL), was added borate buffer solution (300 μL), sodium carboxylate (100 equiv, 40 μL) and DMTMM (100 equiv, 40 μL). The mixture was vortexed and maintained at room temperature for 3 hours.

2) To the mixture was added 5 M NaCl solution (40 μL) and cold ethanol (1.2 mL, ethanol stored at −20° C.). The mixture was then stored at −20° C. in a freezer for more than 30 minutes.

3) Centrifuge the sample for 7 minutes at 4° C. in a microcentrifuge at 10000 rpm. The supernatant was discarded and the precipitate was dried under vacuum. The pellet was then dissolved in deionized water (320 μL) and $CH_3CN$ (40 μL) followed by addition of N,N-diisopropylethylamine (DIPEA) (40 μL), and heated at 70° C. for 12 hours.

4) Cooling to room temperature, 5 M NaCl solution (40 μL) and cold ethanol (1.2 mL) were sequentially added, and the resultant mixture was stored at −20° C. for 30 minutes. The mixture was centrifuged at 4° C. for 7 minutes at 10000 rpm before the resulting supernatant was removed, and the precipitate was dried under vacuum. The pellet was dissolved in deionized water (40 μL, 10 mM), which was used in next study without further purification.

5) HPLC-MS analysis: 1 μL of this solution (10 mM) was transferred to a 200 μL microcentrifuge tube, diluted with 99 μL of $H_2O$ to prepare the testing sample at 0.1 mM concentration.

3.2 Structures of S1-S23

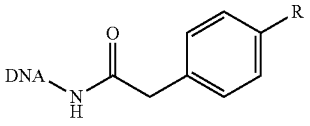

S1a, R = I
S1b, R = H

-continued

S2

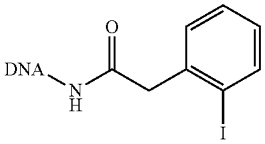

S3

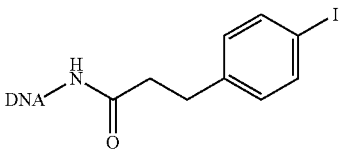

S4

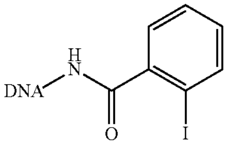

S5

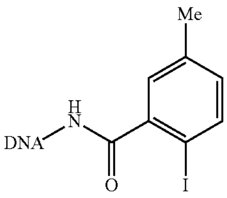

S6

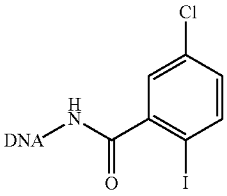

S7

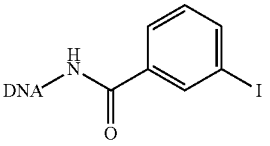

S8

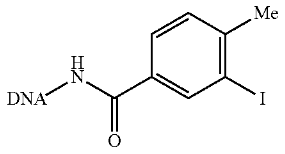

S9

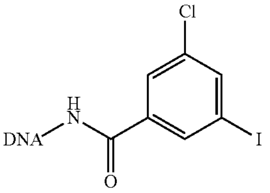

S10

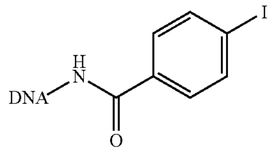

-continued

S11

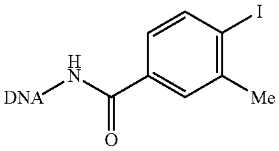

S12

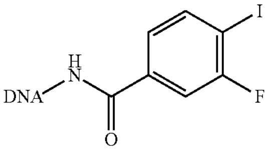

S13

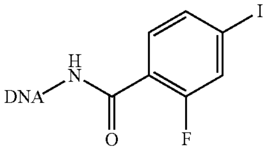

S14

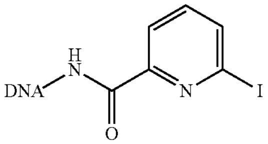

S15

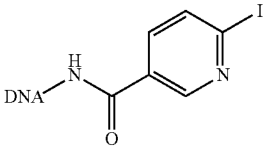

S16

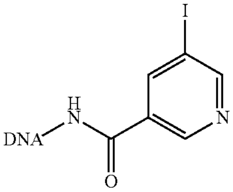

S17

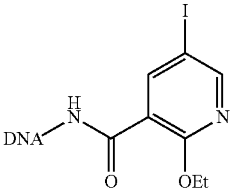

S18

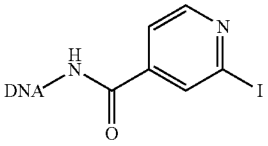

S19

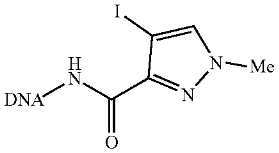

-continued

S20

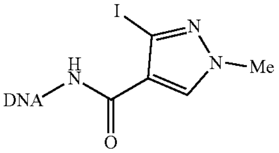

S21

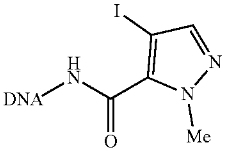

S22

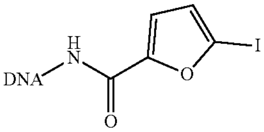

S23

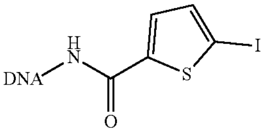

The iodo-substituted aromatic acids S1-S13 were purchased from Sigma-Aldrich, Oakwood, TCI and Combi-Blocks Inc. The heteroaromatic acids S14-S23 were received from Pfizer.

3.3 LC Trace and Mass Characterization of S1-S23

LC Trace and Mass of Sla

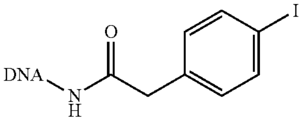

Following General Procedure 1

Yield: 85%

Exact mass: 5178.8211

Triply charged mass [M]/3-1.00794, calculated 1725.2658; observed 1725.2783.

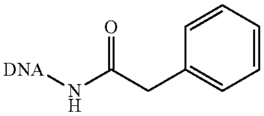

Following General Procedure 1.

Yield: 83%

Exact mass: 5052.9244

Triply charged mass [M]/3-1.00794, calculated 1683.3002; observed 1683.3007.

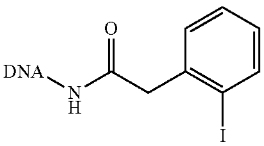

Following General Procedure 1.

Yield: 83%

Exact mass: 5178.8211

Triply charged mass [M]/3-1.00794, calculated 1725.2658; observed 1725.2783.

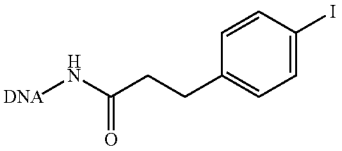

Following General Procedure 1.

Yield: 78%

Exact mass: 5192.8367

Triply charged mass [M]/3-1.00794, calculated 1729.9376; observed 1729.9423.

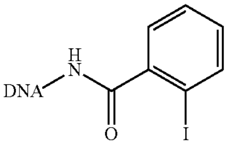

Following General Procedure 1.

Yield: 74%

Exact mass: 5164.8054

Triply charged mass [M]/3-1.00794, calculated 1720.5939; observed 1720.6038.

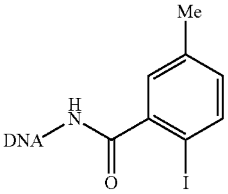

Following General Procedure 1.

Yield: 69%

Exact mass: 5178.8211

Triply charged mass [M]/3-1.00794, calculated 1725.2658; observed 1725.2783.

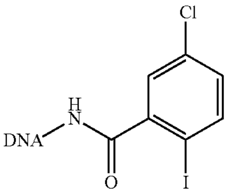

Following General Procedure 1.

Yield: 67%

Exact mass: 5198.7664

Triply charged mass [M]/3-1.00794, calculated 1731.9142; observed 1731.9187.

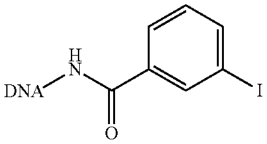

Following General Procedure 1.

Yield: 83%

Exact mass: 5164.8054

Triply charged mass [M]/3-1.00794, calculated 1720.5939; observed 1720.6038.

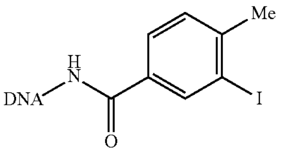

Following General Procedure 1.

Yield: 76%

Exact mass: 5178.8211

Triply charged mass [M]/3-1.00794, calculated 1725.2658; observed 1725.2783.

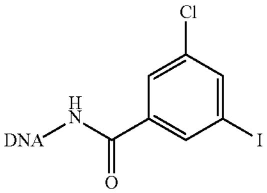

Following General Procedure 1.

Yield: 71%

Exact mass: 5198.7664

Triply charged mass [M]/3-1.00794, calculated 1731.9142; observed 1731.9187.

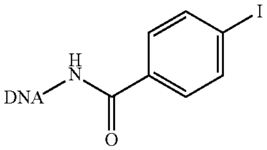

Following General Procedure 1.

Yield: 85%

Exact mass: 5164.8054

Triply charged mass [M]/3-1.00794, calculated 1720.5939; observed 1720.6038.

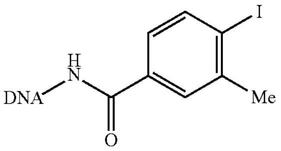

Following General Procedure 1.

Yield: 75%

Exact mass: 5178.8211

Triply charged mass [M]/3-1.00794, calculated 1725.2658; observed 1725.2783.

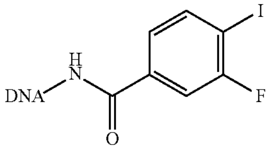

Following General Procedure 1.

Yield: 71%

Exact mass: 5182.7960

Triply charged mass [M]/3-1.00794, calculated 1726.5907; observed 1726.6053.

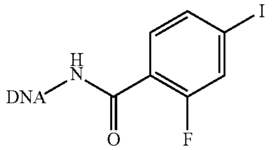

Following General Procedure 1.

Yield: 55%

Exact mass: 5182.7960

Triply charged mass [M]/3-1.00794, calculated 1726.5907; observed 1726.6053.

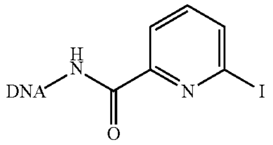

Following General Procedure 1.

Yield: 57%

Exact mass: 5165.8007

Triply charged mass [M]/3-1.00794, calculated 1720.9256; observed 1720.9265.

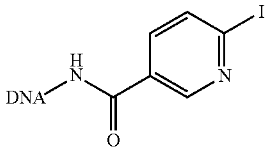

Following General Procedure 1.

Yield: 65%

Exact mass: 5165.8007

Triply charged mass [M]/3-1.00794, calculated 1720.9256; observed 1720.9265.

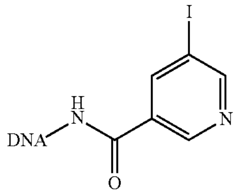

Following General Procedure 1.

Yield: 79%

Exact mass: 5165.8007

Triply charged mass [M]/3-1.00794, calculated 1720.9256; observed 1720.9265.

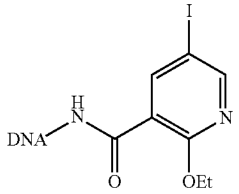

Following General Procedure 1.

Yield: 59%

Exact mass: 5209.8269

Triply charged mass [M]/3-1.00794, calculated 1735.6010; observed 1735.6018.

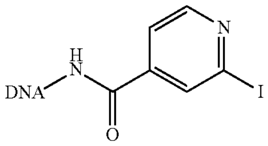

Following General Procedure 1.

Yield: 56%

Exact mass: 5165.8007

Triply charged mass [M]/3-1.00794, calculated 1720.9256; observed 1720.9265.

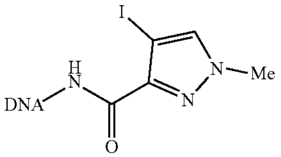

Following General Procedure 1.

Yield: 77%

Exact mass: 5168.8116

Triply charged mass [M]/3-1.00794, calculated 1721.9293; observed 1721.9290.

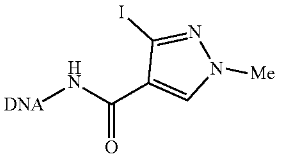

Following General Procedure 1.

Yield: 76%

Exact mass: 5168.8116

Triply charged mass [M]/3-1.00794, calculated 1721.9293; observed 1721.9459.

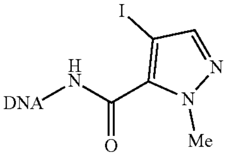

Following General Procedure 1.

Yield: 69%

Exact mass: 5168.8116

Triply charged mass [M]/3-1.00794, calculated 1721.9293; observed 1721.9290.

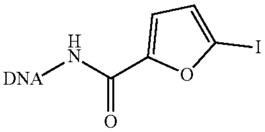

Following General Procedure 1.

Yield: 67%

Exact mass: 5154.7847

Triply charged mass [M]/3-1.00794, calculated 1717.2536; observed 1717.2589.

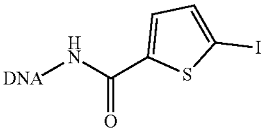

Following General Procedure 1.

Yield: 69%

Exact mass: 5170.7618

Triply charged mass [M]/3-1.00794, calculated 1722.5793; observed 1722.5918.

4. Experimental Section for on-DNA C—H Arylation of Free Carboxylic Acids

4.1 Substrate Structures of Free Carboxylic Acids A1-A38

A1

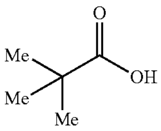

A2

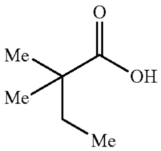

-continued

A3

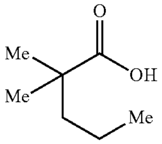

A4

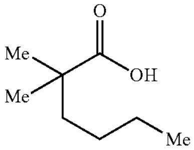

A5

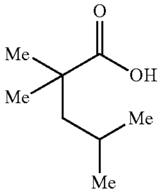

A6

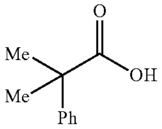

A7

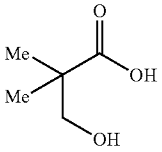

A8

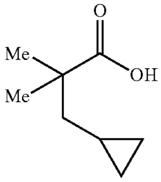

A9

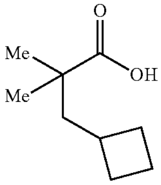

A10

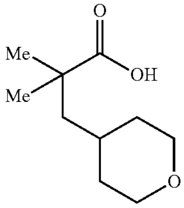

A11

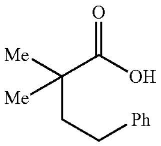

-continued
A12
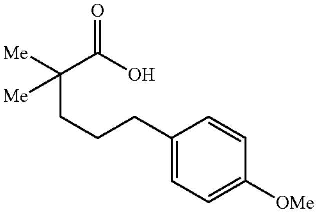
A13
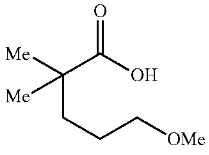
A14
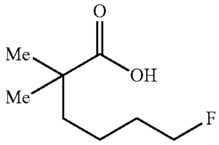
A15
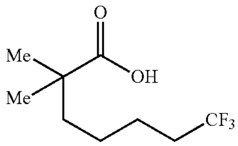
A16
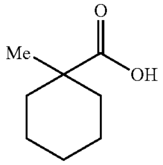
A17
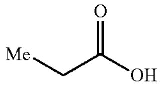
A18
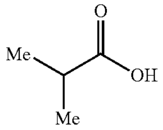
A19
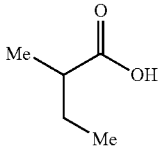
A20
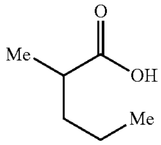
A21
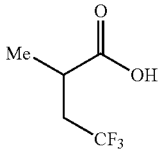
-continued
A22
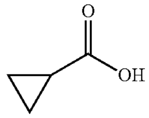
A23
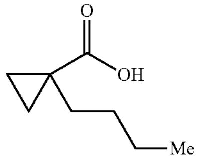
A24
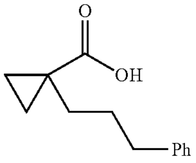
A25
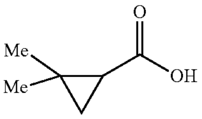
A26
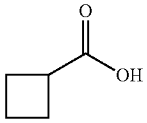
A27
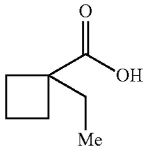
A28
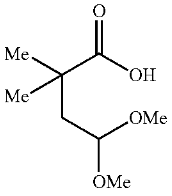
A29
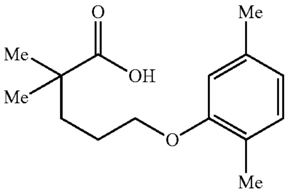
A30
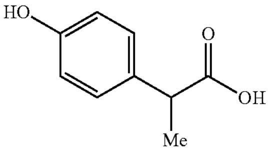
A31
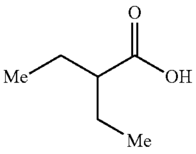

-continued
A32
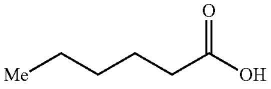
A33
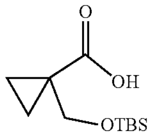
A34
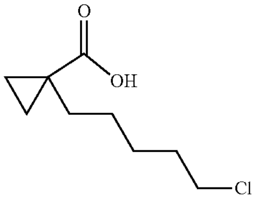
A35
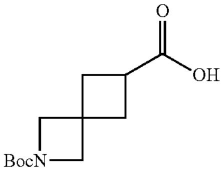
-continued
A36
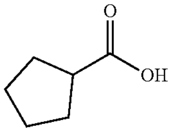
A37
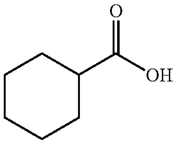
A38
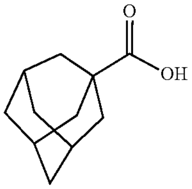
Carboxylic acids were obtained from the commercial sources or synthesized following the literature procedures.[14b,20]
4.2 Condition Optimizations
TABLE 4
Evaluation of A1 Concentration
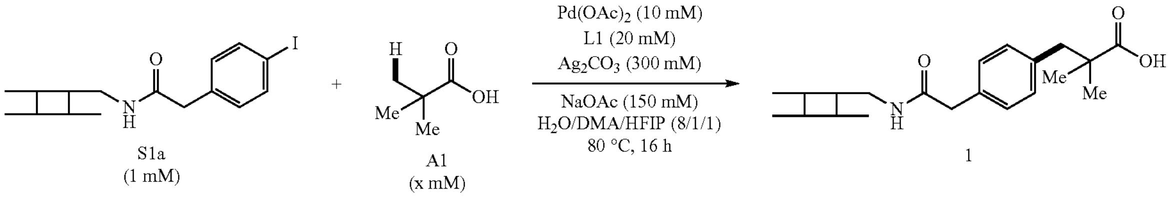
| Entry | A1 (x mM) | Yield (%) |
|---|---|---|
| 1 | 100 mM | 51 |
| 2 | 200 mM | 53 |
| 3 | 300 mM | 60 |
| 4 | 500 mM | 59 |
| 5 | 800 mM | 66 |
| 6 | 1000 mM | 78 |
| 7 | 2000 mM | 65 |
TABLE 5
Evaluation of Base
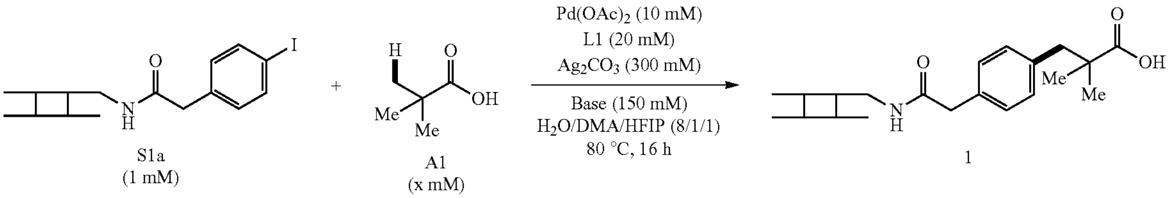
| Entry | Base (150 mM) | Yield (%) |
|---|---|---|
| 1 | NaOAc | 78 |
| 2 | KOAc | 49 |

TABLE 5-continued

| | | |
|---|---|---|
| 3 | $Na_2CO_3$ | 47 |
| 4 | $K_2CO_3$ | 65 |
| 5 | $NaHCO_3$ | 57 |
| 6 | $KHCO_3$ | 56 |
| 7 | $Na_2HPO_4$ | 57 |
| 8 | $NaH_2PO_4$ | 35 |
| 9 | $Na_3PO_4$ | 48 |
| 10 | $K_2HPO_4$ | 53 |
| 11 | $K_3PO_4$ | 59 |

TABLE 6

Evaluation of Pd/L Concentration

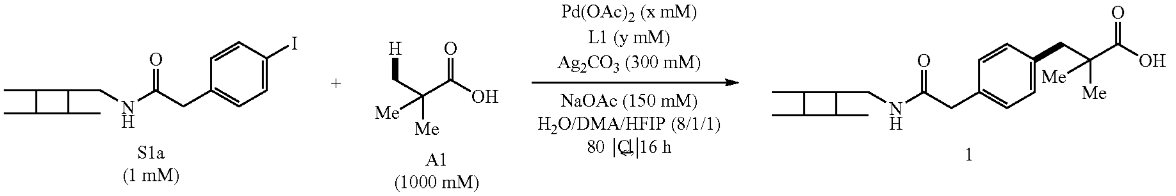

S1a (1 mM) + A1 (1000 mM) → 1

| Entry | Pd(OAc)$_2$/L1 (x/y) | Yield (%) |
|---|---|---|
| 1 | 10/10 | 67 |
| 2 | 10/15 | 72 |
| 3 | 10/20 | 78 |
| 4 | 10/30 | 49 |
| 5 | 10/40 | 52 |
| 6 | 5/20 | 42 |
| 7 | 15/20 | 60 |
| 8 | 20/20 | 65 |

TABLE 7

Evaluation of Standard Conditions

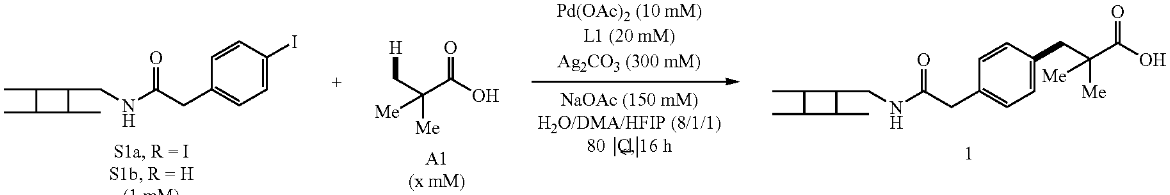

S1a, R = I
S1b, R = H
(1 mM)
+ A1 (x mM) → 1

| Entry | Deviation from above | Yield (%) |
|---|---|---|
| 1 | none | 78 |
| 2 | without Pd(OAc)$_2$ | 0 |
| 3 | without $Ag_2CO_3$ | 0 |
| 4 | without NaOAc | 77 |
| 5 | without L1 | 56 |
| 6 | $H_2O$/DMA (9/1) instead of $H_2O$/DMA/HFIP (8/1/1) | 76 |
| 7 | $H_2O$ instead of $H_2O$/DMA/HFIP (8/1/1) | 76 |
| 8 | r.t. instead of 80 °C | 0 |
| 9 | L2 instead of L1 | 74 |
| 10 | L3 instead of L1 | 66 |
| 11 | L4 instead of L1 | 65 |
| 12 | L5 instead of L1 | 54 |
| 13 | S1b instead of S1a | 0[a] |

[a]Only S1b was totally recovered.

4.3 DNA Recovery Investigations

TABLE 8

Evaluation of DNA Recovery

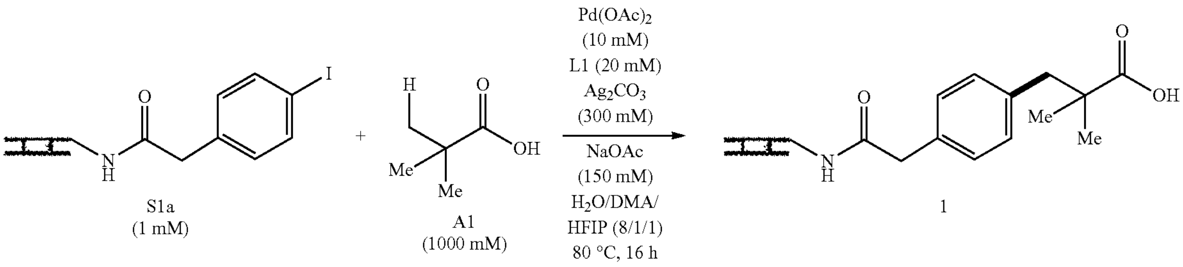

S1a (1 mM) + A1 (1000 mM) → 1

| Entry | Scavenger (sodium diethyldithiocarbamate trihydrate) | Total DNA Recovery (%)[a] |
|---|---|---|
| 1 | 10 equiv | 51 |
| 2 | 50 equiv | 76 |
| 3 | 70 equiv | 81 |
| 4 | 90 equiv | 85 |
| 5 | 100 equiv | 70 |

[a]The total DNA recovery was calculated with S1a as the standard.

4.4 General Procedure 2 for On-DNA C—H Arylation of Free Carboxylic Acids

Condition A:

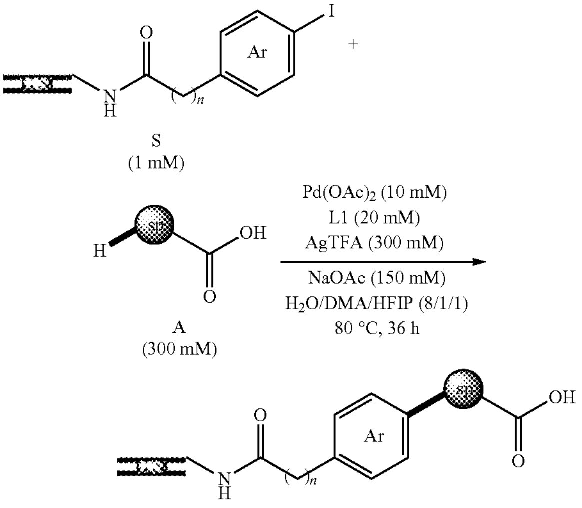

S (1 mM) + A (300 mM) → 1-51

Materials

DNA-conjugated aryl iodide S: 10 mM in $H_2O$ Carboxylic acid A: 3 M in DMA (Note: the high concentration may increase the total volume)

L1: 200 mM in hexafluoroisopropanol (HFIP) (4.4 mg in 100 μL HFIP)

$Pd(OAc)_2$: 100 mM in HFIP (2.2 mg in 100 μL HFIP)

NaOAc: 1.5 M in $H_2O$ (12.3 mg in 100 μL $H_2O$) Sodium diethyldithiocarbamate trihydrate (scavenger): 1 M in $H_2O$ (225.3 mg in 1.0 mL $H_2O$)

Procedure

1) To prepared AgTFA (300 equiv, 0.66 mg) was added $Pd(OAc)_2$ (10 equiv, 1 μL), after air-drying, carboxylic acid A (300 equiv, ca. 1.3 μL), DNA-conjugated aryl iodide S (10 nmol, 1 μL), NaOAc aqueous solution (150 equiv, 1 μL) and deionized water (6 μL) were added. Finally, L1 solution (20 equiv, 1 μL) was added. The mixture was vortexed, and the reaction mixture was heated at 80° C. for 36 hours.
2) The reaction mixture was cooled to room temperature, 9.0 μL scavenger was added, and the resulting mixture was reheated at 80° C. for 30 minutes.
3) The reaction mixture was cooled to room temperature, and 5 M NaCl solution (10% by volume, 1.9 μL) and cold ethanol (3 times by volume, 57 μL) were added. The mixture was stored at a −20° C. freezer for more than 30 minutes.
4) The sample was centrifuged for about 7 minutes in a microcentrifuge at 10000 rpm. The supernatant was discarded and the precipitate was dried under vacuum. The resulting DNA pellet was redissolved in $H_2O$ (100 μL) and centrifuged for about 2 minutes in a microcentrifuge at 10000 rpm. An aliquot (50 μL) was taken and analyzed via HPLC-MS.

Condition B:

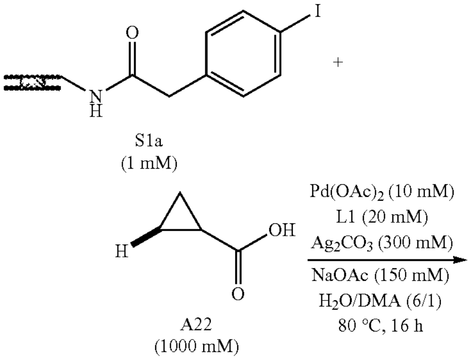

S1a (1 mM) + A22 (1000 mM)

-continued

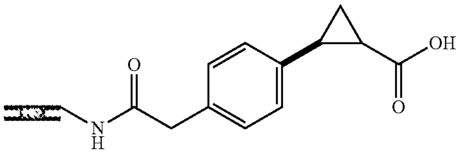

17

Materials

Sla: 10 mM in $H_2O$

Cyclopropanecarboxylic acid (A22): 3 M in $H_2O$

L1: 200 mM in HFIP $Pd(OAc)_2$: 100 mM in HFIP

NaOAc: 1.5 M in $H_2O$ (12.3 mg in 100 μL $H_2O$)

Sodium diethyldithiocarbamate trihydrate (scavenger): 1 M in $H_2O$

Procedure

1) To a 200 μL microcentrifuge tube was added $Pd(OAc)_2$ (10 equiv, 1 μL) and L1 solution (20 equiv, 1 μL). After air-drying, $Ag_2CO_3$ (300 equiv, 0.83 mg) was added, and then A22 (1000 equiv, 3.3 μL), Sla (10 nmol, 1 μL), NaOAc aqueous solution (150 equiv, 1 μL), DMA (1.4 μL) and deionized water (3.3 μL) were sequentially added. The mixture was vortexed. The reaction mixture was heated at 80° C. for 16 hours.

2) The reaction mixture was cooled to room temperature, 9.0 μL scavenger was added, and the resulting mixture was reheated at 80° C. for 30 minutes.

3) The reaction mixture was cooled to room temperature, and 5 M NaCl solution (10% by volume, 1.9 μL) and cold ethanol (3 times by volume, 57 μL) were added. The mixture was stored at −20° C. in a freezer for more than 30 minutes.

4) The sample was centrifuged for about 7 minutes in a microcentrifuge at 10000 rpm. The supernatant was discarded and the precipitate was dried under vacuum. The resulting DNA pellet was redissolved in $H_2O$ (100 μL) and centrifuged for about 2 minutes in a microcentrifuge at 10000 rpm. An aliquot (50 μL) was taken and analyzed via HPLC-MS.

4.5 Scope and Limitations of Free Carboxylic Acids

TABLE 9

Scope and Limitations of Free Carboxylic Acids

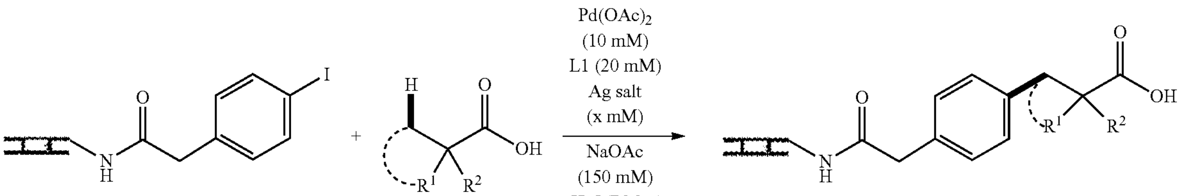

S1a (1 mM)

A (300 mM)

| Entry | Free Carboxylic Acid | Ag Salt (x mM) | Yield (%) |
|---|---|---|---|
| 1 | 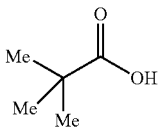 A1 | AgTFA (300 mM) | 31 |
| 2 | | $Ag_2CO_3$ (300 mM) | 60 |
| 3 | | $Ag_3PO_4$ (200 mM) | N.D. |
| 4 | | AgOAc (300 mM) | 61 |
| 5 | 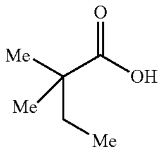 A2 | AgTFA (300 mM) | 46 |
| 6 | | $Ag_2CO_3$ (300 mM) | 49 (62)[a] |
| 7 | | $Ag_3PO_4$ (200 mM) | 5 |
| 8 | | AgOAc (300 mM) | 22 |
| 9 | 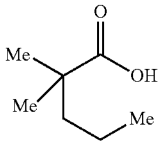 A3 | AgTFA (300 mM) | 72 |
| 10 | | $Ag_2CO_3$ (300 mM) | 24 |
| 11 | | $Ag_3PO_4$ (200 mM) | 8 |
| 12 | | AgOAc (300 mM) | 39 |

TABLE 9-continued
Scope and Limitations of Free Carboxylic Acids
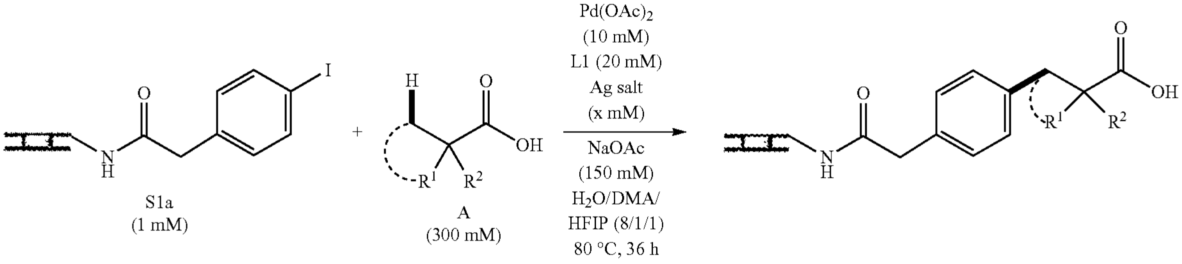
| Entry | Free Carboxylic Acid | Ag Salt (x mM) | Yield (%) |
|---|---|---|---|
| 13 | 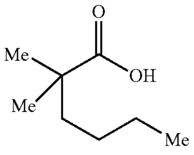 A4 | AgTFA (300 mM) | 56 |
| 14 | | $Ag_2CO_3$ (300 mM) | 9 |
| 15 | | $Ag_3PO_4$ (200 mM) | 8 |
| 16 | | AgOAc (300 mM) | 20 |
| 17 | 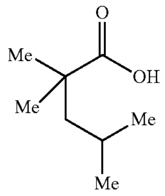 A5 | AgTFA (300 mM) | 48 |
| 18 | | $Ag_2CO_3$ (300 mM) | 11 |
| 19 | | $Ag_3PO_4$ (200 mM) | 7 |
| 20 | | AgOAc (300 mM) | 35 |
| 21 | 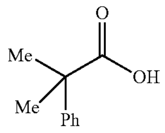 A6 | AgTFA (300 mM) | 32 |
| 22 | | $Ag_2CO_3$ (300 mM) | 11 |
| 23 | | $Ag_3PO_4$ (200 mM) | 18 |
| 24 | | AgOAc (300 mM) | 20 |
| 25 | 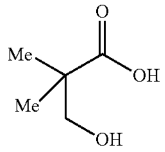 A7 | AgTFA (300 mM) | 19 |
| 26 | | $Ag_2CO_3$ (300 mM) | 12 |
| 27 | | $Ag_3PO_4$ (200 mM) | N.D. |
| 28 | | AgOAc (300 mM) | 18 |
| 29 | 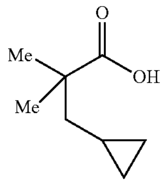 A8 | AgTFA (300 mM) | 33 |
| 30 | | $Ag_2CO_3$ (300 mM) | 29 |
| 31 | | $Ag_3PO_4$ (200 mM) | 21 |
| 32 | | AgOAc (300 mM) | 33 |
| 33 | 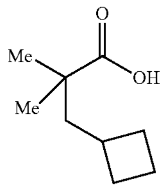 | AgTFA (300 mM) | 46 |
| 34 | | $Ag_2CO_3$ (300 mM) | 11 |
| 35 | | $Ag_3PO_4$ (200 mM) | 6 |
| 36 | | AgOAc (300 mM) | 13 |

TABLE 9-continued
Scope and Limitations of Free Carboxylic Acids
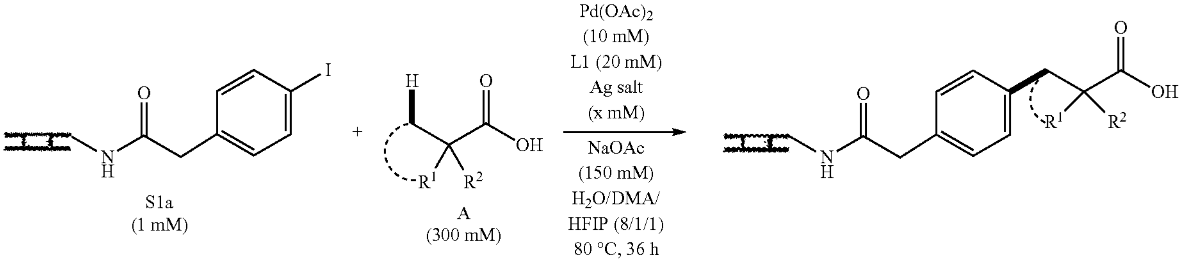
| Entry | Free Carboxylic Acid | Ag Salt (x mM) | Yield (%) |
|---|---|---|---|
| | A9 | | |
| 37 | 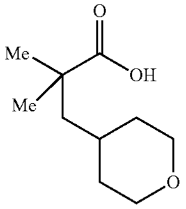 | AgTFA (300 mM) | 72 |
| 38 | | $Ag_2CO_3$ (300 mM) | 58 |
| 39 | | $Ag_3PO_4$ (200 mM) | 6 |
| 40 | | AgOAc (300 mM) | 20 |
| | A10 | | |
| 41 | 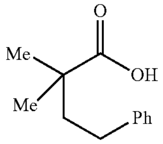 | AgTFA (300 mM) | 48 |
| 42 | | $Ag_2CO_3$ (300 mM) | 12 |
| 43 | | $Ag_3PO_4$ (200 mM) | 6 |
| 44 | | AgOAc (300 mM) | 16 |
| | A11 | | |
| 45 | 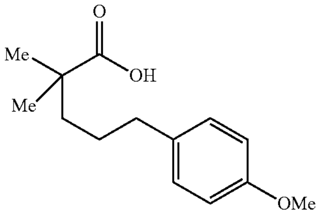 | AgTFA (300 mM) | 46 |
| 46 | | $Ag_2CO_3$ (300 mM) | 4 |
| 47 | | $Ag_3PO_4$ (200 mM) | 4 |
| 48 | | AgOAc (300 mM) | 14 |
| | A12 | | |
| 49 | 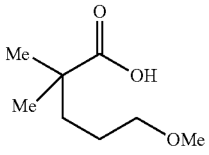 | AgTFA (300 mM) | 61 |
| 50 | | $Ag_2CO_3$ (300 mM) | 20 |
| 51 | | $Ag_3PO_4$ (200 mM) | N.D. |
| 52 | | AgOAc (300 mM) | 33 |
| | A13 | | |
| 53 | 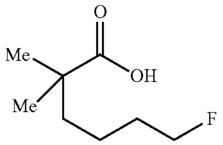 | AgTFA (300 mM) | 64 |
| 54 | | $Ag_2CO_3$ (300 mM) | 39 |
| 55 | | $Ag_3PO_4$ (200 mM) | 7 |
| 56 | | AgOAc (300 mM) | 35 |
| | A14 | | |

TABLE 9-continued
Scope and Limitations of Free Carboxylic Acids
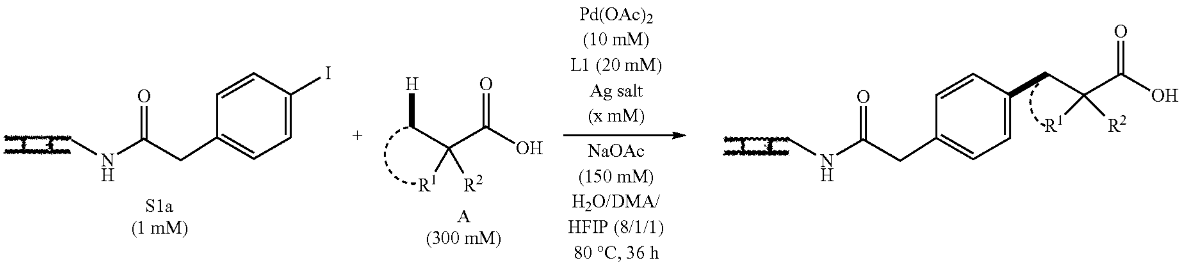
| Entry | Free Carboxylic Acid | Ag Salt (x mM) | Yield (%) |
|---|---|---|---|
| 57 | 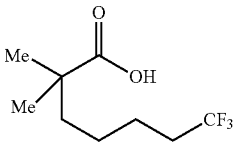 A15 | AgTFA (300 mM) | 49 |
| 58 | | $Ag_2CO_3$ (300 mM) | 4 |
| 59 | | $Ag_3PO_4$ (200 mM) | trace |
| 60 | | AgOAc (300 mM) | 5 |
| 61 | 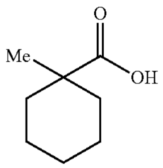 A16 | AgTFA (300 mM) | 61 |
| 62 | | $Ag_2CO_3$ (300 mM) | 8 |
| 63 | | $Ag_3PO_4$ (200 mM) | N.D. |
| 64 | | AgOAc (300 mM) | 11 |
| 65 | 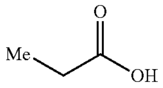 A17 | AgTFA (300 mM) | 5 |
| 66 | | $Ag_2CO_3$ (300 mM) | 21 |
| 67 | | $Ag_3PO_4$ (200 mM) | 28 |
| 68 | | AgOAc (300 mM) | 22 |
| 69 | 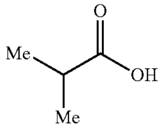 A18 | AgTFA (300 mM) | 16 |
| 70 | | $Ag_2CO_3$ (300 mM) | 28 |
| 71 | | $Ag_3PO_4$ (200 mM) | 16 |
| 72 | | AgOAc (300 mM) | 14 |
| 73 | 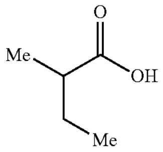 A19 | AgTFA (300 mM) | trace |
| 74 | | $Ag_2CO_3$ (300 mM) | 21 |
| 75 | | $Ag_3PO_4$ (200 mM) | 18 |
| 76 | | AgOAc (300 mM) | 28 |
| 77 | 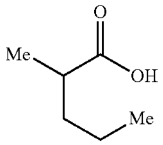 A20 | AgTFA (300 mM) | 13 |
| 78 | | $Ag_2CO_3$ (300 mM) | 4 |
| 79 | | $Ag_3PO_4$ (200 mM) | N.D. |
| 80 | | AgOAc (300 mM) | 24 |

TABLE 9-continued
Scope and Limitations of Free Carboxylic Acids
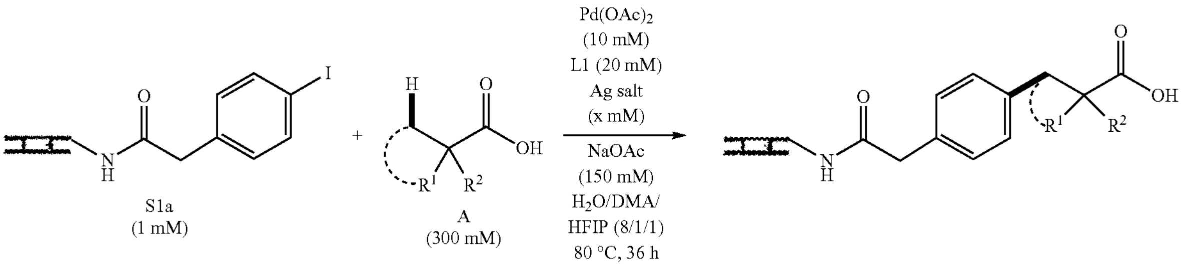
| Entry | Free Carboxylic Acid | Ag Salt (x mM) | Yield (%) |
|---|---|---|---|
| 81 | 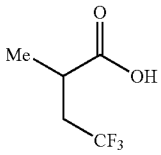 A21 | AgTFA (300 mM) | 18 |
| 82 | | $Ag_2CO_3$ (300 mM) | 12 |
| 83 | | $Ag_3PO_4$ (200 mM) | N.D. |
| 84 | | AgOTf (300 mM) | 26 |
| 85 | 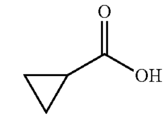 A22 | AgTFA (300 mM) | 12 |
| 86 | | $Ag_2CO_3$ (300 mM) | 22 (41)[b] |
| 87 | | $Ag_3PO_4$ (200 mM) | 16 |
| 88 | | AgOAc (300 mM) | 14 |
| 89 | 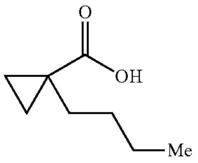 A23 | AgTFA (300 mM) | 47 |
| 90 | | $Ag_2CO_3$ (300 mM) | 6 |
| 91 | | $Ag_3PO_4$ (200 mM) | N.D. |
| 92 | | AgOAc (300 mM) | 12 |
| 93 | 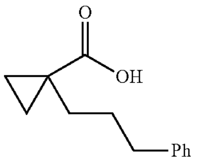 A24 | AgTFA (300 mM) | 40 |
| 94 | | $Ag_2CO_3$ (300 mM) | N.D. |
| 95 | 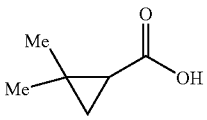 A25 | AgTFA (300 mM) | 7 |
| 96 | | $Ag_2CO_3$ (300 mM) | 21 |
| 97 | | $Ag_3PO_4$ (200 mM) | 6 |
| 98 | | AgOAc (300 mM) | 5 |
| 99 | 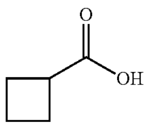 A26 | AgTFA (300 mM) | 20 |
| 100 | | $Ag_2CO_3$ (300 mM) | 16 (39)[c] |
| 101 | | $Ag_3PO_4$ (200 mM) | 16 |
| 102 | | AgOAc (300 mM) | 19 |

TABLE 9-continued
Scope and Limitations of Free Carboxylic Acids
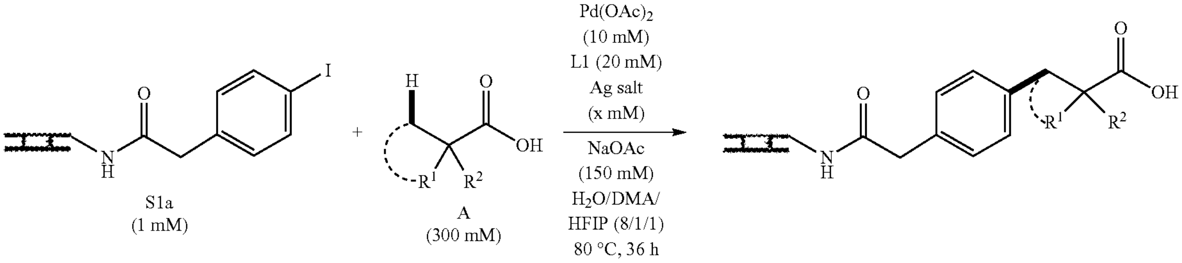
| Entry | Free Carboxylic Acid | Ag Salt (x mM) | Yield (%) |
|---|---|---|---|
| 103 | 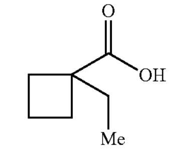 A27 | AgTFA (300 mM) | 34 |
| 104 | | $Ag_2CO_3$ (300 mM) | 40 |
| 105 | | $Ag_3PO_4$ (200 mM) | 24 |
| 106 | | AgOAc (300 mM) | 25 |
| 107 | 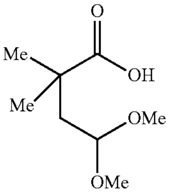 A28 | AgTFA (300 mM) | N.D. |
| 108 | 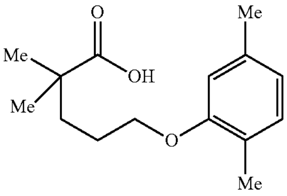 A29 | AgTFA (300 mM) | N.D. |
| 109 | | $Ag_2CO_3$ (300 mM) | N.D. |
| 110 | 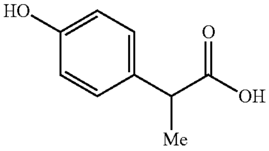 A30 | AgTFA (300 mM) | N.D. |
| 111 | | $Ag_2CO_3$ (300 mM) | Trace |
| 112 | 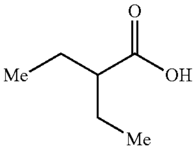 A31 | AgTFA (300 mM) | N.D. |
| 113 | 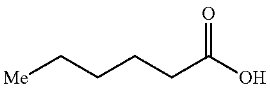 A32 | AgTFA (300 mM) | N.D. |

TABLE 9-continued
Scope and Limitations of Free Carboxylic Acids
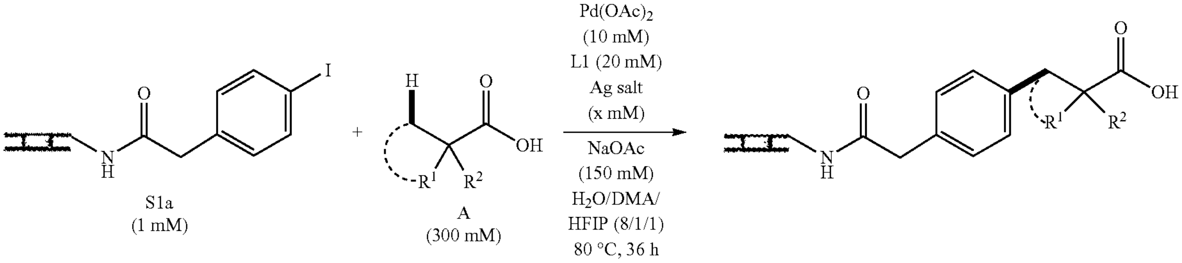
| Entry | Free Carboxylic Acid | Ag Salt (x mM) | Yield (%) |
|---|---|---|---|
| 114<br>115 | 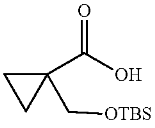 [SMILES: CC(C)(C)[Si](C)(C)OCC1(C(=O)O)CC1]<br>A33 | AgTFA (300 mM)<br>$Ag_2CO_3$ (300 mM) | N.D.<br>N.D. |
| 116<br>117 | 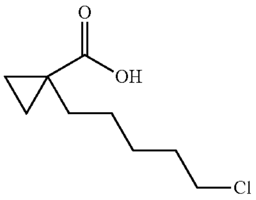 [SMILES: O=C(O)C1(CCCCCCl)CC1]<br>A34 | AgTFA (300 mM)<br>$Ag_2CO_3$ (300 mM) | N.D.<br>N.D. |
| 118 | 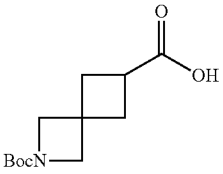<br>A35 | AgTFA (300 mM) | N.D. |
| 119 | 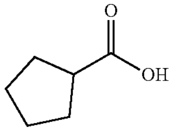<br>A36 | AgTFA (300 mM) | N.D. |
| 120 | 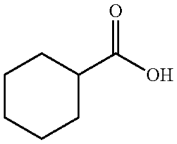<br>A37 | AgTFA (300 mM) | N.D. |
| 121 | 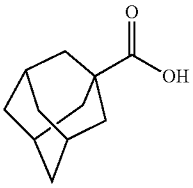 [SMILES: O=C(O)C12CC3CC(CC(C3)C1)C2]<br>A38 | AgTFA (300 mM) | N.D. |

TABLE 9-continued

Scope and Limitations of Free Carboxylic Acids

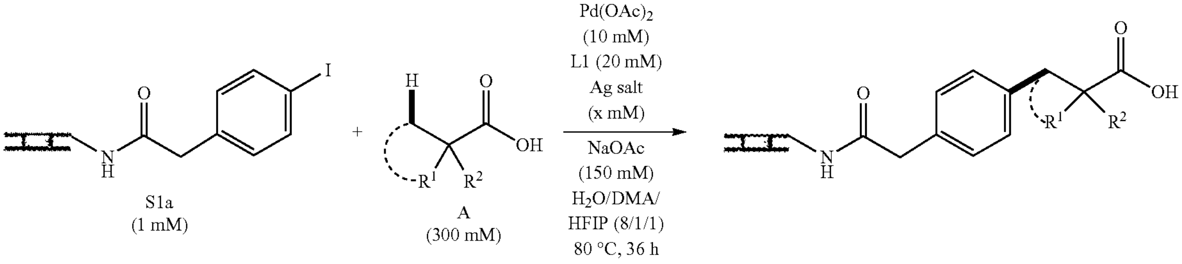

| Entry | Free Carboxylic Acid | Ag Salt (x mM) | Yield (%) |
|---|---|---|---|

[a]Using A2 (500 mM);
[b]Condition B was followed;
[c]Using A26 (1000 mM), 16 hours.
N.D. = not detected.

4.6 LC Trace and Mass Characterization of 1-51

LC Trace and Mass of 1

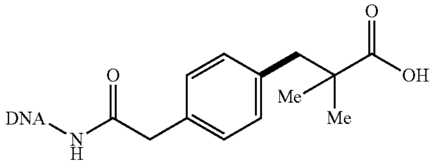

Following General Procedure 2 (Condition A) with A1 (1000 mM) except for employing $Ag_2CO_3$ instead of AgTFA.

Yield: $\frac{66}{85}\times 100\% = 78\%$

Ratio (product/deiodination/aryl iodide): 66/2/4

Exact mass: 5152.9766

Triply charged mass [M]/3-1.00794, calculated 1716.6509; observed 1716.6649.

LC Trace and Mass of 2

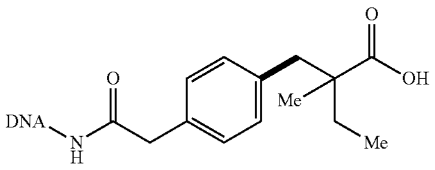

Following General Procedure 2 (Condition A) with A2 (500 mM) except for employing $Ag_2CO_3$ instead of AgTFA.

Yield: $\frac{53}{85}\times 100\% = 62\%$

Ratio (product/deiodination/aryl iodide): 53/6/24

Exact mass: 5166.9927

Triply charged mass [M]/3-1.00794, calculated 1721.3230; observed 1721.3342.

LC Trace and Mass of 3

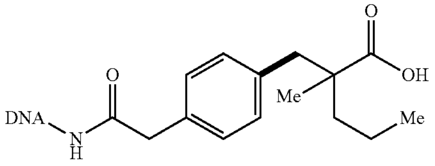

Following General Procedure 2 (Condition A) with A3.

Yield: $\frac{61}{85}\times 100\% = 72\%$

Ratio (product/deiodination/aryl iodide): 61/3/4

Exact mass: 5181.0081

Triply charged mass [M]/3-1.00794, calculated 1725.9948; observed 1725.9928.

LC Trace and Mass of 4

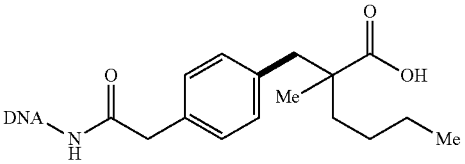

Following General Procedure 2 (Condition A) with A4.

Yield: $\frac{48}{85}\times 100\% = 56\%$

Ratio (product/deiodination/aryl iodide): 48/5/6

Exact mass: 5195.0238

Triply charged mass [M]/3-1.00794, calculated 1730.6667; observed 1730.6748.

LC Trace and Mass of 5

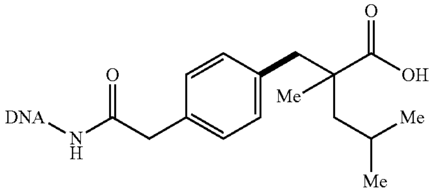

Following General Procedure 2 (Condition A) with A5.

Yield: 41/85×100%=48%

Ratio (product/deiodination/aryl iodide): 41/10/18

Exact mass: 5195.0238

Triply charged mass [M]/3-1.00794, calculated 1730.6667; observed 1730.6748.

LC Trace and Mass of 6

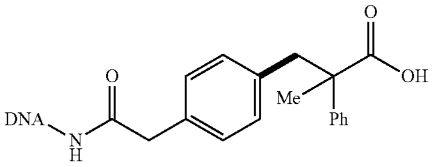

Following General Procedure 2 (Condition A) with A6.

Yield: 27/85×100%=32%

Ratio (product/deiodination/aryl iodide): 27/12/10

Exact mass: 5214.9925

Triply charged mass [M]/3-1.00794, calculated 1737.3229; observed 1737.3254.

LC Trace and Mass of 7

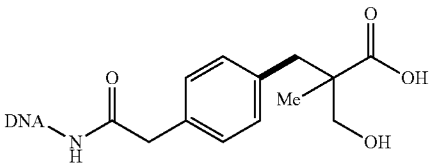

Following General Procedure 2 (Condition A) with A7.

Yield: 16/85×100%=19%

Ratio (product/deiodination/aryl iodide): 16/4/5

Exact mass: 5168.9718

Triply charged mass [M]/3-1.00794, calculated 1721.9827; observed 1721.9800.

LC Trace and Mass of 8

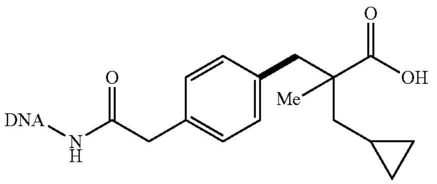

Following General Procedure 2 (Condition A) with A8.

Yield: 28/85×100%=33%

Ratio (product/deiodination/aryl iodide): 28/3/11

Exact mass: 5193.0081

Triply charged mass [M]/3-1.00794, calculated 1729.9948; observed 1729.9934.

LC Trace and Mass of 7

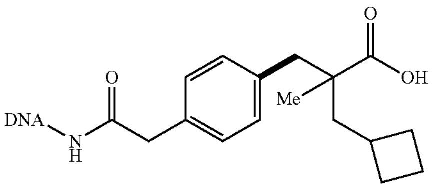

Following General Procedure 2 (Condition A) with A9.

Yield: 39/85×100%=46%

Ratio (product/deiodination/aryl iodide): 39/4/6

Exact mass: 5207.0238

Triply charged mass [M]/3-1.00794, calculated 1734.6667; observed 1734.6637.

LC Trace and Mass of 8

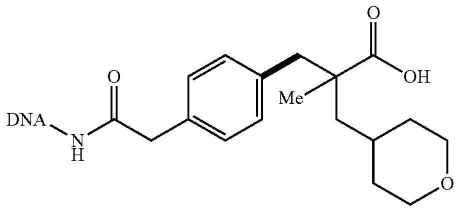

Following General Procedure 2 (Condition A) with A10.

Yield: 61/85×100%=72%

Ratio (product/deiodination/aryl iodide): 61/5/0

Exact mass: 5237.0344

Triply charged mass [M]/3-1.00794, calculated 1744.6702; observed 1744.6731.

LC Trace and Mass of 9

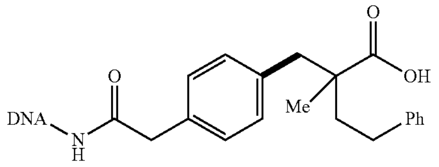

Following General Procedure 2 (Condition A) with A11.

Yield: 41/85×100%=48%

Ratio (product/deiodination/aryl iodide): 41/11/3

Exact mass: 5243.0238

Triply charged mass [M]/3-1.00794, calculated 1746.6667; observed 1746.6749.

LC Trace and Mass of 10

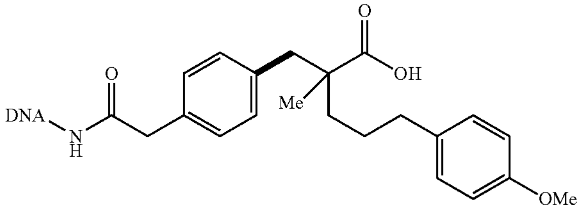

Following General Procedure 2 (Condition A) with A12.

Yield: 39/85×100%=46%

Ratio (product/deiodination/aryl iodide): 39/9/4

Exact mass: 5287.0500

Triply charged mass [M]/3-1.00794, calculated 1761.3421; observed 1761.3392.

LC Trace and Mass of 11

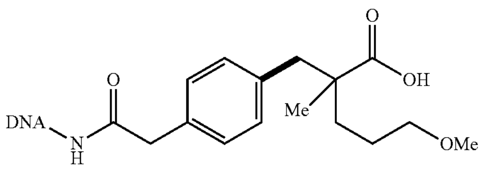

Following General Procedure 2 (Condition A) with A13.

Yield: 52/85×100%=61%

Ratio (product/deiodination/aryl iodide): 52/4/5

Exact mass: 5211.0187

Triply charged mass [M]/3-1.00794, calculated 1735.9983; observed 1736.0114.

LC Trace and Mass of 12

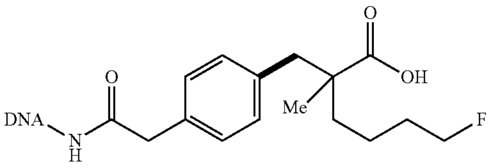

Following General Procedure 2 (Condition A) with A14.

Yield: 54/85×100%=64%

Ratio (product/deiodination/aryl iodide): 54/2/10

Exact mass: 5213.0144

Triply charged mass [M]/3-1.00794, calculated 1736.6635; observed 1736.6769.

LC Trace and Mass of 13

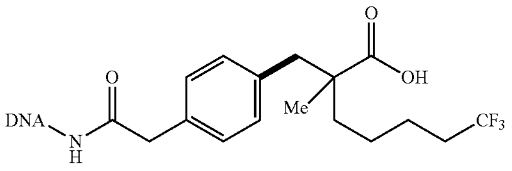

Following General Procedure 2 (Condition A) with A15.

Yield: 42/85×100%=49%

Ratio (product/deiodination/aryl iodide): 42/5/6

Exact mass: 5263.0112

Triply charged mass [M]/3-1.00794, calculated 1753.3291; observed 1753.3391.

LC Trace and Mass of 14

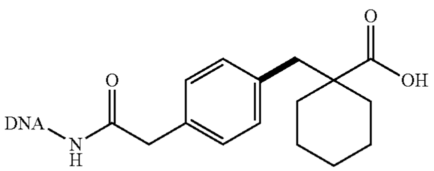

Following General Procedure 2 (Condition A) with A16.

Yield: 52/85×100%=61%

Ratio (product/deiodination/aryl iodide): 52/3/12

Exact mass: 5193.0081

Triply charged mass [M]/3-1.00794, calculated 1729.9948; observed 1730.0104.

LC Trace and Mass of 15

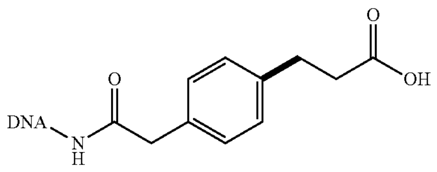

Following General Procedure 2 (Condition A) with A17 except for employing $Ag_3PO_4$ instead of AgTFA.

Yield: 24/85×100%=28%

Ratio (product/deiodination/aryl iodide): 24/7/5

Exact mass: 5124.9455

Triply charged mass [M]/3-1.00794, calculated 1707.3072; observed 1707.3116.

LC Trace and Mass

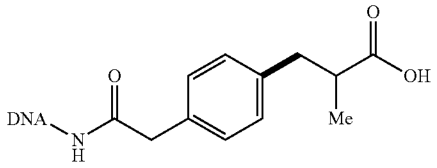

Following General Procedure 2 (Condition A) with A18 except for employing $Ag_2CO_3$ instead of AgTFA.

Yield: 24/85×100%=28%

Ratio (product/deiodination/aryl iodide): 24/6/6

Exact mass: 5138.9612

Triply charged mass [M]/3-1.00794, calculated 1711.9791; observed 1711.9851.

LC Trace and Mass

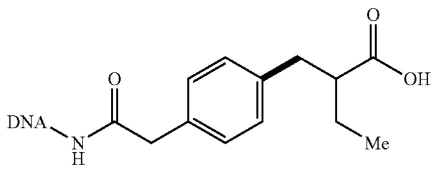

Following General Procedure 2 (Condition A) with A19 except for employing AgOAc instead of AgTFA.

Yield: 24/85×100%=28%

Ratio (product/deiodination/aryl iodide): 24/17/3

Exact mass: 5152.9768

Triply charged mass [M]/3-1.00794, calculated 1716.6510; observed 1716.6649.

LC Trace and Mass

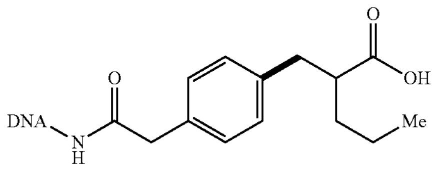

Following General Procedure 2 (Condition A) with A20 except for employing AgOAc instead of AgTFA.

Yield: 20/85×100%=24%

Ratio (product/deiodination/aryl iodide): 20/16/17

Exact mass: 5166.9925

Triply charged mass [M]/3-1.00794, calculated 1721.3229; observed 1721.3342.

LC Trace and Mass of 16

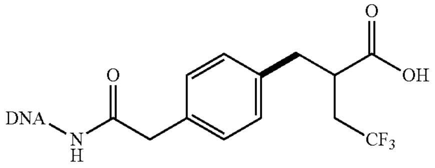

Following General Procedure 2 (Condition A) with A21 except for employing AgOTf instead of AgTFA.

Yield: 22/85×100%=26%

Ratio (product/deiodination/aryl iodide): 22/27/14

Exact mass: 5206.9486

Triply charged mass [M]/3-1.00794, calculated 1734.6416; observed 1734.6637.

LC Trace and Mass of 17

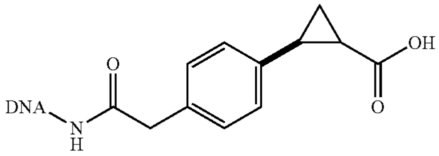

Following General Procedure 2 (Condition B) with A22.

Yield: 35/85×100%=41%

Ratio (product/deiodination/aryl iodide): 35/9/7

Exact mass: 5136.9455

Triply charged mass [M]/3-1.00794, calculated 1711.3072; observed 1711.3074.

LC Trace and Mass of 18

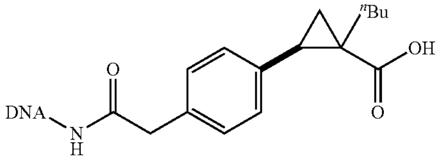

Following General Procedure 2 (Condition A) with A23.

Yield: 40/85×100%=47%

Ratio (product/deiodination/aryl iodide): 40/3/21

Exact mass: 5193.0081

Triply charged mass [M]/3-1.00794, calculated 1729.9948; observed 1729.9934.

LC Trace and Mass of 19

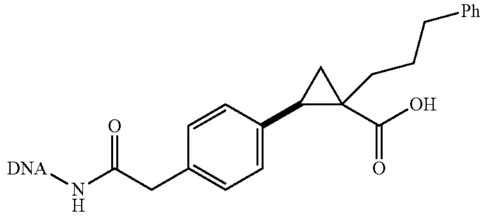

Following General Procedure 2 (Condition A) with A24.

Yield: 34/85×100%=40%

Ratio (product/deiodination/aryl iodide): 34/0/29

Exact mass: 5255.0238

Triply charged mass [M]/3-1.00794, calculated 1750.6667; observed 1750.6652.

LC Trace and Mass

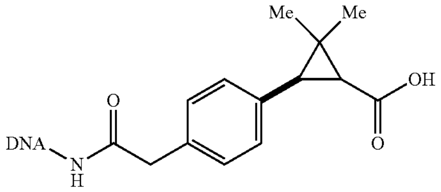

Following General Procedure 2 (Condition A) with A25 except for employing $Ag_2CO_3$ instead of AgTFA.

Yield: 18/85×100%=21%

Ratio (product/deiodination/aryl iodide): 18/15/6

Exact mass: 5164.9768

Triply charged mass [M]/3-1.00794, calculated 1720.6510; observed 1720.6547.

LC Trace and Mass of 20

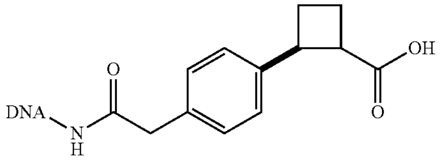

Following General Procedure 2 (Condition A) with A26 (1000 mM) except for employing $Ag_2CO_3$ instead of AgTFA.

Yield: 33/85×100%=39%

Ratio (product/deiodination/aryl iodide): 33/23/5

Exact mass: 5150.9612

Triply charged mass [M]/3-1.00794, calculated 1715.9791; observed 1715.9694.

LC Trace and Mass of 21

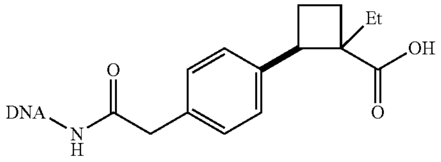

Following General Procedure 2 (Condition A) with A27 except for employing $Ag_2CO_3$ instead of AgTFA.

Yield: 34/85×100%=40%

Ratio (product/deiodination/aryl iodide): 34/15/18

Exact mass: 5178.9925

Triply charged mass [M]/3-1.00794, calculated 1725.3229; observed 1725.3293.

LC Trace and Mass of 22

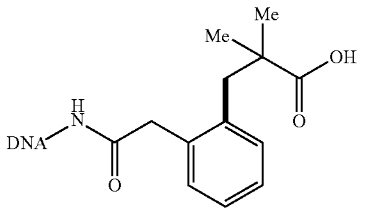

Following General Procedure 2 (Condition A) with S2 and A1 (1000 mM) except for employing $Ag_2CO_3$ instead of AgTFA.

Yield: $\frac{46}{83}$×100%=55%

Ratio (product/deiodination/aryl iodide): 46/31/4

Exact mass: 5152.9768

Triply charged mass [M]/3-1.00794, calculated 1716.6510; observed 1716.6649.

LC Trace and Mass

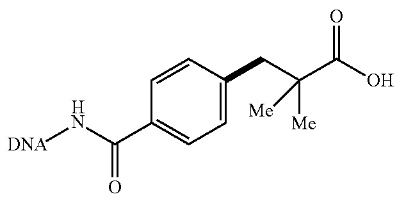

Following General Procedure 2 (Condition A) with S3 and A1 (1000 mM) except for employing $Ag_2CO_3$ instead of AgTFA.

Yield: $\frac{57}{78}$×100%=73%

Ratio (product/deiodination/aryl iodide): 57/3/15

Exact mass: 5166.9925

Triply charged mass [M]/3-1.00794, calculated 1721.3229; observed 1721.3342.

LC Trace and Mass

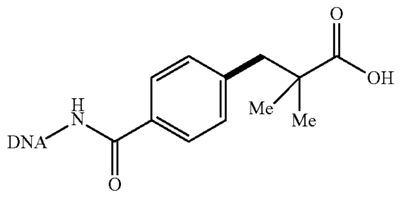

Following General Procedure 2 (Condition A) with S10 and A1 (1000 mM) except for employing $Ag_2CO_3$ instead of AgTFA.

Yield: $\frac{57}{85}$×100%=67%

Ratio (product/deiodination/aryl iodide): 57/8/23

Exact mass: 5138.9612

Triply charged mass [M]/3-1.00794, calculated 1711.9791; observed 1711.9851.

LC Trace and Mass of 25

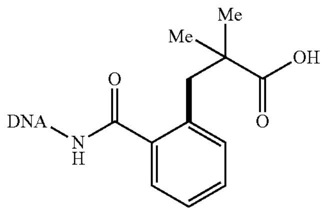

Following General Procedure 2 (Condition A) with S4 and A1 (1000 mM) except for employing $Ag_2CO_3$ instead of AgTFA.

Yield: $\frac{35}{74}$×100%=47%

Ratio (product/deiodination/aryl iodide): 35/24/3

Exact mass: 5138.9612

Triply charged mass [M]/3-1.00794, calculated 1711.9791; observed 1711.9851.

LC Trace and Mass of 26

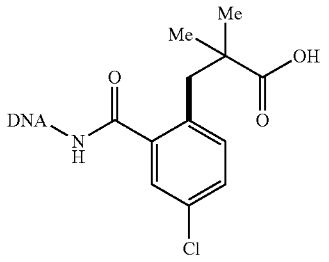

Following General Procedure 2 (Condition A) with S6 and A1 (1000 mM) except for employing $Ag_2CO_3$ instead of AgTFA.

Yield: $\frac{35}{67}$×100%=52%

Ratio (product/deiodination/aryl iodide): 35/22/3

Exact mass: 5172.9222

Triply charged mass [M]/3-1.00794, calculated 1723.2995; observed 1723.3057.

LC Trace and Mass of 27

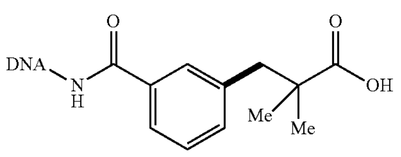

Following General Procedure 2 (Condition A) with S7 and A1 (1000 mM) except for employing $Ag_2CO_3$ instead of AgTFA.

Yield: $\frac{50}{83}$×100%=60%

Ratio (product/deiodination/aryl iodide): 50/5/22

Exact mass: 5138.9612

Triply charged mass [M]/3-1.00794, calculated 1711.9791; observed 1711.9851.

LC Trace and Mass of 28

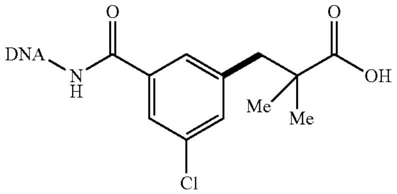

Following General Procedure 2 (Condition A) with S9 and A1 (1000 mM) except for employing $Ag_2CO_3$ instead of AgTFA.

Yield: 41/71×100%=58%

Ratio (product/deiodination/aryl iodide): 41/11/18

Exact mass: 5172.9222

Triply charged mass [M]/3-1.00794, calculated 1723.2995; observed 1723.3057.

LC Trace and Mass of 29

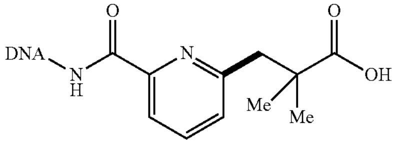

Following General Procedure 2 (Condition A) with S14 and A1 (1000 mM) except for employing $Ag_2CO_3$ instead of AgTFA.

Yield: 42/57×100%=74%

Ratio (product/deiodination/aryl iodide): 42/10/2

Exact mass: 5139.9564

Triply charged mass [M]/3-1.00794, calculated 1712.3109; observed 1712.3240.

LC Trace and Mass of 30

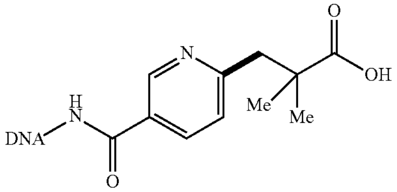

Following General Procedure 2 (Condition A) with S15 and A1 (1000 mM) except for employing $Ag_2CO_3$ instead of AgTFA.

Yield: 53/65×100%=82%

Ratio (product/deiodination/aryl iodide): 53/7/4

Exact mass: 5139.9564

Triply charged mass [M]/3-1.00794, calculated 1712.3109; observed 1712.3240.

LC Trace and Mass of 31

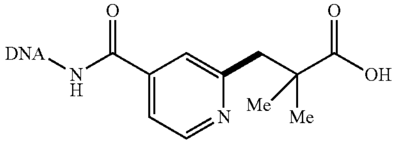

Following General Procedure 2 (Condition A) with S18 and A1 (1000 mM) except for employing $Ag_2CO_3$ instead of AgTFA.

Yield: 41/56×100%=73%

Ratio (product/deiodination/aryl iodide): 41/7/2

Exact mass: 5139.9564

Triply charged mass [M]/3-1.00794, calculated 1712.3109; observed 1712.3070.

LC Trace and Mass of 32

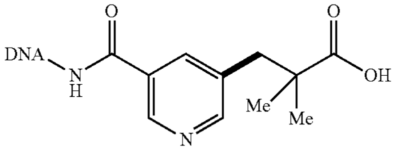

Following General Procedure 2 (Condition A) with S16 and A1 (1000 mM) except for employing $Ag_2CO_3$ instead of AgTFA.

Yield: 30/79×100%=38%

Ratio (product/deiodination/aryl iodide): 30/18/28

Exact mass: 5139.9564

Triply charged mass [M]/3-1.00794, calculated 1712.3109; observed 1712.3240.

LC Trace and Mass of 33

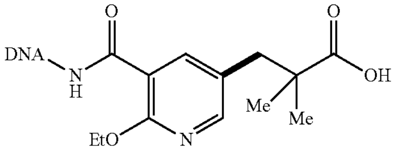

Following General Procedure 2 (Condition A) with S17 and A1 (1000 mM) except for employing $Ag_2CO_3$ instead of AgTFA.

Yield: 35/59×100%=59%

Ratio (product/deiodination/aryl iodide): 35/13/11

Exact mass: 5183.9827

Triply charged mass [M]/3-1.00794, calculated 1726.9863; observed 1726.9968.

LC Trace and Mass of 34

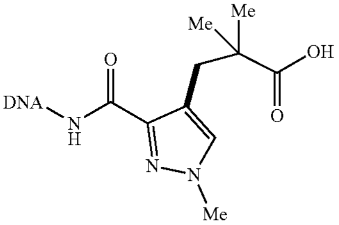

Following General Procedure 2 (Condition A) with S19 and A1 (1000 mM) except for employing $Ag_2CO_3$ instead of AgTFA.

Yield: 35/77×100%=45%

Ratio (product/deiodination/aryl iodide): 35/24/17

Exact mass: 5142.9673

Triply charged mass [M]/3-1.00794, calculated 1713.3145; observed 1713.3240.

LC Trace and Mass of 35

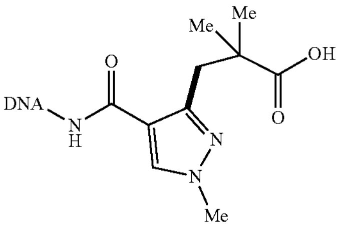

Following General Procedure 2 (Condition A) with S20 and A1 (1000 mM) except for employing $Ag_2CO_3$ instead of AgTFA.

Yield: 22/76×100%=29%

Ratio (product/deiodination/aryl iodide): 22/43/3

Exact mass: 5142.9673

Triply charged mass [M]/3-1.00794, calculated 1713.3145; observed 1713.3240.

LC Trace and Mass of 36

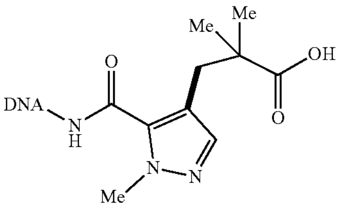

Following General Procedure 2 (Condition A) with S21 and A1 (1000 mM) except for employing $Ag_2CO_3$ instead of AgTFA.

Yield: 23/69×100%=33%

Ratio (product/deiodination/aryl iodide): 23/19/30

Exact mass: 5142.9673

Triply charged mass [M]/3-1.00794, calculated 1713.3145; observed 1713.3240.

LC Trace and Mass of 37

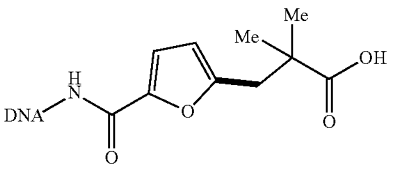

Following General Procedure 2 (Condition A) with S22 and A1 (1000 mM) except for employing $Ag_2CO_3$ instead of AgTFA.

Yield: 51/67×100%=76%

Ratio (product/deiodination/aryl iodide): 51/7/0

Exact mass: 5128.9405

Triply charged mass [M]/3-1.00794, calculated 1708.6389; observed 1708.6487.

LC Trace and Mass of 38

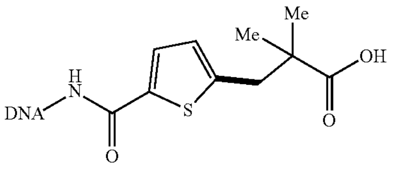

Following General Procedure 2 (Condition A) with S23 and A1 (1000 mM) except for employing $Ag_2CO_3$ instead of AgTFA.

Yield: 46/69×100%=67%

Ratio (product/deiodination/aryl iodide): 46/12/0

Exact mass: 5144.9176

Triply charged mass [M]/3-1.00794, calculated 1713.9646; observed 1713.9681.

LC Trace and Mass of 39

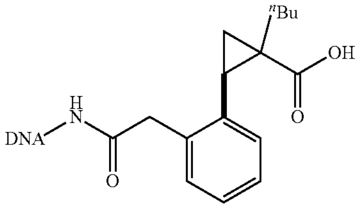

Following General Procedure 2 (Condition A) with S2 and A23.

Yield: 38/83×100%=46%

Ratio (product/deiodination/aryl iodide): 38/3/14

Exact mass: 5193.0081

Triply charged mass [M]/3-1.00794, calculated 1729.9948; observed 1729.9934.

LC Trace and Mass of 40

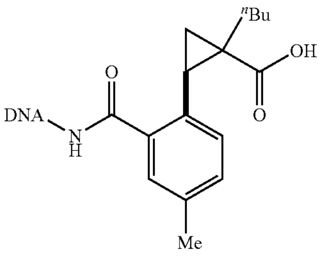

Following General Procedure 2 (Condition A) with S5 and A23.

Yield: 24/69×100%=35%

Ratio (product/deiodination/aryl iodide): 24/16/3

Exact mass: 5193.0081

Triply charged mass [M]/3-1.00794, calculated 1729.9948; observed 1729.9934.

LC Trace and Mass of 41

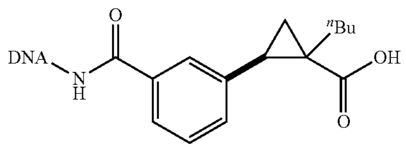

Following General Procedure 2 (Condition A) with S7 and A23.

Yield: 33/83×100%=40%

Ratio (product/deiodination/aryl iodide): 33/3/12

Exact mass: 5178.9925

Triply charged mass [M]/3-1.00794, calculated 1725.3229; observed 1725.3293.

LC Trace and Mass of 42

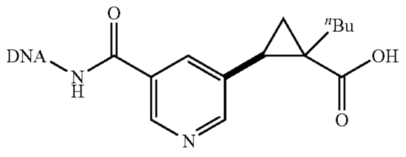

Following General Procedure 2 (Condition A) with S16 and A23.

Yield: 21/79×100%=27%

Ratio (product/deiodination/aryl iodide): 21/3/25

Exact mass: 5179.9877

Triply charged mass [M]/3-1.00794, calculated 1725.6546; observed 1725.6526.

LC Trace and Mass of 43

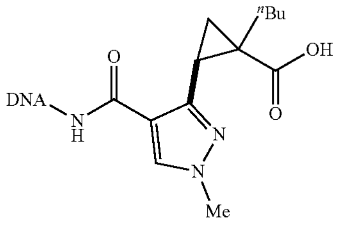

Following General Procedure 2 (Condition A) with S20 and A23.

Yield: 21/76×100%=28%

Ratio (product/deiodination/aryl iodide): 21/17/0

Exact mass: 5182.9986

Triply charged mass [M]/3-1.00794, calculated 1726.6583; observed 1726.6564.

LC Trace and Mass of 44

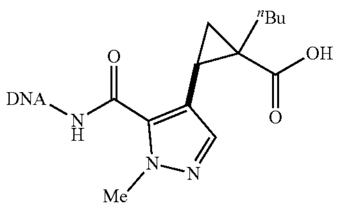

Following General Procedure 2 (Condition A) with S21 and A23.

Yield: 20/69×100%=29%

Ratio (product/deiodination/aryl iodide): 20/12/11

Exact mass: 5182.9986

Triply charged mass [M]/3-1.00794, calculated 1726.6583; observed 1726.6564.

LC Trace and Mass

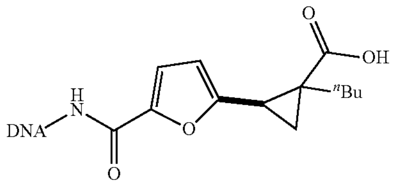

Following General Procedure 2 (Condition A) with S22 and A23.

Yield: 18/67×100%=27%

Ratio (product/deiodination/aryl iodide): 18/7/0

Exact mass: 5168.9718

Triply charged mass [M]/3-1.00794, calculated 1721.9827; observed 1721.9800.

5. Experimental Section for on-DNA C—H Arylation of Amides

5.1 Substrate Structures of Amides B1-B16

B1

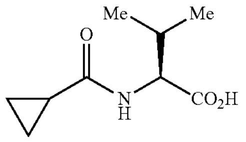

B2

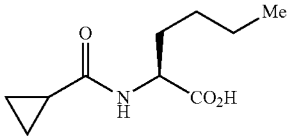

B3

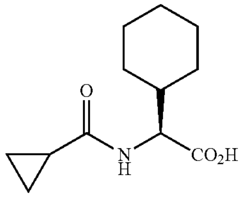

B4

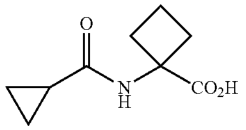

B5

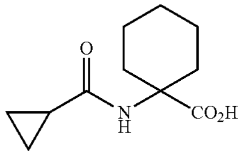

B6

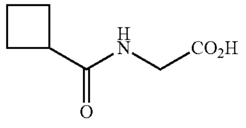

-continued
B7
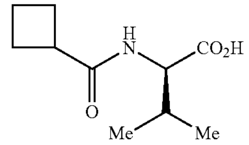
B8
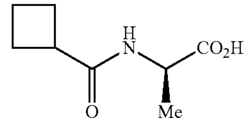
B9
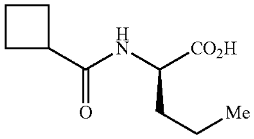
B10
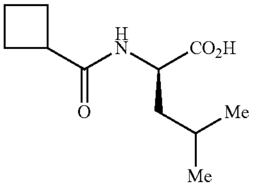
B11
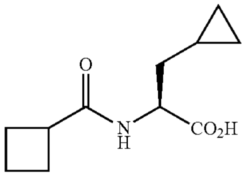
-continued
B12
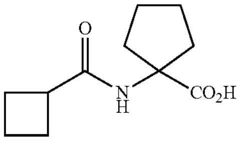
B13
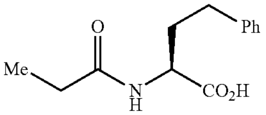
B14
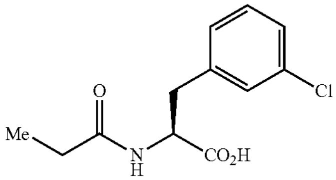
B15
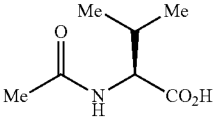
B16
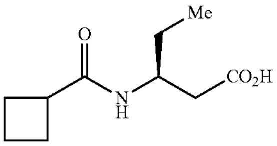
Amides were obtained from the commercial sources or synthesized following the literature procedures.[21]
5.2 Condition Optimizations
TABLE 10
Evaluation of Ag salt
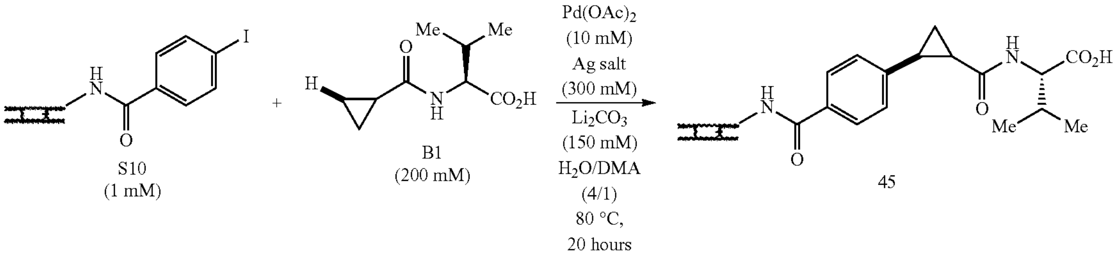
S10 (1 mM) + B1 (200 mM) → 45
| Entry | Ag salt (300 mM) | Yield (%) |
|---|---|---|
| 1 | AgOAc | 46 |
| 2 | $AgNO_3$ | 12 |
| 3 | AgTFA | 46 |
| 4 | $Ag_2CO_3$ | 42 |
| 5 | AgOTs | 35 |

TABLE 11

Evaluation of Base

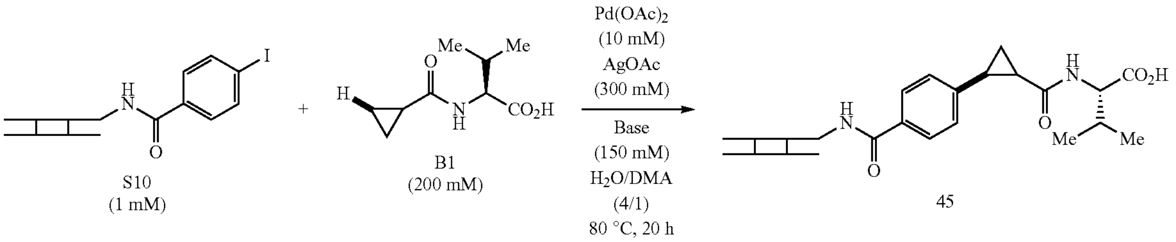

S10
(1 mM)
B1
(200 mM)
45

| Entry | Base (150 mM) | Yield (%) |
|---|---|---|
| 1 | NaOAC | 46 |
| 2 | $Na_2CO_3$ | 55 |
| 3 | $K_2CO_3$ | 41 |
| 4 | $K_3PO_4$ | 31 |
| 5 | $K_2HPO_4$•$3H_2O$ | 18 |
| 6 | $Li_2CO_3$ | 69 |
| 7 | $CS_2CO_3$ | 41 |

TABLE 12

Evaluation of Standard Conditions

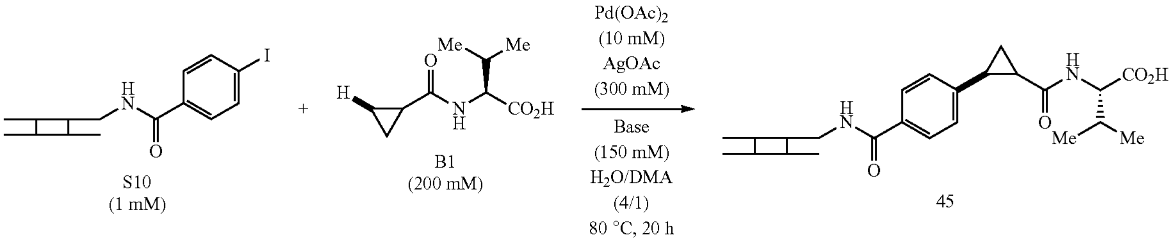

S10
(1 mM)
B1
(200 mM)
45

| Entry | Deviation from above | Yield (%) |
|---|---|---|
| 1 | none | 69 |
| 2 | without $Pd(OAc)_2$ | 0 |
| 3 | without AgOAc | 24 |
| 4 | without $Li_2CO_3$ | 35 |
| 5 | r.t. instead of 80 °C | 60 |

5.3 General Procedure 3 for on-DNA C—H Arylation of Amides

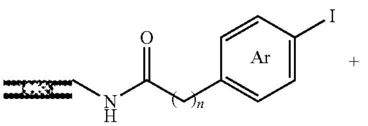
S
(1 mM)

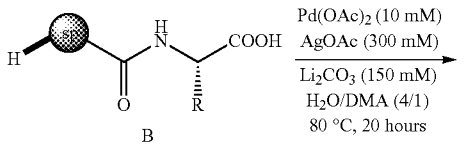

B
(200 mM)

-continued

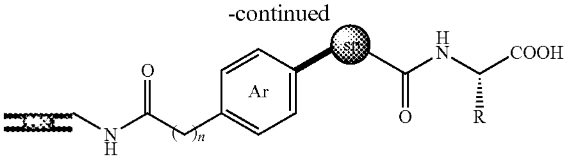
45-72

Materials

DNA-conjugated aryl iodide S: 10 mM in $H_2O$

Amide B: 2 M in DMA $Pd(OAc)_2$: 200 mM in HFIP

Sodium diethyldithiocarbamate trihydrate (scavenger): 1 M in $H_2O$

Procedure

1) To a 200 μL microcentrifuge tube was added $Pd(OAc)_2$ (10 equiv, 0.5 μL), after air-dry, AgOAc (300 equiv, 0.5 mg), amide B (200 equiv, 1 μL), DNA-conjugated aryl iodide S (10 nmol, 1 μL), $Li_2CO_3$ (150 equiv, 0.11 mg), DMA (1 μL) and deionized water (7 μL) were added. The mixture was vortexed. The reaction mixture was heated at 80° C. for 20 hours.

2) Cooling to room temperature, 9.0 μL scavenger was added, and the mixture was reheated at 80° C. for 30 minutes.

3) Cooling to room temperature, 5 M NaCl solution (10% by volume, 1.9 μL) and cold ethanol (2.5 times by volume, 47.5 μL). The mixture was stored in a freezer at −20° C. for more than 30 minutes.

4) Centrifuge the sample for around 10 minutes in a microcentrifuge at 10000 rpm. The above supernatant was discarded and the precipitate was dried under vacuum. The DNA pellet was redissolved in $H_2O$ (100 μL) and centrifuged for about 2 minutes in a microcentrifuge at 10000 rpm. An aliquot (50 μL) was taken and analyzed via HPLC-MS.

5.4 General Procedure 4 for Synthesis of Dipeptides

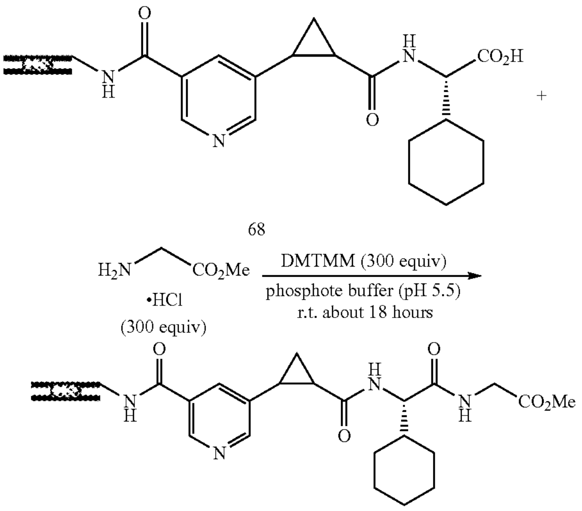

73, 96 %

Materials

68: ca. 5 mM in $H_2O$

Glycine methyl ester hydrochloride: 1 M in $H_2O$

DMTMM: 1 M in $H_2O$ pH 5.5 phosphate buffer: 0.2 M $NaH_2PO_4$ in $H_2O$

Procedure

1) To 2 μL 68 solution was added 22 μL pH 5.5 phosphate buffer, glycine methyl ester hydrochloride (300 equiv, 3 μL) and DMTMM (300 equiv, 3 μL). The mixture was vortexed, and kept at room temperature overnight (16-18 hours).

2) Add 5 M NaCl solution (10% by volume) and cold ethanol (2.5 times by volume, ethanol stored at −20° C.). The mixture was stored at in a freezer at −20° C. for 1 hour.

3) Centrifuge the sample for around 10 minutes in a microcentrifuge at 10000 rpm. The above supernatant was discarded and the precipitate was dried under vacuum. The DNA pellet was redissolved in $H_2O$ (100 μL) and centrifuged for around 2 minutes in a microcentrifuge at 10000 rpm. An aliquot (50 μL) was taken and analyzed via HPLC-MS.

5.5 LC Trace and Mass Characterization of 52-80

LC Trace and Mass of 45

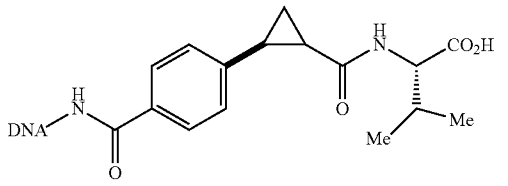

Following General Procedure 3 with B1.

Yield: $^{59}/_{85}\times100\%=69\%$

Ratio (product/deiodination/aryl iodide): 59/0/3

Exact mass: 5221.9983

Triply charged mass [M]/3-1.00794, calculated 1739.6582; observed 1739.6648.

Following General Procedure 3 with B1 except for running reaction and quenching with scavenger at room temperature.

Yield: $^{51}/_{85}\times100\%=60\%$

Ratio (product/deiodination/aryl iodide): 51/4/5

Exact mass: 5221.9983

Triply charged mass [M]/3-1.00794, calculated 1739.6582; observed 1739.6648.

LC Trace and Mass of 46

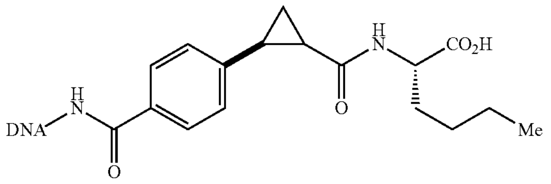

Following General Procedure 3 with B2.

Yield: $^{56}/_{85}\times100\%=66\%$

Ratio (product/deiodination/aryl iodide): 56/3/0

Exact mass: 5236.0140

Triply charged mass [M]/3-1.00794, calculated 1744.3301; observed 1744.3309.

Following General Procedure 3 with B2 except for running reaction and quenching with scavenger at room temperature.

Yield: $^{71}/_{85}\times100\%=84\%$

Ratio (product/deiodination/aryl iodide): 71/1/10

Exact mass: 5236.0140

Triply charged mass [M]/3-1.00794, calculated 1744.3301; observed 1744.3309.

LC Trace and Mass of 47

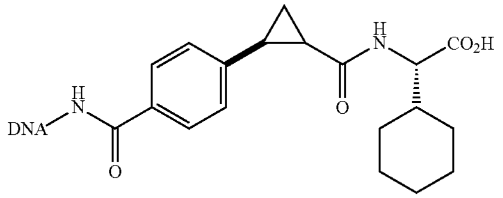

Following General Procedure 3 with B3.

Yield: $^{72}/_{85}\times100\%=85\%$

Ratio (product/deiodination/aryl iodide): 72/2/6

Exact mass: 5262.0296

Triply charged mass [M]/3-1.00794, calculated 1753.0019; observed 1752.9962.

Following General Procedure 3 with B3 except for running reaction and quenching with scavenger at room temperature.

Yield: 55/85×100%=65%

Ratio (product/deiodination/aryl iodide): 55/6/28

Exact mass: 5262.0296

Triply charged mass [M]/3-1.00794, calculated 1753.0019; observed 1752.9962.

LC Trace and Mass of 48

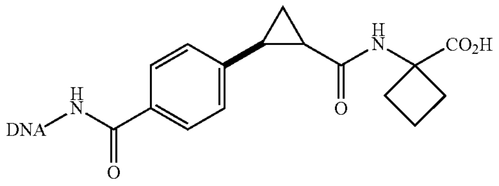

Following General Procedure 3 with B4.

Yield: 29/85×100%=34%

Ratio (product/deiodination/aryl iodide): 29/10/0

Exact mass: 5219.9827

Triply charged mass [M]/3-1.00794, calculated 1738.9863; observed 1738.9816.

Following General Procedure 3 with B4 except for running reaction and quenching with scavenger at room temperature.

Yield: 46/85×100%=54%

Ratio (product/deiodination/aryl iodide): 46/4/10

Exact mass: 5219.9827

Triply charged mass [M]/3-1.00794, calculated 1738.9863; observed 1738.9816.

LC Trace and Mass of 49

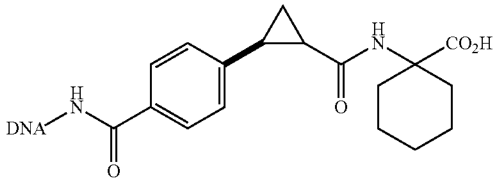

Following General Procedure 3 with B5.

Yield: 56/85×100%=66%

Ratio (product/deiodination/aryl iodide): 56/3/4

Exact mass: 5248.0140

Triply charged mass [M]/3-1.00794, calculated 1748.3301; observed 1748.3356.

Following General Procedure 3 with B5 except for running reaction and quenching with scavenger at room temperature.

Yield: 35/85×100%=41%

Ratio (product/deiodination/aryl iodide): 35/9/41

Exact mass: 5248.0140

Triply charged mass [M]/3-1.00794, calculated 1748.3301; observed 1748.3356.

LC Trace and Mass of 50

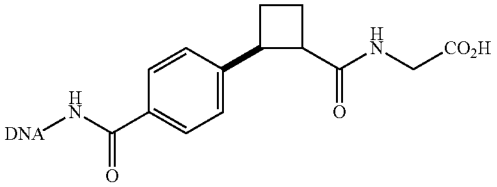

Following General Procedure 3 with B6.

Yield: 48/85×100%=56%

Ratio (product/deiodination/aryl iodide): 48/6/5

Exact mass: 5193.9670

Triply charged mass [M]/3-1.00794, calculated 1730.3144; observed 1730.3170.

Following General Procedure 3 with B6 except for running reaction and quenching with scavenger at room temperature.

Yield: 51/85×100%=60%

Ratio (product/deiodination/aryl iodide): 51/1/29

Exact mass: 5193.9670

Triply charged mass [M]/3-1.00794, calculated 1730.3144; observed 1730.3170.

LC Trace and Mass of 51

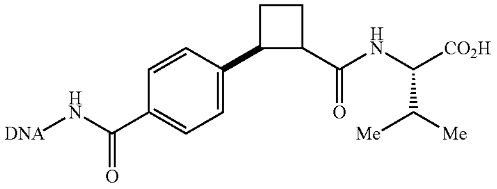

Following General Procedure 3 with B7.

Yield: 63/85×100%=74%

Ratio (product/deiodination/aryl iodide): 63/3/0

Exact mass: 5236.0140

Triply charged mass [M]/3-1.00794, calculated 1744.3301; observed 1744.3309.

Following General Procedure 3 with B7 except for running reaction and quenching with scavenger at room temperature.

Yield: 66/85×100%=78%

Ratio (product/deiodination/aryl iodide): 66/2/13

Exact mass: 5236.0140

Triply charged mass [M]/3-1.00794, calculated 1744.3301; observed 1744.3309.

LC Trace and Mass of 52

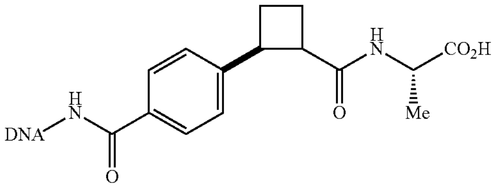

Following General Procedure 3 with B8.

Yield: 72/85×100%=85%

Ratio (product/deiodination/aryl iodide):72/0/0

Exact mass: 5207.9827

Triply charged mass [M]/3-1.00794, calculated 1734.9863; observed 1734.9877.

Following General Procedure 3 with B8 except for running reaction and quenching with scavenger at room temperature.

Yield: 70/85×100%=82%

Ratio (product/deiodination/aryl iodide):70/0/16

Exact mass: 5207.9827

Triply charged mass [M]/3-1.00794, calculated 1734.9863; observed 1734.9877.

LC Trace and Mass of 53

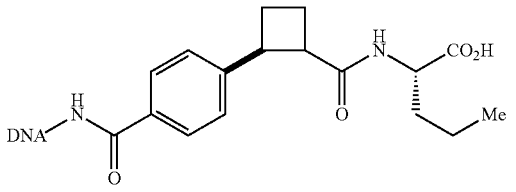

Following General Procedure 3 with B9.

Yield: 62/85×100%=73%

Ratio (product/deiodination/aryl iodide): 62/2/0

Exact mass: 5236.0140

Triply charged mass [M]/3-1.00794, calculated 1744.3301; observed 1744.3309.

Following General Procedure 3 with B9 except for running reaction and quenching with scavenger at room temperature.

Yield: 70/85×100%=82%

Ratio (product/deiodination/aryl iodide): 70/5/9

Exact mass: 5236.0140

Triply charged mass [M]/3-1.00794, calculated 1744.3301; observed 1744.3309.

LC Trace and Mass of 54

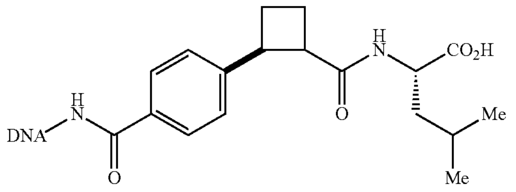

Following General Procedure 3 with B10.

Yield: 72/85×100%=85%

Ratio (product/deiodination/aryl iodide): 72/2/3

Exact mass: 5250.0296

Triply charged mass [M]/3-1.00794, calculated 1749.0019; observed 1749.0034.

Following General Procedure 3 with B10 except for running reaction and quenching with scavenger at room temperature.

Yield: 44/85×100%=22%

Ratio (product/deiodination/aryl iodide): 19/2/55

Exact mass: 5250.0296

Triply charged mass [M]/3-1.00794, calculated 1749.0019; observed 1749.0034.

LC Trace and Mass of 55

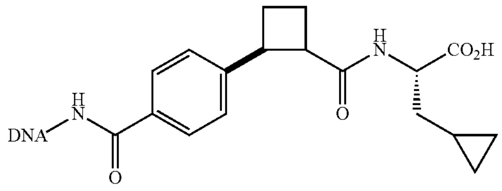

Following General Procedure 3 with B11.

Yield: 44/85×100%=52%

Ratio (product/deiodination/aryl iodide): 44/4/5

Exact mass: 5248.0140

Triply charged mass [M]/3-1.00794, calculated 1748.3301; observed 1748.3356.

Following General Procedure 3 with B11 except for running reaction and quenching with scavenger at room temperature.

Yield: 40/85×100%=47%

Ratio (product/deiodination/aryl iodide): 40/9/10

Exact mass: 5248.0140

Triply charged mass [M]/3-1.00794, calculated 1748.3301; observed 1748.3356.

LC Trace and Mass of 56

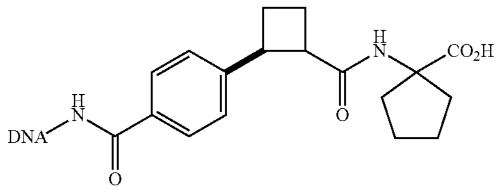

Following General Procedure 3 with B12.

Yield: 63/85×100%=74%

Ratio (product/deiodination/aryl iodide): 63/3/2

Exact mass: 5248.0140

Triply charged mass [M]/3-1.00794, calculated 1748.3301; observed 1748.3356.

Following General Procedure 3 with B12 except for running reaction and quenching with scavenger at room temperature.

Yield: 68/85×100%=80%

Ratio (product/deiodination/aryl iodide): 68/6/8

Exact mass: 5248.0140

Triply charged mass [M]/3-1.00794, calculated 1748.3301; observed 1748.3356.

LC Trace and Mass of 57

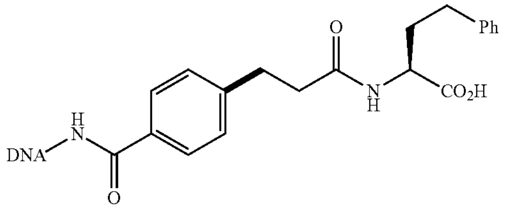

Following General Procedure 3 with B13.

Yield: 43/85×100%=51%

Ratio (product/deiodination/aryl iodide): 43/6/22

Exact mass: 5272.0140

Triply charged mass [M]/3-1.00794, calculated 1756.3301; observed 1756.33413.

LC Trace and Mass of 58

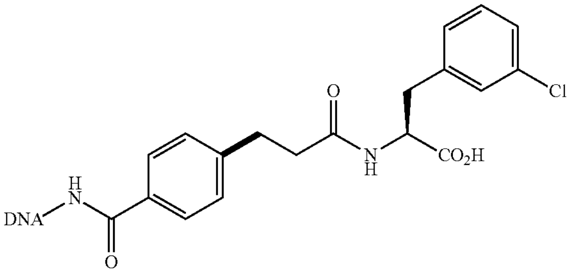

Following General Procedure 3 with B14.

Yield: 30/85×100%=35%

Ratio (product/deiodination/aryl iodide): 30/2/43

Exact mass: 5291.9593

Triply charged mass [M]/3-1.00794, calculated 1762.9785; observed 1762.9895.

Following General Procedure 3 with B14 except for running reaction and quenching with scavenger at room temperature.

Yield: 13/85×100%=15%

Ratio (product/deiodination/aryl iodide): 13/6/58

Exact mass: 5291.9593

Triply charged mass [M]/3-1.00794, calculated 1762.9785; observed 1762.9895.

LC Trace and Mass of 60

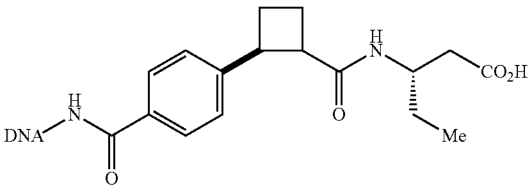

Following General Procedure 3 with B16.

Yield: 37/85×100%=44%

Ratio (product/deiodination/aryl iodide): 37/5/2

Exact mass: 5236.0140

Triply charged mass [M]/3-1.00794, calculated 1744.3301; observed 1744.3309.

Following General Procedure 3 with B16 except for running reaction and quenching with scavenger at room temperature.

Yield: 54/85×100%=64%

Ratio (product/deiodination/aryl iodide): 54/15/5

Exact mass: 5236.0140

Triply charged mass [M]/3-1.00794, calculated 1744.3301; observed 1744.3309.

LC Trace and Mass of 61

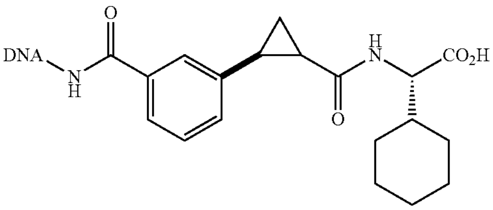

Following General Procedure 3 with S7 and B3.

Yield: 50/83×100%=60%

Ratio (product/deiodination/aryl iodide): 50/2/0

Exact mass: 5262.0296

Triply charged mass [M]/3-1.00794, calculated 1753.0019; observed 1753.0133.

LC Trace and Mass of 62,

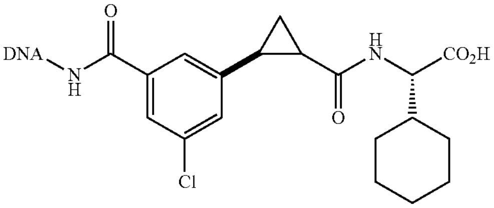

Following General Procedure 3 with S9 and B3.

Yield: 55/71×100%=77%

Ratio (product/deiodination/aryl iodide): 55/5/0

Exact mass: 5295.9906

Triply charged mass [M]/3-1.00794, calculated 1764.3223; observed 1764.3309.

LC Trace and Mass of 63

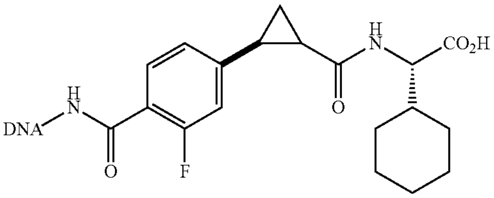

Following General Procedure 3 with S13 and B3.

Yield: 51/55×100%=93%

Ratio (product/deiodination/aryl iodide): 51/3/0

Exact mass: 5280.0202

Triply charged mass [M]/3-1.00794, calculated 1758.9988; observed 1759.0026.

LC Trace and Mass of 64

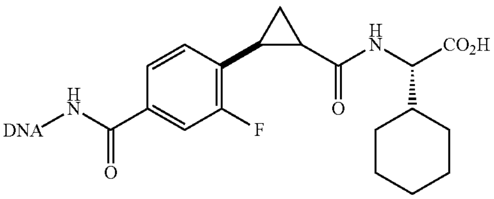

Following General Procedure 3 with S12 and B3.

Yield: 52/71×100%=73%

Ratio (product/deiodination/aryl iodide): 52/6/1

Exact mass: 5280.0202

Triply charged mass [M]/3-1.00794, calculated 1758.9988; observed 1759.0026.

LC Trace and Mass of 65

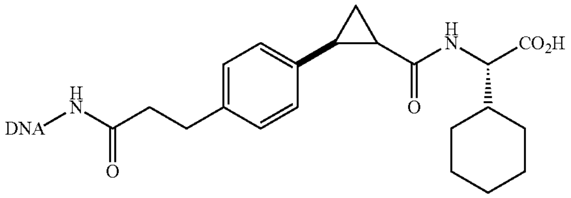

Following General Procedure 3 with S3 and B3.

Yield: 50/78×100%=64%

Ratio (product/deiodination/aryl iodide): 50/1/0

Exact mass: 5290.0609

Triply charged mass [M]/3-1.00794, calculated 1762.3457; observed 1762.3534.

LC Trace and Mass of 66

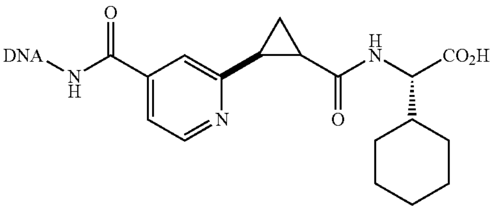

Following General Procedure 3 with S18 and B3.

Yield: 45/56×100%=80%

Ratio (product/deiodination/aryl iodide): 45/2/0

Exact mass: 5263.0249

Triply charged mass [M]/3-1.00794, calculated 1753.3337; observed 1753.3391.

LC Trace and Mass of 67

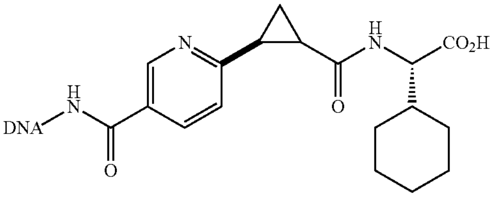

Following General Procedure 3 with S15 and B3.

Yield: 42/65×100%=65%

Ratio (product/deiodination/aryl iodide): 42/1/3

Exact mass: 5263.0249

Triply charged mass [M]/3-1.00794, calculated 1753.3337; observed 1753.3391.

LC Trace and Mass of 68

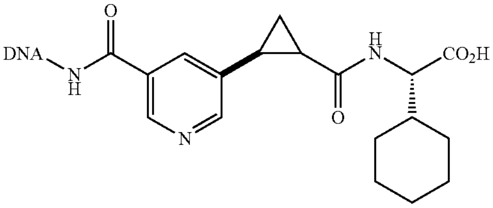

Following General Procedure 3 with S16 and B3.

Yield: 53/79×100%=67%

Ratio (product/deiodination/aryl iodide): 53/2/3

Exact mass: 5263.0249

Triply charged mass [M]/3-1.00794, calculated 1753.3337; observed 1753.3391.

LC Trace and Mass of 69

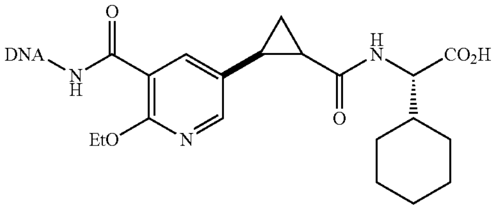

Following General Procedure 3 with S17 and B3.

Yield: 56/78×100%=72%

Ratio (product/deiodination/aryl iodide): 56/9/0

Exact mass: 5307.0511

Triply charged mass [M]/3-1.00794, calculated 1768.0091; observed 1768.0140.

LC Trace and Mass of 70

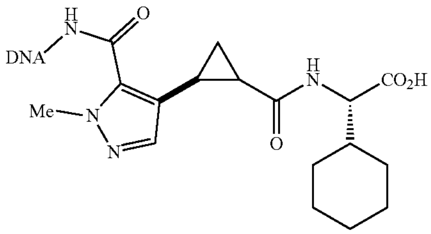

Following General Procedure 3 with S21 and B3.

Yield: 33/69×100%=48%

Ratio (product/deiodination/aryl iodide): 33/16/5

Exact mass: 5266.0358

Triply charged mass [M]/3-1.00794, calculated 1754.3373; observed 1754.3339.

LC Trace and Mass of 71

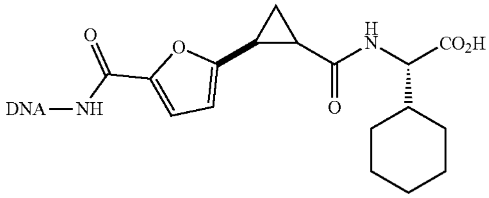

Following General Procedure 3 with S22 and B3.

Yield: 39/67×100%=58%

Ratio (product/deiodination/aryl iodide): 39/3/0

Exact mass: 5252.0089

Triply charged mass [M]/3-1.00794, calculated 1749.6617; observed 1749.6714.

LC Trace and Mass of 72

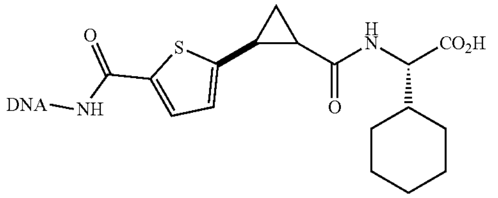

Following General Procedure 3 with S23 and B3.

Yield: $52/69 \times 100\% = 75\%$

Ratio (product/deiodination/aryl iodide): 52/3/0

Exact mass: 5267.9860

Triply charged mass [M]/3-1.00794, calculated 1754.9874; observed 1754.9857.

LC Trace and Mass of 73

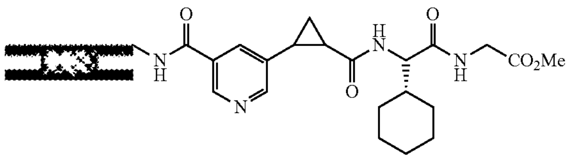

Following General Procedure 4 with 68.

Yield: $51/53 \times 100\% = 96\%$

Exact mass: 5334.0620

Triply charged mass [M]/3-1.00794, calculated 1777.0127; observed 1777.0140.

6. Experimental Section for On-DNA C—H Arylation of Ketones

6.1 Substrate Structures of Ketones Containing Directing Groups (DGs) C1-C30

C1

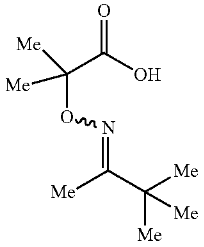

C2

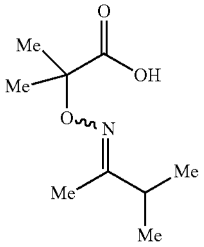

-continued

C3

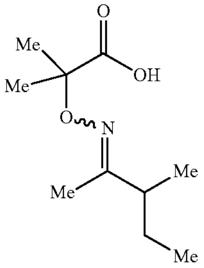

C4

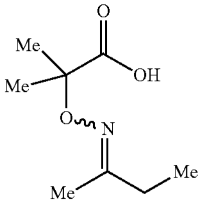

C5

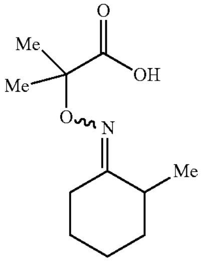

C6

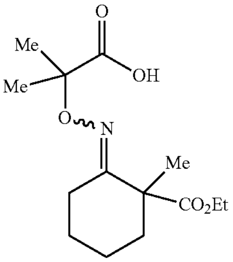

C7

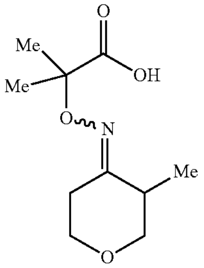

C8

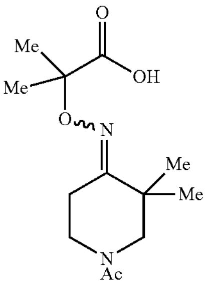

-continued
C9
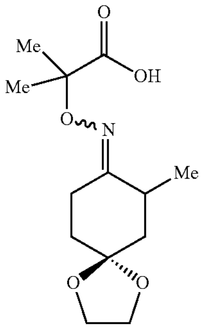
C10
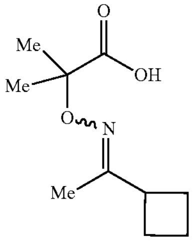
C11
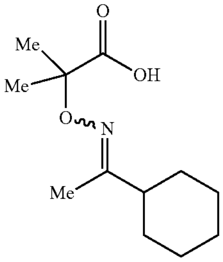
C12
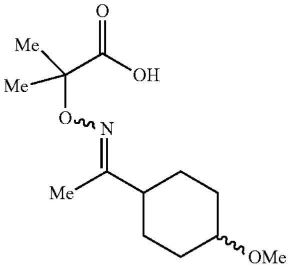
C13
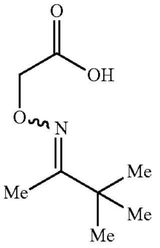
C14
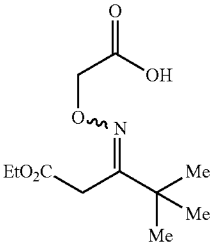
-continued
C15
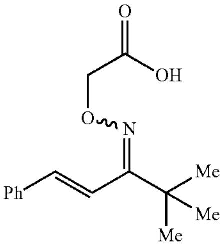
C16
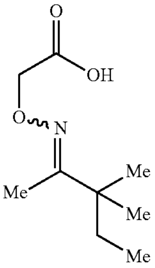
C17
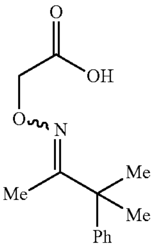
C18
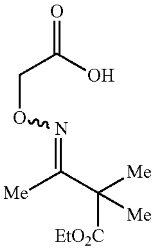
C19
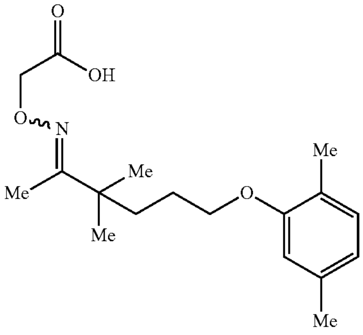
C20
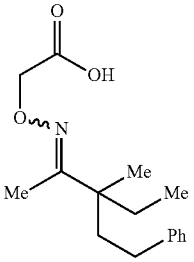

-continued
C21
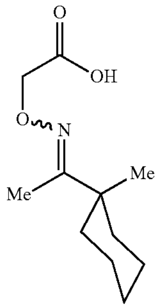
C22
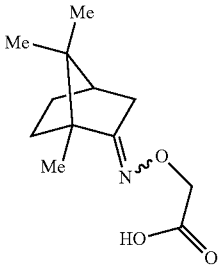
C23
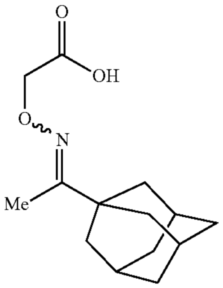
C24
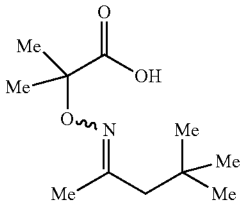
C25
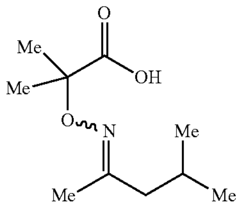
C26
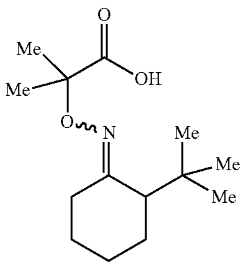
-continued
C27
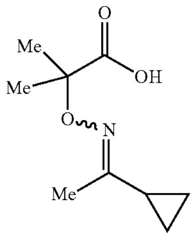
C28
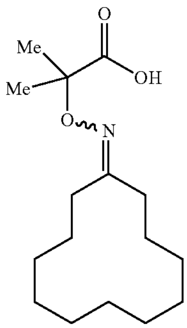
C29
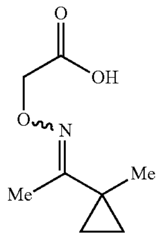
C30
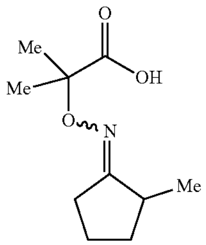
Ketones containing directing groups C1-C30 were synthesized as previously reported.[16a]

6.2 Condition Optimizations
TABLE 13
Ligand Optimization
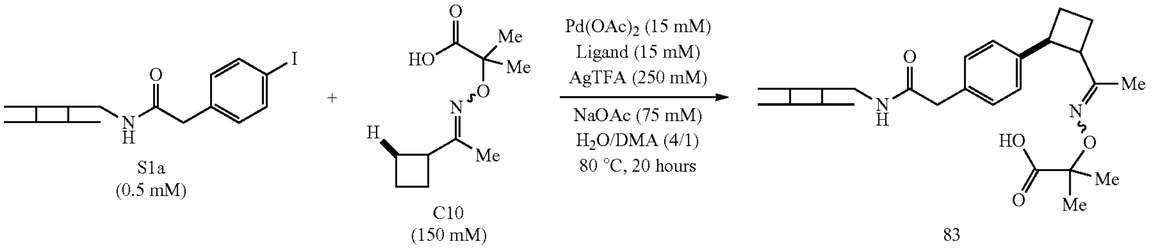
S1a (0.5 mM) + C10 (150 mM) → 83
| Entry | Ligand (15 mM) | Yield (%) |
|---|---|---|
| 1 | L6 | 16 |
| 2 | L7 | 32 |
| 3 | L8 | 38 |
| 4 | L9 | 36 |
| 5 | L10 | 32 |
| 6 | L11 | 33 |
| 7 | L12 | 37 |
| 8 | L13 | 27 |
TABLE 14
Co-solvent Optimization
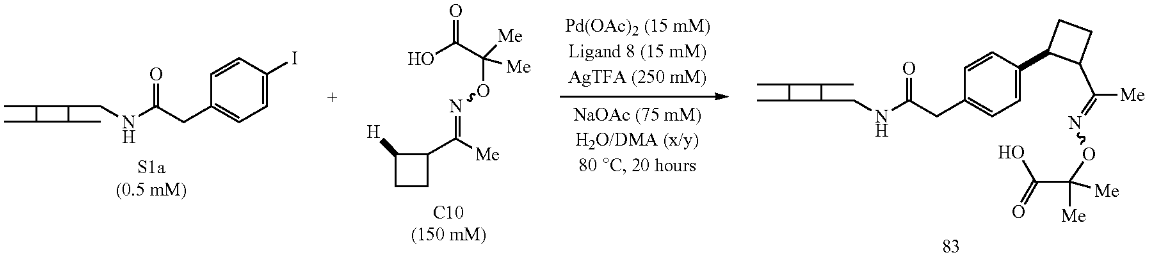
S1a (0.5 mM) + C10 (150 mM) → 83
| Entry | $H_2O$/Co-solvent (x/y) | Yield (%) |
|---|---|---|
| 1 | $H_2O$/DMA (1 /1) | 28 |
| 2 | $H_2O$/DMA (2/1) | 39 |
| 3 | $H_2O$/DMF (2/1) | 35 |
| 4 | $H_2O$/DMSO (2/1) | 26 |
TABLE 15
Pd/L8 Concentration Optimization
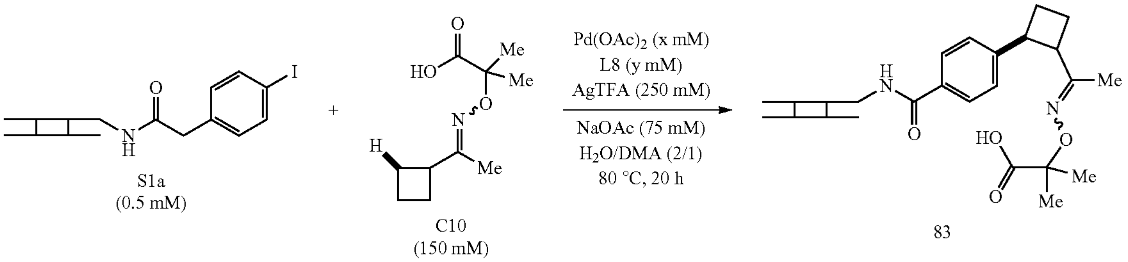
S1a (0.5 mM) + C10 (150 mM) → 83
| Entry | Pd/L8 (x/y) | Yield (%) |
|---|---|---|
| 1 | 20/10 | 33 |
| 2 | 20/15 | 48 |
| 3 | 20/20 | 48 |

TABLE 16

Solvent Ratio Optimization

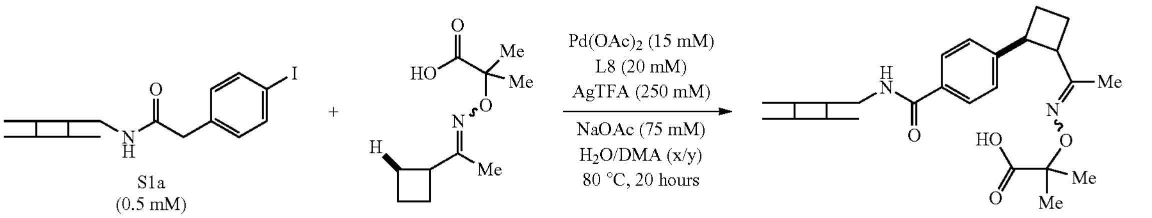

S1a (0.5 mM) + C10 (150 mM) → 83

| Entry | $H_2O$/DMA (x/y) | Yield (%) |
|---|---|---|
| 1 | 4/1 | 51 |
| 2 | 9/1 | 62 |

TABLE 17

Evaluation of Standard Conditions

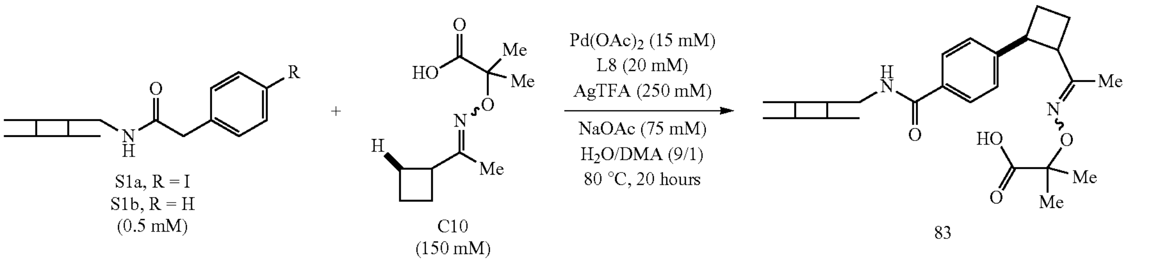

S1a, R = I
S1b, R = H
(0.5 mM)

C10 (150 mM)

83

| Entry | Deviation from above | Yield (%) |
|---|---|---|
| 1 | none | 62 |
| 2 | without $Pd(OAc)_2$ | 0 |
| 3 | without AgTFA | 4 |
| 4 | without NaOAc | 55 |
| 5 | Without L8 | 51 |
| 6 | r.t instead of 80° C. | 0 |
| 7 | $Ag_2CO_3$ (150 mM) instead of AgTFA (250 mM) | 25 |
| 8 | AgOAC (250 mM) instead of AgTFA (250 mM) | 32 |
| 9 | C10 (100 mM) instead of 150 mM | 61 |
| 10 | C10 (200 mM) instead of 150 mM | 53 |
| 11 | C10 (250 mM) instead of 150 mM | 54 |
| 12 | L1 instead of L8 | 48 |
| 13 | L5 instead of L8 | 45 |
| 14 | $Pd(OAC)_2$/L8 (15/15) instead of 20/20 | 49 |
| 15 | S1b instead of S1a | 0[a] |

[a]Only S1b was totally recovered.

6.3 General Procedure 5 for on-DNA C—H Arylation of Ketones

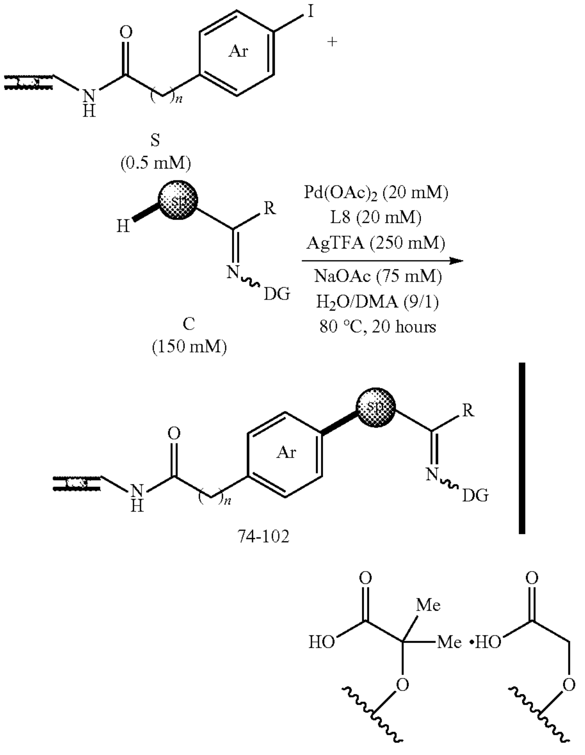

S
(0.5 mM)
C
(150 mM)
74-102
DG1
DG2

Materials

DNA-conjugated aryl iodide S: 10 mM in $H_2O$

Ketone C: 3 M in DMA (Note: the high concentration may increase the total volume)

L8: 400 mM in DMA (6.5 mg in 100 μL DMA)

$Pd(OAc)_2$: 400 mM in HFIP (9 mg in 100 μL HFIP)

NaOAc: 1.5 M in $H_2O$ (12.3 mg in 100 μL $H_2O$)

Sodium diethyldithiocarbamate trihydrate (scavenger): 1 M in $H_2O$

Procedure

1) To prepared AgTFA (500 equiv, 1.1 mg) was added $Pd(OAc)_2$ (40 equiv, 1 μL), after air-dry, ketone C (300 equiv, ca. 1.3 μL), DNA-conjugated aryl iodide S (10 nmol, 1 μL), L8 (40 equiv, 1 μL), NaOAc aqueous solution (150 equiv, 1 μL) and deionized water (16 μL) were added. The mixture was vortexed. The reaction mixture was heated at 80° C. for 20 hours.

2) Cooling to room temperature, 9.0 μL scavenger was added and reheating the mixture at 80° C. for 30 minutes.

3) Cooling to room temperature, 5 M NaCl solution (10% by volume, 2.9 μL) and cold ethanol (3 times by volume, 87 μL). The mixture was stored in a freezer at −20° C. for more than 30 minutes.

4) Centrifuge the sample for about 7 minutes in a micro-centrifuge at 10000 rpm. The supernatant was discarded and the precipitate was dried under vacuum. The DNA pellet was redissolved in $H_2O$ (100 μL) and centrifuged for about 2 minutes in a microcentrifuge at 10000 rpm. An aliquot (50 μL) was taken and analyzed via HPLC-MS.

6.4 Limitations of Ketones

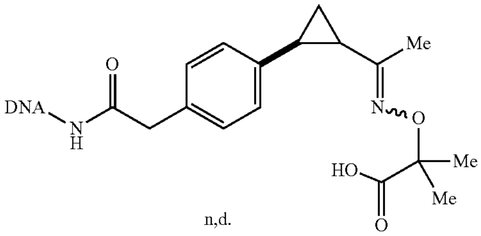
n,d.

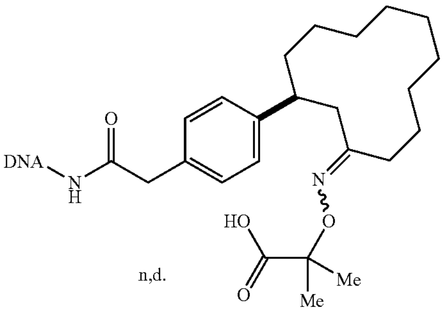
n,d.

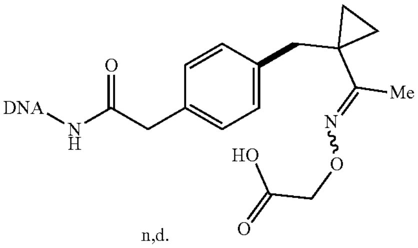
n,d.

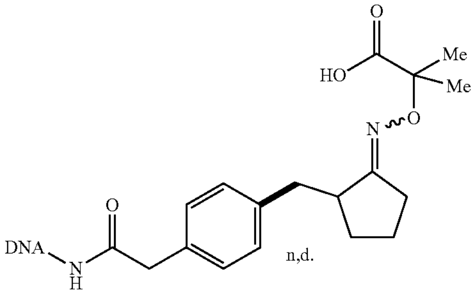
n,d.

6.5 General Procedure 6 for Removal of DG

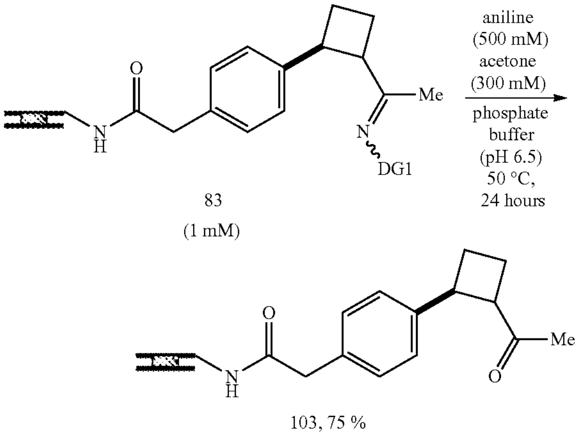

83
(1 mM)
103, 75 %

1) Aniline (0.45 μL, 5 μmol, 500 equiv) and acetone (0.22 μL, 3 μmol, 300 equiv) were added to a solution of the DNA-tethered substrate 83 (ca. 10 nmol) in pH 6.5 phosphate buffer (20 μL). The reaction mixture was subsequently heated at 50° C. for 24 hours.

2) Cooling to room temperature, 5 M NaCl solution (3 μL) and cold ethanol (200 μL). The mixture was stored in a freezer at −20° C. for more than 30 minutes.

3) Centrifuge the sample for about 7 minutes in a microcentrifuge at 10000 rpm. The supernatant was discarded and the precipitate was dried under vacuum. The DNA pellet was redissolved in $H_2O$ (100 μL) and centrifuged for about 2 minutes in a microcentrifuge at 10000 rpm. An aliquot (50 μL) was taken and analyzed via HPLC-MS.

6.6 LC Trace and Mass Characterization of 81-119

LC Trace and Mass of 74

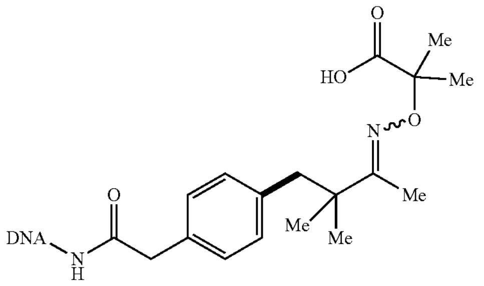

Following General Procedure 5 with C1.

Yield: 31/85×100%=36%

Ratio (product/deiodination/aryl iodide): 31/1/12

Exact mass: 5252.0453

Triply charged mass [M]/3-1.00794, calculated 1749.6738; observed 1749.6714.

LC Trace and Mass of 75

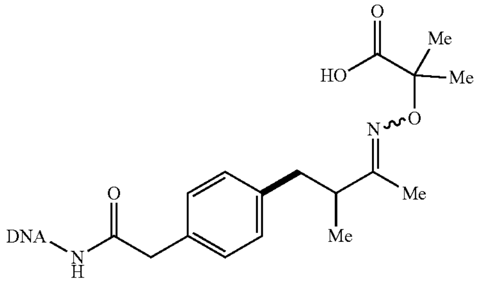

Following General Procedure 5 with C2.

Yield: 55/85×100%=65%

Ratio (product/deiodination/aryl iodide): 55/1/12

Exact mass: 5238.0296

Triply charged mass [M]/3-1.00794, calculated 1745.0019; observed 1745.0151.

LC Trace and Mass of 76

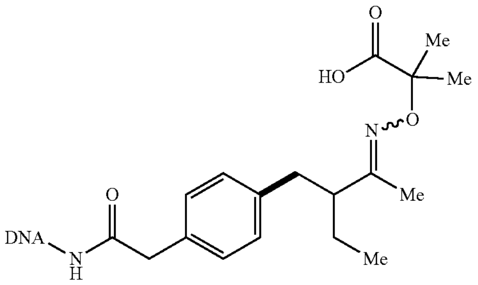

Following General Procedure 5 with C3.

Yield: 38/85×100%=45%

Ratio (product/deiodination/aryl iodide): 38/1/25

Exact mass: 5252.0453

Triply charged mass [M]/3-1.00794, calculated 1749.6738; observed 1749.6886.

LC Trace and Mass of 77

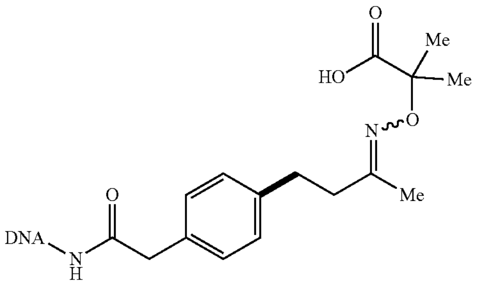

Following General Procedure 5 with C4.

Yield: 47/85×100%=55%

Ratio (product/deiodination/aryl iodide): 47/3/0

Exact mass: 5224.0140

Triply charged mass [M]/3-1.00794, calculated 1740.3301; observed 1740.3309.

LC Trace and Mass of 78

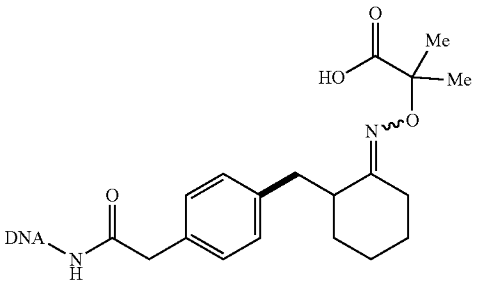

Following General Procedure 5 with C5.

Yield: 34/85×100%=40%

Ratio (product/deiodination/aryl iodide): 34/1/22

Exact mass: 5264.0453

Triply charged mass [M]/3-1.00794, calculated 1753.6738; observed 1753.6821.

LC Trace and Mass of 79

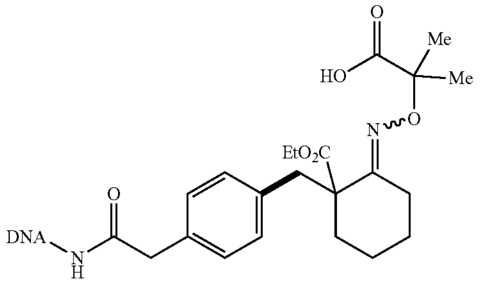

Following General Procedure 5 with C6.

Yield: 17/85×100%=20%

Ratio (product/deiodination/aryl iodide): 17/7/39

Exact mass: 5336.0664

Triply charged mass [M]/3-1.00794, calculated 1777.6809; observed 1777.6874.

LC Trace and Mass of 80

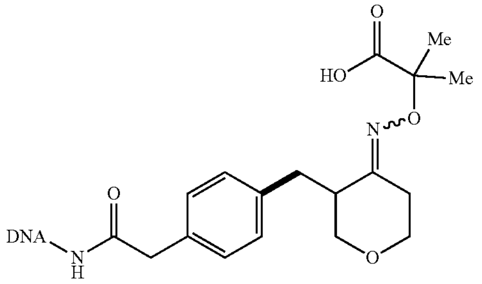

Following General Procedure 5 with C7.

Yield: 34/85×100%=40%

Ratio (product/deiodination/aryl iodide): 34/2/41

Exact mass: 5266.0245

Triply charged mass [M]/3-1.00794, calculated 1754.3336; observed 1754.3339.

LC Trace and Mass of 81

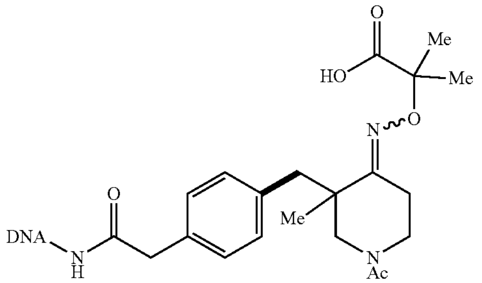

Following General Procedure 5 with C8.

Yield: 29/85×100%=34%

Ratio (product/deiodination/aryl iodide): 29/2/8

Exact mass: 5321.0667

Triply charged mass [M]/3-1.00794, calculated 1772.6810; observed 1772.6836.

LC Trace and Mass of 82

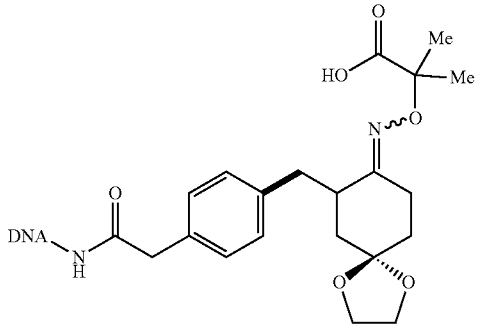

Following General Procedure 5 with C9.

Yield: 36/85×100%=42%

Ratio (product/deiodination/aryl iodide): 36/2/26

Exact mass: 5322.0507

Triply charged mass [M]/3-1.00794, calculated 1773.0090; observed 1773.0112.

LC Trace and Mass of 83

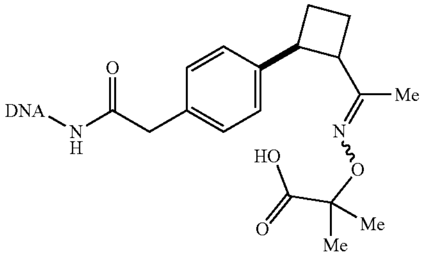

Following General Procedure 5 with C10.

Yield: 53/85×100%=62%

Ratio (product/deiodination/aryl iodide): 53/2/5

Exact mass: 5250.0296

Triply charged mass [M]/3-1.00794, calculated 1749.0019; observed 1749.0034.

LC Trace and Mass

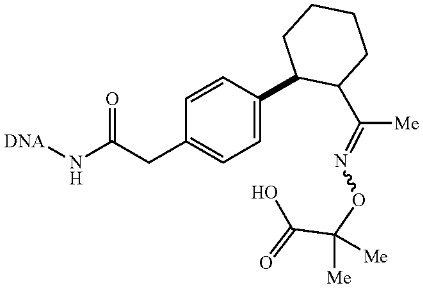

Following General Procedure 5 with C11.

Yield: 17/85×100%=20%

Ratio (product/deiodination/aryl iodide): 17/9/32

Exact mass: 5278.0609

Triply charged mass [M]/3-1.00794, calculated 1758.3457; observed 1758.3500.

LC Trace and Mass

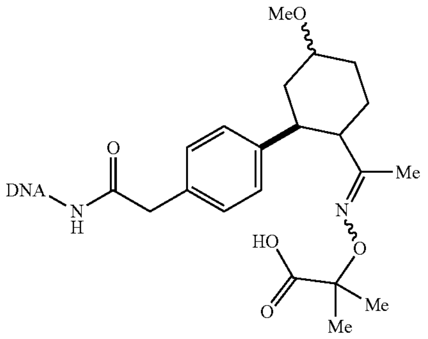

Following General Procedure 5 with C12.

Yield: 17/85×100%=20%

Ratio (product/deiodination/aryl iodide): 17/4/33

Exact mass: 5308.0715

Triply charged mass [M]/3-1.00794, calculated 1768.3492; observed 1768.3584.

LC Trace and Mass of 84

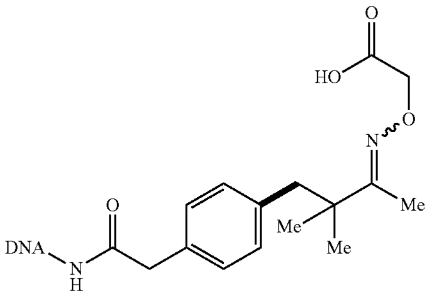

Following General Procedure 5 with C13.

Yield: 36/85×100%=42%

Ratio (product/deiodination/aryl iodide): 36/2/13

Exact mass: 5224.0140

Triply charged mass [M]/3-1.00794, calculated 1740.3301; observed 1740.3309.

LC Trace and Mass

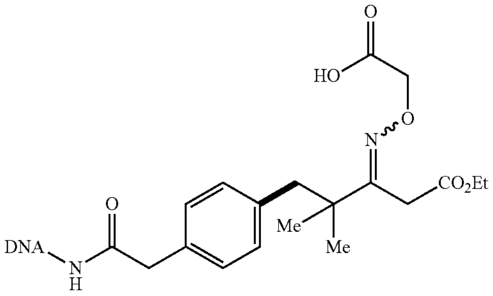

Following General Procedure 5 with C14.

Yield: 18/85×100%=21%

Ratio (product/deiodination/aryl iodide): 18/2/28

Exact mass: 5296.0351

Triply charged mass [M]/3-1.00794, calculated 1764.3371; observed 1764.3481.

LC Trace and Mass of 85,

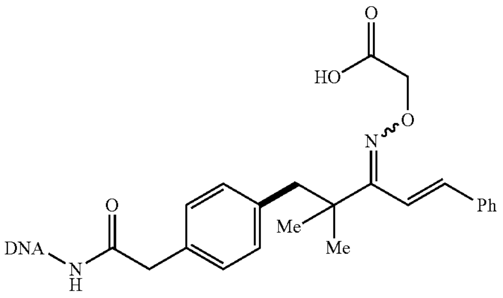

Following General Procedure 5 with C15.

Yield: 33/85×100%=39%

Ratio (product/deiodination/aryl iodide): 33/1/9

Exact mass: 5312.0453

Triply charged mass [M]/3-1.00794, calculated 1769.6738; observed 1769.6847.

LC Trace and Mass of 86

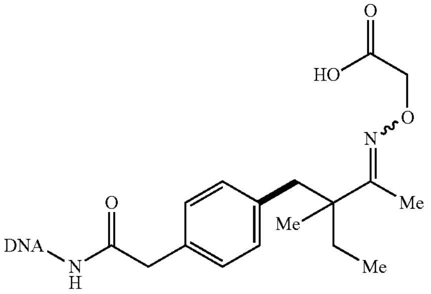

Following General Procedure 5 with C16.

Yield: 38/85×100%=45%

Ratio (product/deiodination/aryl iodide): 38/0/6

Exact mass: 5238.0296

Triply charged mass [M]/3-1.00794, calculated 1745.0019; observed 1744.9980.

LC Trace and Mass of 87

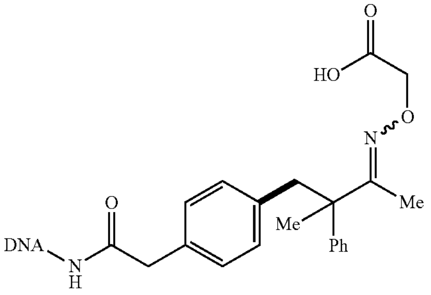

Following General Procedure 5 with C17.

Yield: 32/85×100%=38%

Ratio (product/deiodination/aryl iodide): 32/1/21

Exact mass: 5286.0296

Triply charged mass [M]/3-1.00794, calculated 1761.0019; observed 1761.0127.

LC Trace and Mass

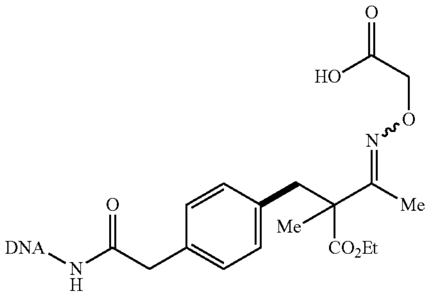

Following General Procedure 5 with C18.

Yield: $^{17}/_{85}\times100\%=20\%$

Ratio (product/deiodination/aryl iodide): 17/6/14

Exact mass: 5282.0194

Triply charged mass [M]/3-1.00794, calculated 1759.6652; observed 1759.6725.

LC Trace and Mass of 88

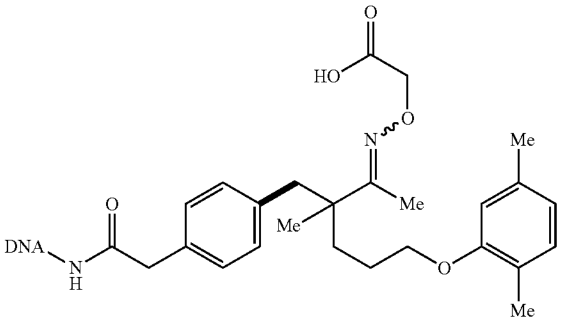

Following General Procedure 5 with C19.

Yield: $^{37}/_{85}\times100\%=44\%$

Ratio (product/deiodination/aryl iodide): 37/1/24

Exact mass: 5372.1028

Triply charged mass [M]/3-1.00794, calculated 1789.6930; observed 1789.6906.

LC Trace and Mass of 89

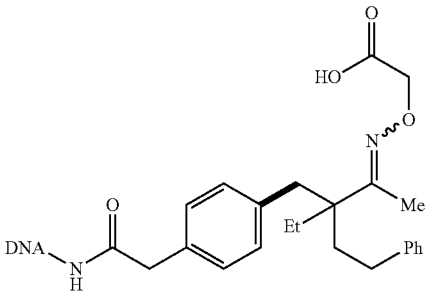

Following General Procedure 5 with D20 except for employing $Pd(OAc)_2$ (15 mM) and L8 (15 mM) in $H_2O$/DMA (2/1).

Yield: $^{29}/_{85}\times100\%=34\%$

Ratio (product/deiodination/aryl iodide): 29/2/10

Exact mass: 5328.0766

Triply charged mass [M]/3-1.00794, calculated 1775.0176; observed 1775.0293.

LC Trace and Mass of 90

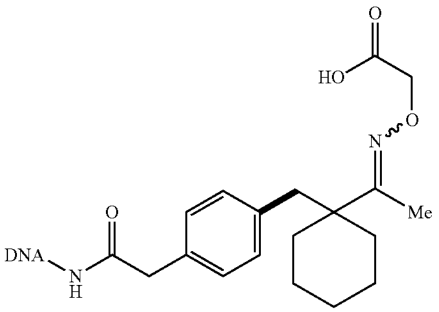

Following General Procedure 5 with C21 except for employing $Pd(OAc)_2$ (15 mM) and L8 (15 mM) in $H_2O$/DMA (2/1).

Yield: $^{58}/_{85}\times100\%=68\%$

Ratio (product/deiodination/aryl iodide): 58/1/14

Exact mass: 5264.0453

Triply charged mass [M]/3-1.00794, calculated 1753.6738; observed 1753.6821.

LC Trace and Mass of 91

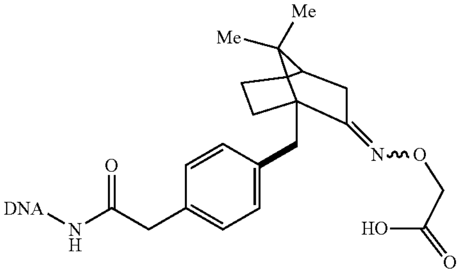

Following General Procedure 5 with C22.

Yield: $^{34}/_{85}\times100\%=40\%$

Ratio (product/deiodination/aryl iodide): 34/4/25

Exact mass: 5276.0453

Triply charged mass [M]/3-1.00794, calculated 1757.6738; observed 1757.6803.

LC Trace and Mass of 92

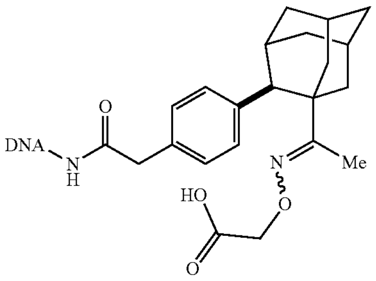

Following General Procedure 5 with C23.

Yield: $^{29}/_{85}\times100\%=34\%$

Ratio (product/deiodination/aryl iodide): 29/1/19

Exact mass: 5302.0609

Triply charged mass [M]/3-1.00794, calculated 1766.3457; observed 1766.3441.

LC Trace and Mass

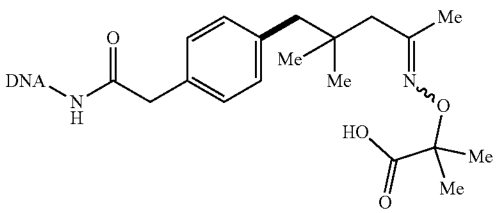

Following General Procedure 5 with C24.

Yield: 33/85×100%=15%

Ratio (product/deiodination/aryl iodide): 13/2/41

Exact mass: 5266.0609

Triply charged mass [M]/3-1.00794, calculated 1754.3457; observed 1754.3511.

LC Trace and Mass

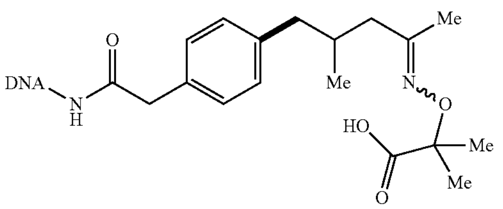

Following General Procedure 5 with C25.

Yield: 8/85×100%=9%

Ratio (product/deiodination/aryl iodide): 8/2/52

Exact mass: 5252.0453

Triply charged mass [M]/3-1.00794, calculated 1749.6738; observed 1749.6886.

LC Trace and Mass of 93

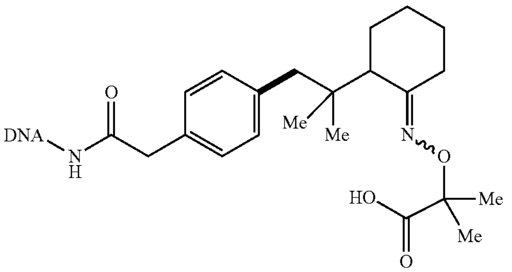

Following General Procedure 5 with C26.

Yield: 19/85×100%=22%

Ratio (product/deiodination/aryl iodide): 19/2/30

Exact mass: 5306.0922

Triply charged mass [M]/3-1.00794, calculated 1767.6895; observed 1767.6869.

LC Trace and Mass

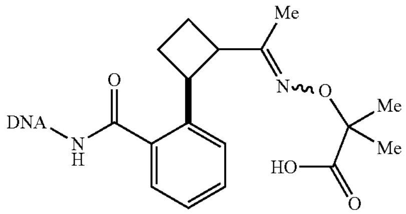

Following General Procedure 5 with S4 and C10.

Yield: 23/74×100%=31%

Ratio (product/deiodination/aryl iodide): 23/6/2

Exact mass: 5236.0140

Triply charged mass [M]/3-1.00794, calculated 1744.3301; observed 1744.3309.

LC Trace and Mass

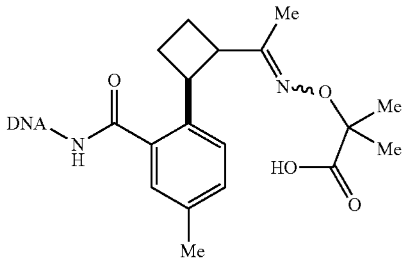

Following General Procedure 5 with S5 and C10.

Yield: 22/69×100%=32%

Ratio (product/deiodination/aryl iodide): 22/10/4

Exact mass: 5250.0296

Triply charged mass [M]/3-1.00794, calculated 1749.0019; observed 1749.0034.

LC Trace and Mass of 94

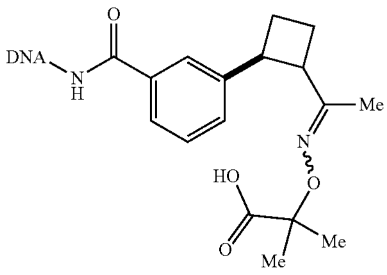

Following General Procedure 5 with S7 and C10.

Yield: 51/83×100%=61%

Ratio (product/deiodination/aryl iodide): 51/1/9

Exact mass: 5236.0140

Triply charged mass [M]/3-1.00794, calculated 1744.3301; observed 1744.3309.

LC Trace and Mass of 95

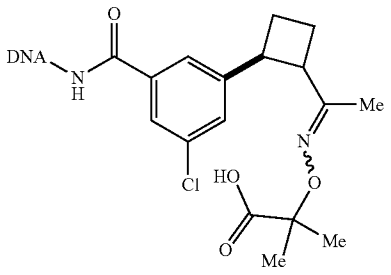

Following General Procedure 5 with S9 and C10.

Yield: $^{26}/_{71}$×100%=37%

Ratio (product/deiodination/aryl iodide): 26/3/16

Exact mass: 5269.9750

Triply charged mass [M]/3-1.00794, calculated 1755.6504; observed 1755.6549.

LC Trace and Mass of 96

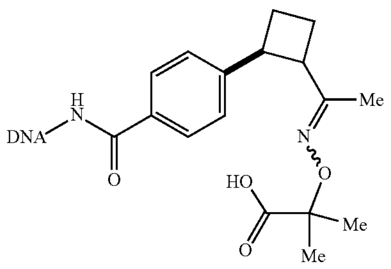

Following General Procedure 5 with S10 and C10.

Yield: $^{29}/_{85}$×100%=34%

Ratio (product/deiodination/aryl iodide): 29/1/4

Exact mass: 5236.0140

Triply charged mass [M]/3-1.00794, calculated 1744.3301; observed 1744.3309.

LC Trace and Mass of 97

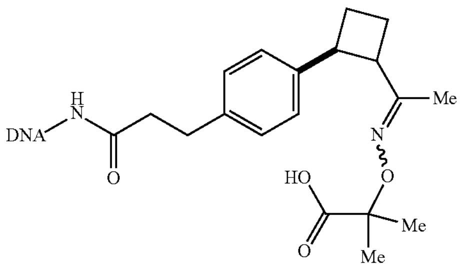

Following General Procedure 5 with S3 and C10.

Yield: $^{43}/_{78}$×100%=55%

Ratio (product/deiodination/aryl iodide): 43/1/4

Exact mass: 5264.0454

Triply charged mass [M]/3-1.00794, calculated 1753.6739; observed 1753.6821.

LC Trace and Mass of 98

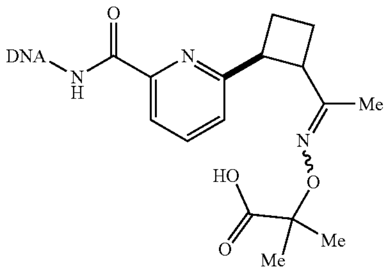

Following General Procedure 5 with S14 and C10.

Yield: $^{36}/_{57}$×100%=63%

Ratio (product/deiodination/aryl iodide): 36/5/1

Exact mass: 5237.0092

Triply charged mass [M]/3-1.00794, calculated 1744.6618; observed 1744.6731.

LC Trace and Mass of 99

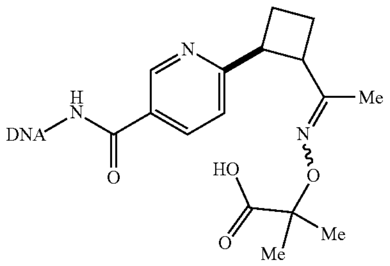

Following General Procedure 5 with S15 and C10.

Yield: $^{38}/_{65}$×100%=58%

Ratio (product/deiodination/aryl iodide): 38/3/0

Exact mass: 5237.0092

Triply charged mass [M]/3-1.00794, calculated 1744.6618; observed 1744.6731.

LC Trace and Mass of 100

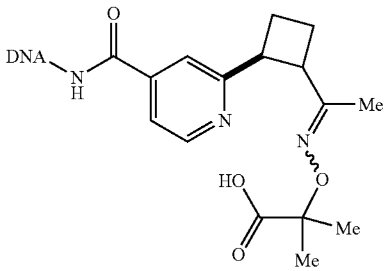

Following General Procedure 5 with S18 and C10.

Yield: $^{29}/_{56}$×100%=52%

Ratio (product/deiodination/aryl iodide): 29/6/2

Exact mass: 5237.0092

Triply charged mass [M]/3-1.00794, calculated 1744.6618; observed 1744.6731.

LC Trace and Mass of 101

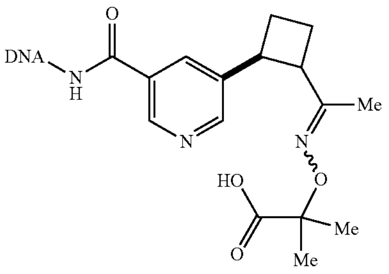

Following General Procedure 5 with S16 and C10.

Yield: 29/79×100%=37%

Ratio (product/deiodination/aryl iodide): 29/6/26

Exact mass: 5237.0092

Triply charged mass [M]/3-1.00794, calculated 1744.6618; observed 1744.6731.

LC Trace and Mass

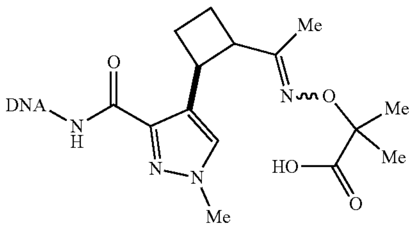

Following General Procedure 5 with S19 and C10 except for employing $H_2O$/DMA (2/1).

Yield: 13/77×100%=17%

Ratio (product/deiodination/aryl iodide): 13/10/29

Exact mass: 5240.0201

Triply charged mass [M]/3-1.00794, calculated 1745.6654; observed 1745.6653.

LC Trace and Mass of 102

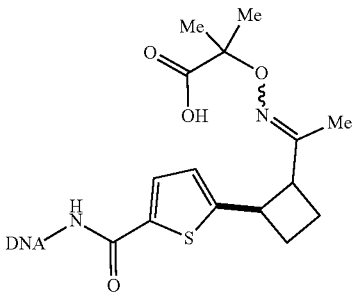

Following General Procedure 5 with S23 and C10.

Yield: 28/69×100%=41%

Ratio (product/deiodination/aryl iodide): 28/3/14

Exact mass: 5241.9704

Triply charged mass [M]/3-1.00794, calculated 1746.3155; observed 1746.3156.

LC Trace and Mass of 103

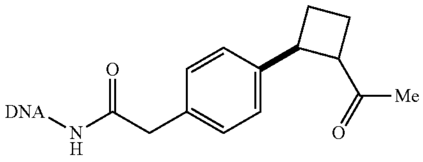

Following General Procedure 6 with 83.

Yield: 40/53×100%=75%

Exact mass: 5148.9819

Triply charged mass [M]/3-1.00794, calculated 1715.3194; observed 1715.3248.

7. Representative Synthesis of Compound 106

Step 1: 1st $C(sp^3)$-H Activation

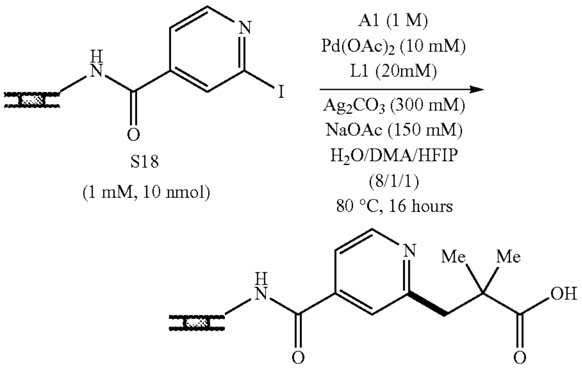

S18

(1 mM, 10 nmol)

31

LC Trace and Mass of 31, see above.

Step 2: Amidation

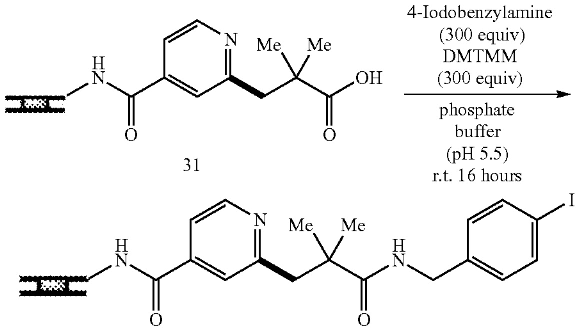

31

104

LC Trace and Mass of 104

Following General Procedure 4 with Compound 31 and 4-iodobenzyl-amine.

Yield: 29/41×100%=71%

Exact mass: 5354.9160

Triply charged mass [M]/3-1.00794, calculated 1783.9641; observed 1783.9607.

Step 3: $2^{nd}$ $C(sp^3)$-H Activation

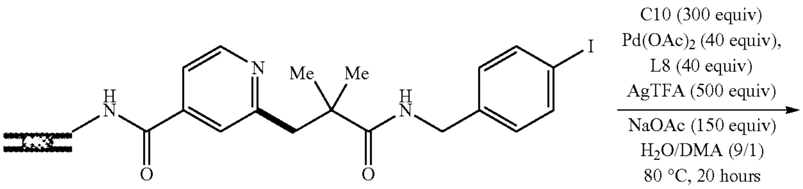

104

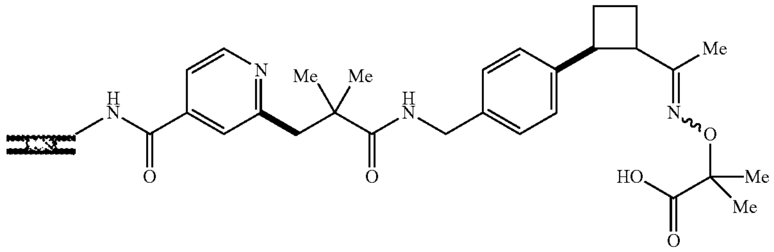

105

LC Trace and Mass of 105

Following General Procedure 5 with 104 and C10.

Yield: 8/29×100%=28%

Exact mass: 5426.1246

Triply charged mass [M]/3-1.00794, calculated 1807.7003; observed 1807.7014.

Step 4: DG Removal

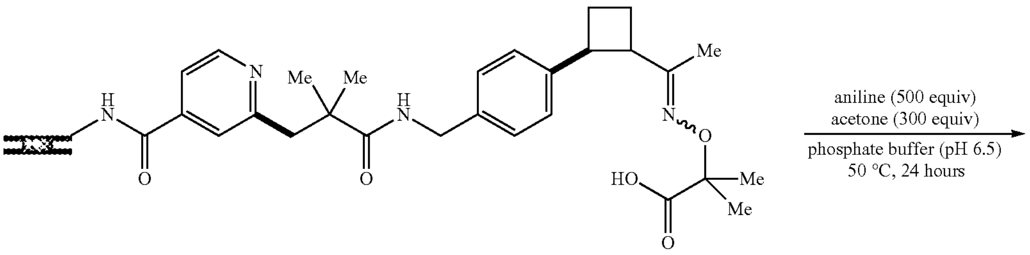

105

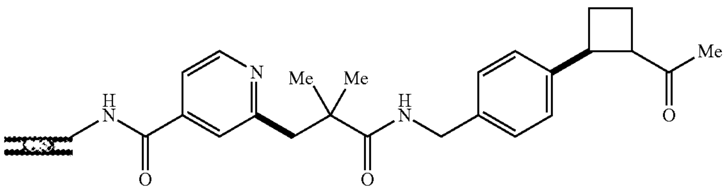

106

LC Trace and Mass of 106

Following General Procedure 6 with 105.

Yield: 3/8×100%=38%

Exact mass: 5325.0769

Triply charged mass [M]/3-1.00794, calculated 1774.0177; observed 1774.0288.

CITATIONS

1. Brenner & Lerner, *Proc. Natl. Acad. Sci. U.S.A.* 89, 5381-5383 (1992).

2. (a) Goodnow, "A Brief History of the Development of Combinatorial Chemistry and the Emerging Need for DNA-Encoded Chemistry". In *A Handbook for DNA-Encoded Chemistry*, Wiley-Blackwell, 2014, pp 19-43; (b) Franzini et al., *Acc. Chem. Res.*, 2014, 47, 1247; (c) Zimmermann & Neri, *Drug Discov. Today*, 2016, 21, 1828; (d) Lerner & Brenner, *Angew. Chem., Int. Ed.*, 2017, 56, 1164; (e) Neri, *ChemBioChem*, 2017, 18, 827; (f) Shi et al., *Bioorg. Med. Chem. Lett.*, 2017, 27, 361; (g) Satz, *ACS Med. Chem. Lett.*, 2018, 9, 408; (h) Zhao et al., *Expert Opin. Drug Discov.*, 2019, 14, 735.

3. (a) Zhao et al., *Angew. Chem., Int. Ed.*, 2014, 53, 10056; (b) Ding et al., *ACS Med. Chem.* Lett., 2015, 6, 888; (c) Arico-Muendel, *Med. Chem.* Commun., 2016, 7, 1898; (d) Belyanskaya et al., *ChemBioChem*, 2017, 18, 837; (e) Neri & Lerner, *Annu. Rev. Biochem.*, 2018, 87, 479; (f)

Yuen et al., *J. Am. Chem. Soc.,* 2019, 141, 5169; (g) Cai et al., *J. Am. Chem. Soc.,* 2019, 141, 17057.

4. (a) Satz et al., *Bioconjug. Chem.* 26, 1623-1632 (2015); (b) Franzini & Randolph, *J. Med. Chem.,* 2016, 59, 6629; (c) Malone & Paegel, *ACS Comb. Sci.,* 2016, 18, 182.
5. (a) Ding &. Clark, *ACS Comb. Sci.,* 2015, 17, 1; (b) Ding et al., *Bioconjug. Chem.,* 2016, 27, 2597; (c) Lu et al., *Bioconjug. Chem.,* 2017, 28, 1625.
6. (a) Lu et al., *Bioconjug. Chem.* 28, 1625-1629 (2017); b) Ruff & Berst, Med. *Chem. Commun.,* 2018, 9, 1188.
7. Wang et al., *iScience,* 2019, 15, 307.
8. (a) Probst et al., *Chem. Eur. J.,* 2018, 24, 1795; (b) Liu al., *Angew. Chem., Int. Ed.,* 2019, 58, 8029; (c) Flood et al., *Angew. Chem., Int. Ed.,* 2020, 59, 7377.
9. (a) Li et al., *Org. Lett.,* 2018, 20, 7186; (b) Gerry et 1., *Org. Lett.,* 2019, 21, 1325; (c) Ma et. al., *Angew. Chem., Int. Ed.,* 2019, 58, 9254; (d) Škopić et al., *J. Am. Chem. Soc.,* 2019, 141, 10546; (e) Potowski et al., *Chem. Sci.,* 2019, 10, 10481.
10. (a) Kölmel et al., *Chem. Med. Chem.,* 2018, 13, 2159; (b) Wang et al., *Proc. Natl. Acad. Sci. U.S.A.,* 2018, 115, E6404; (c) Flood et al., *J. Am. Chem. Soc.,* 2019, 141, 9998; (d) Phelan et al., *J. Am. Chem. Soc.,* 2019, 141, 3723; (e) Badir et al., *Org. Lett.,* 2020, 22, 1046; (f) Ruff et al., *ACS Comb. Sci.,* 2020, 22, 120.
11. (a) He et al., *Chem. Rev.,* 2017, 117, 8754; (b) Zhuang & Yu, *Nature,* 2020, 577, 656.
12. Gerry et al., *J. Am. Chem. Soc.,* 2019, 141, 10225.
13. Wang et al., *Org. Lett.,* 2018, 20, 4764.
14. (a) Chen et al., *Angew. Chem., Int. Ed.,* 2017, 56, 1506; (b) Shen et al., *J. Am. Chem. Soc.,* 2018, 140, 6545-6549.
15. (a) Gong et al., *J. Am. Chem. Soc.,* 2014, 136, 16940; (b) Liu et al., *Angew. Chem., Int. Ed.,* 2017, 56, 10924
16. (a) Zhu et al., *J. Am. Chem. Soc.,* 2017, 139, 16080; (b) Zhu et al., *J. Am. Chem. Soc.,* 2018, 140, 3564.
17. Kölmel & Kool, *Chem. Rev.,* 2017, 117, 10358.
18. Zhuang et al., *J. Am. Chem. Soc.* 2018 140, 10363-10367.
19. Wu et al., *Science* 2017 355, 499-503.
20. Park et al., *ACS Catal.* 2018 8, 9292-9297.
21. Dydio et al., *J. Am. Chem. Soc.* 2011 133, 17176-17179.

Each of the patents, patent applications and articles cited herein is incorporated by reference. The articles "a" and "an" are used herein to refer to one or to more than one (i.e., to at least one) of the grammatical object of the article. By way of example, "an element" means one element or more than one element.

The foregoing description and the examples are intended as illustrative and are not to be taken as limiting. Still other variations within the spirit and scope of this invention are possible and will readily present themselves to those skilled in the art.

The invention claimed is:

1. A method for preparing an aqueous composition containing a library having a plurality of different bifunctional molecules comprising the steps of:

a) reacting in one or more aliquots of aqueous compositions of a bifunctional linker molecule B having termini A' and C' according to the formula A'-B—C', wherein terminus C' contains a bonded iodo-substituted aromatic ring moiety that is free of secondary ring nitrogen atoms and an identifier nucleotide precursor, Z', at terminus A', by palladium-catalyzed arylation by the linker terminal C' iodo-substituted aromatic ring moiety at a β-C($sp^3$)-H or γ-C($sp^3$)-H position of one or more reactant $C_4$-$C_{16}$ aliphatic carboxylic acid, carboxamide or masked ketone units, X', wherein a different X' is present in each aliquot, and adding one or more nucleotide precursors Z' to terminus A' of said linker, a different Z' being added in each aliquot, to form an aqueous composition containing bifunctional molecules having the formula $Z_{n\alpha}$-A-B—C—$X_{n\alpha}$, where n is a position identifier for X and Z and is an integer from 1 to 10, such that when n is 1, X and Z are located most proximal to the linker B, and α identifies one or more specific reactant $C_4$-$C_{16}$ aliphatic carboxylic acid, carboxamide or ketone units X, and the corresponding one or more identifying paired DNA sequences of Z in the bifunctional molecule reactant, where each Z' or Z is paired with and identifies a particular X' or X, respectively;

a') optionally admixing reacted aqueous aliquot compositions containing approximately equal amounts of bifunctional molecules so formed to form a single composition containing a mixture of said bifunctional molecules;

b) reacting the carboxylic acid, carboxamide or ketone functionality present in one or more aliquots of said aqueous composition that contains bifunctional molecules of step a) or a'), $X_{n\alpha}$, with one or more iodo-substituted aromatic ring moiety that is free of secondary ring nitrogen atoms, W', and reacting one or more nucleotide precursor Y' with $Z_{n\alpha}$ to form one or more aqueous compositions containing bifunctional molecules having the formula $Y_{n\beta}$—$Z_{n\alpha}$-A-B—C—$X_{n\alpha}$—$W_{n\beta}$, and b') optionally admixing reacted aqueous aliquot compositions containing approximately equal amounts of bifunctional molecules so formed to form a single composition containing a mixture of said bifunctional molecules;

where each Y' or Y is paired with and identifies a particular W' or W, respectively;

where Z, A, C, X, Y and W are reacted forms of the corresponding Z', A', C', X', Y' and W';

β identifies one or more specific chemical groups W and the corresponding one or more identifying paired DNA sequences of Y in the bifunctional molecule reactant;

c) palladium-catalyzed arylating the iodo-substituted aromatic ring moiety, $W_{n\beta}$, present in the aqueous composition or aliquots thereof formed in step b) to the β-C($sp^3$)-H or γ-C($sp^3$)-H position of a $C_4$-$C_{16}$ aliphatic carboxylic acid, carboxamide or masked ketone unit, V', and reacting nucleotide precursor T' with $Y_{n\gamma}$ to form one or more compositions containing bifunctional molecules having the formula $T_{n\gamma}Y_{n\beta}$—$Z_{n\alpha}$-A-B—C—$X_{n\alpha}$—$W_{n\beta}$—$V_{n\gamma}$;

where each T' or T is paired with and identifies a particular V or V', respectively;

γ identifies one or more specific $C_4$-$C_{16}$ aliphatic carboxylic acid, carboxamide or masked ketone units V and the corresponding one or more identifying paired DNA sequences of Y in the bifunctional molecule reactant;

wherein at least one of reaction steps a), b) and c) includes a plurality of aliquots of an aqueous composition that contains a bifunctional molecule that individually reacted with a reactant different from that reacted in another aliquot at that step, followed by combining the aliquots produced to form an aqueous composition containing admixture of a plurality of different bifunctional molecules that constitute a library of said bifunctional molecules in an aqueous composition.

2. The method of claim 1, which further comprises recovering the library from the aqueous composition.

3. A method of carrying out an arylation reaction of a $C_4$-$C_{16}$ aliphatic carboxylic acid, carboxamide or masked ketone at a position β- or γ- to the position of the carboxylic acid, carboxamide or a carbonyl carbon of the masked ketone, which comprises:

dissolving or dispersing in an aqueous medium an iodo-substituted aromatic ring moiety that is free of secondary ring nitrogen atoms, a $C_4$-$C_{16}$ aliphatic carboxylic acid, carboxamide or masked ketone containing a β-C$(sp^3)$-H or γ-C$(sp^3)$-H, a catalytic amount of a palladium (II) catalyst, a silver salt, a basic alkali metal salt, and an optionally present ligand that interacts with a Pd(II) ion in aqueous media to form an aqueous reaction medium; and maintaining the aqueous reaction medium for a period of about 15 to about 30 hours at a temperature of about 700 to about 100° C. to provide a compound comprising the aromatic ring moiety bound to the $C_4$-$C_{16}$ aliphatic carboxylic acid, carboxamide or masked ketone.

4. The method according to claim 3, wherein the $C_4$-$C_{16}$ aliphatic carboxylic acid, carboxamide or masked ketone containing a β-C$(sp^3)$-H or γ-C$(sp^3)$-H is present in the aqueous reaction medium in a molar excess relative to the iodo-substituted aromatic moiety of 10:1 to about 1200:1.

5. The method according to claim 3, wherein the silver salt and the basic alkali metal salt are present in the aqueous reaction medium in a molar ratio of about 2:1 to about 4:1, and wherein the molar ratio of the silver salt to the iodo-substituted aromatic moiety is about 100:1 to about 400:1.

6. The method according to claim 3, wherein the ligand is present in an amount that is about 1.5 to about 4 times the molar amount of the palladium (II) catalyst.

7. The method according to claim 3, wherein the ligand is selected from the group consisting of one or more of

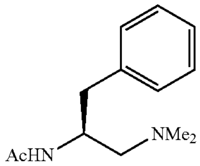
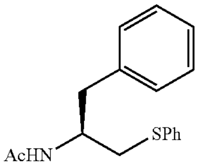
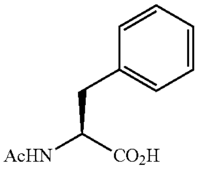
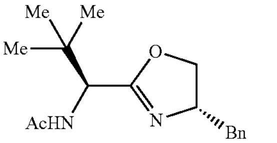
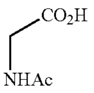
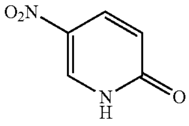
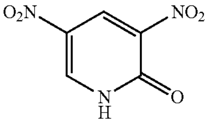
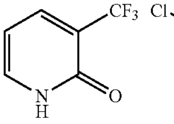
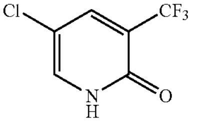
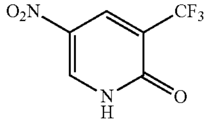
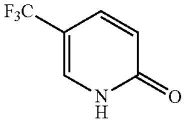

-continued

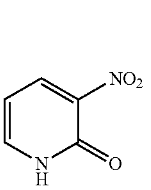
and
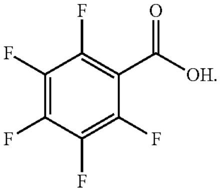

8. The method according to claim 3, wherein the iodo-substituted aromatic ring moiety that is free of secondary ring nitrogen atoms contains a single 5- or 6-membered aromatic ring, is linked to a DNA-containing linker designated "DNA" and is selected from the group consisting of one or more of

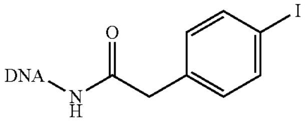
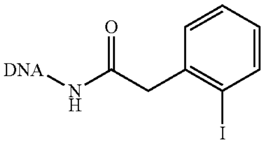
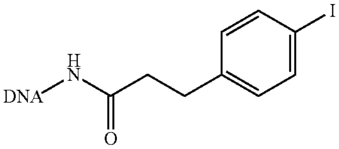
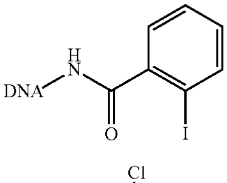
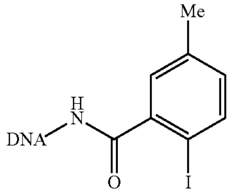
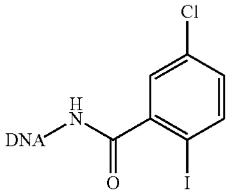
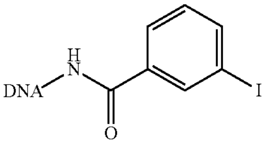
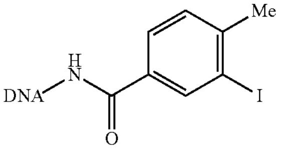
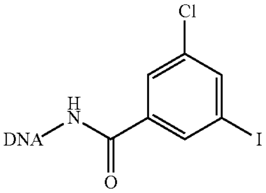
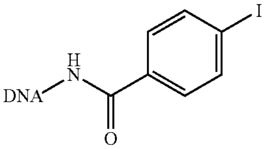
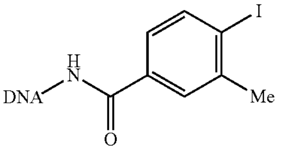
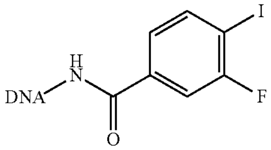
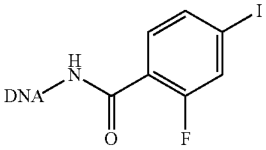
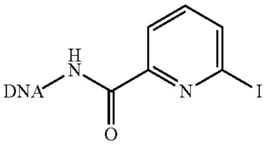

-continued
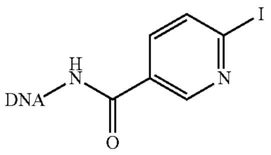
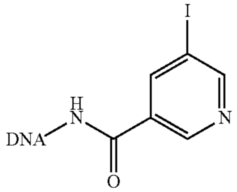
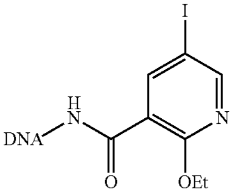
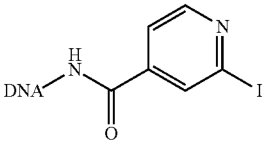
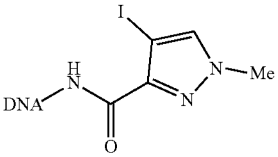
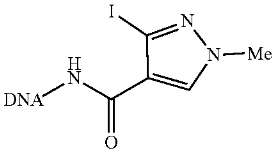
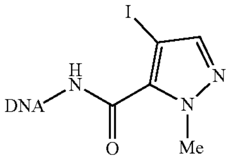
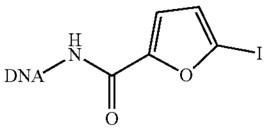
and
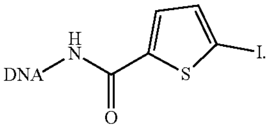
9. The method according to claim 3, wherein the masked ketone containing a β-C($sp^3$)-H or γ-C($sp^3$)-H is selected from the group consisting of one or more of
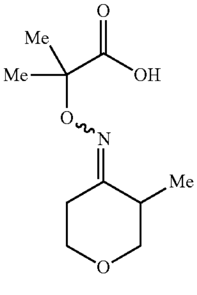
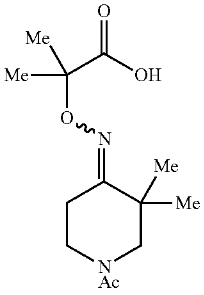
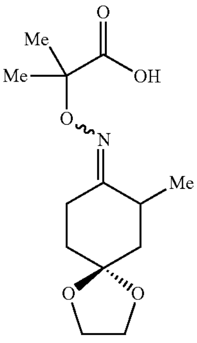
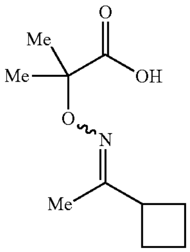
-continued
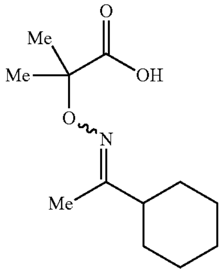
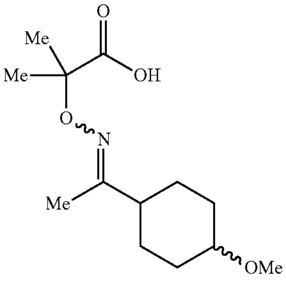
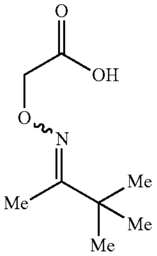
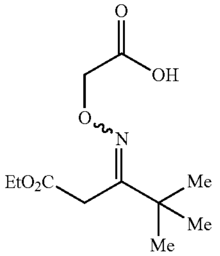
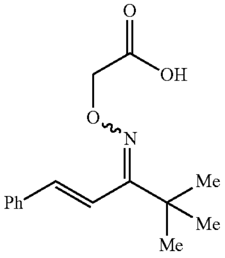
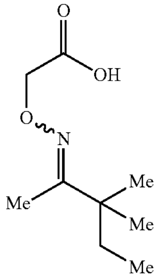
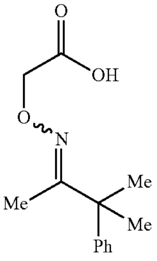
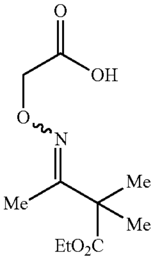
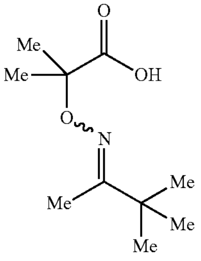
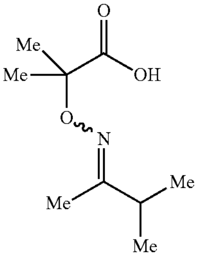
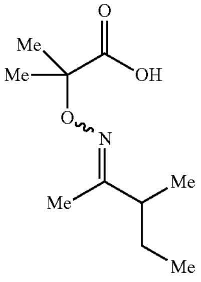
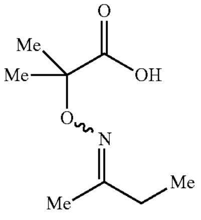

-continued
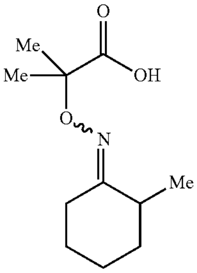
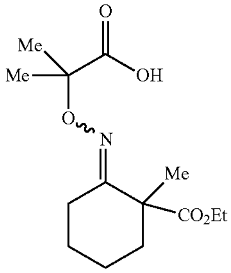
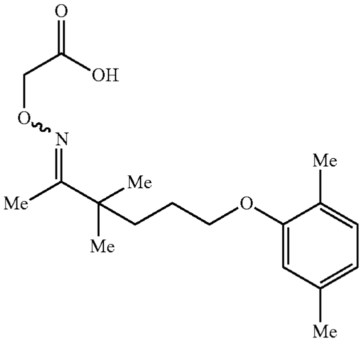
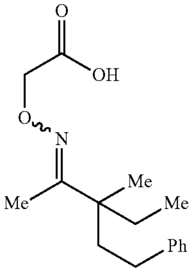
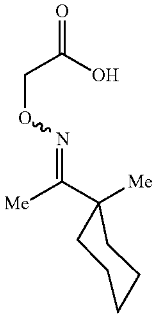
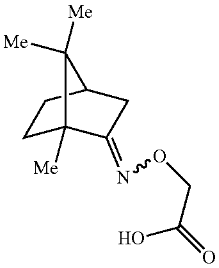
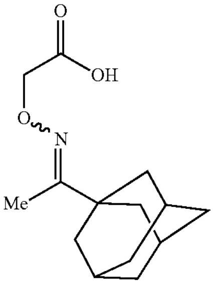
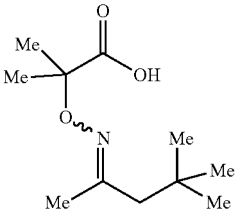
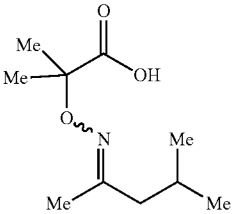
and
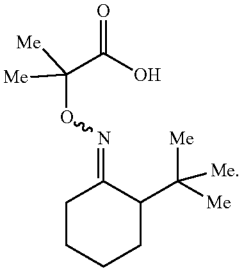
10. The method according to claim 3, wherein the carboxylic acid containing a β-C($sp^3$)-H or γ-C($sp^3$)-H is selected from the group consisting of one or more of
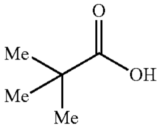
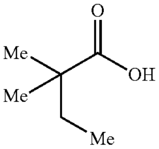
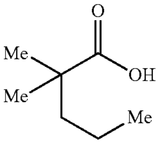
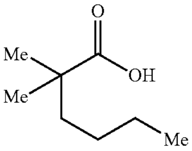
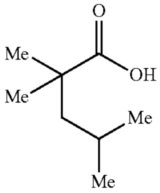
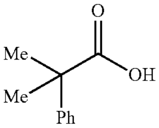
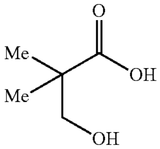
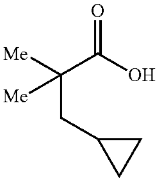
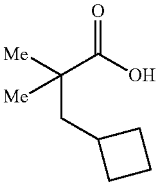
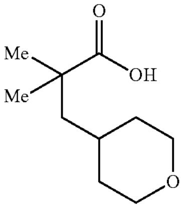
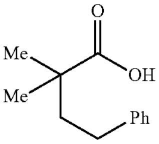
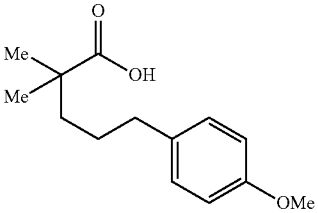
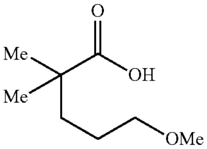
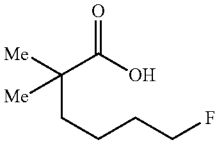
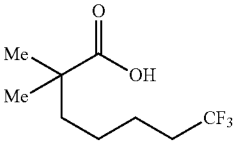
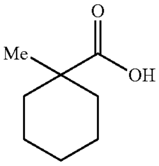
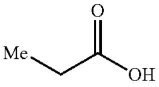
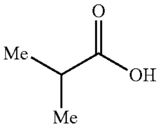
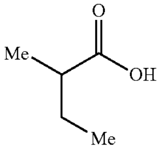
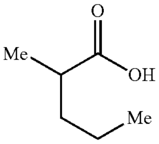
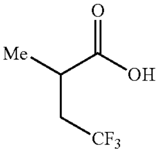
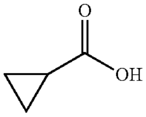
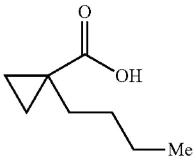
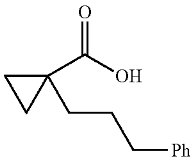

-continued
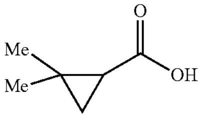
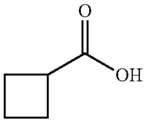
and
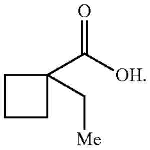
* * * * *